US008440199B2

(12) United States Patent
Rankin et al.

(10) Patent No.: US 8,440,199 B2
(45) Date of Patent: May 14, 2013

(54) METHODS FOR MOBILIZING MESENCHYMAL STEM CELLS IN A PATIENT

(75) Inventors: Sara Margaret Rankin, London (GB); Simon Charles Pitchford, Huntington (GB)

(73) Assignee: Imperial Innovations Limited, London (GB)

( * ) Notice: Subject to any disclaimer, the term of this patent is extended or adjusted under 35 U.S.C. 154(b) by 68 days.

(21) Appl. No.: 12/747,302

(22) PCT Filed: Dec. 12, 2008

(86) PCT No.: PCT/GB2008/004105
§ 371 (c)(1),
(2), (4) Date: Nov. 12, 2010

(87) PCT Pub. No.: WO2009/074807
PCT Pub. Date: Jun. 18, 2009

(65) Prior Publication Data
US 2011/0044997 A1    Feb. 24, 2011

(30) Foreign Application Priority Data

Dec. 12, 2007  (GB) .................................. 0724222.5
Sep. 19, 2008  (GB) .................................. 0817160.5

(51) Int. Cl.
*A61K 39/00* (2006.01)
*A61K 35/26* (2006.01)
*A01N 25/00* (2006.01)

(52) U.S. Cl.
USPC .................. 424/184.1; 424/577; 514/885

(58) Field of Classification Search .................. None
See application file for complete search history.

(56) References Cited

U.S. PATENT DOCUMENTS

| 7,666,393 | B2 * | 2/2010 | Soker et al. | 424/9.2 |
| 2005/0271639 | A1 * | 12/2005 | Penn et al. | 424/93.21 |
| 2006/0110374 | A1 * | 5/2006 | Czeiger et al. | 424/93.7 |
| 2009/0221683 | A1 * | 9/2009 | Losordo | 514/44 R |
| 2010/0028312 | A1 * | 2/2010 | Aikawa et al. | 424/93.21 |

FOREIGN PATENT DOCUMENTS

| WO | 99/47158 | 9/1999 |
| WO | 99/50461 | 10/1999 |
| WO | 00/09152 | 2/2000 |
| WO | 01/16161 | 3/2001 |
| WO | 01/56591 | 8/2001 |
| WO | 01/85196 | 11/2001 |
| WO | 02/094261 | 11/2002 |
| WO | 2004/022078 | 3/2004 |
| WO | 2004/024178 | 3/2004 |
| WO | 2004/096840 | 11/2004 |
| WO | 2005/121123 | 12/2005 |
| WO | 2006/074426 | 7/2006 |
| WO | 2006/126188 | 11/2006 |
| WO | 2007/022385 | 2/2007 |
| WO | 2007/047882 | 4/2007 |
| WO | 2007/064620 | 6/2007 |

OTHER PUBLICATIONS

Shepherd et al . (Blood, 2006, v.108, pp. 3662-3667).*
Aicher et al., Hypertension 45:321-325 (2005).
Aluti et al., J. Exp. Med. 185:111-120 (1997).
Asahara et al., Science 275:964-967 (1997).
Asahara et al., Circ. Res. 85:221-228 (1999).
Broxmeyer et al., J. Exp. Med. 201(8):1307-1318 (2005).
Cashen et al., Curr. Haem. Rep. 3:406-412 (2004).
Calandra et al., Bone Marrow Transplantation 41:331-338 (2008).
Chamberlain et al., Stem cells 25:2739-2749 (2007).
Capoccia et al., Blood 108:2438-2445 (2006).
De Clercq et al., Mini-Rev. Med. Chem. 5:805-824 (2005).
Ferrara et al., Nat. Medicine 9:669-676 (2003).
Flomenberg et al., Blood 106:1867-1874 (2005).
Gerber et al., J. Biol. Chem. 273:30336-30343 (1998).
Giordano et al., J. Cell. Physiol. 211:27-35 (2007).
Hamada et al., Circulation 114(18):S284; Abstract No. 1475, 2000.
Hatse et al., FEBS Letters 527:255-262 (2002).
Hattori et al., J. Exp. Med. 193:1005-1014 (2001).
Heil et al., Angiogenesis 6(3):201-211 (2003).
Hendrix et al., Antimicrobial Agents and Chemotherapy 44:1667-1673 (2000).
Ichiyama et al., PNAS USA 100:4185-4190 (2003).
Ince & Nienaber, Nature Clin. Pract 4 suppl 1:S114-S118 (2007).
IPRP with Written Opinion; PCT/GB2008/004105; D. Mulhausen; Jun. 15, 2010.
Iwasaki et al., Circulation 114:35 Abstract No. 319 (2006).
Jones et al., Cytometry Part B (Clinical Cytometry) 70B:391-399 (2006).
Kang et al., Lancet 363:751-756 (2004).
LaRochelle et al., Blood 107:3772-3778 (2006).
Levesque et al., J. Clin. Invest. 111:187-196 (2003).
Li et al., Faseb J. 20(9):E664-E676 (2006).
Liles et al., Blood 102:2728-2730 (2003).
Martin et al., Br. J. Haem. 134:326-329 (2006).
Ortiz et al., PNAS USA 100(14):8407-8411 (2003).
Prockop et al., PNAS USA 100 supp. 1:11917-11923 (2003).
Prockop DJ, Clin. Pharmacol. Ther. 82(3):241-3 (2007).
Prockop D & Olson, Blood 109(8):3147-51 (Epub Dec. 14, 2006)(2007).
Pusie and DiPersio, Curr. Pharm. Des. 14:1950-61 (2008).
Ripa RS, Circulation 116[supp 1] I-24-I-30 (2007).
Roncalli et al., Circulation 116:261 Abstract No. 1279 (2007).
Roufosse et al., Intl. J. Biochem. & Cell Biol. 36:585-597 (2004).
Seeger et al., Nature Clinical Practice: Cardiovascular Medicine 4:S110-S113 (2007).
Semerad et al., Immunity 17:413-423 (2002).
Shepherd et al., Blood 108:3662-3667 (2006).
Soeki et al., Heart Vessels 15:105-111 (2000).
Takano H., Trends Pharm. Sci 28 (10):512-7 (Epub Sep. 20, 2007) (2007).
Thomas et al., Curr. Opin. Hematol. 9:183-9 (2002).
Tondreau et al., Stem Cells 23:1105-1112 (2005).
Wang et al., PNAS USA 102(1):186-191 (2005).
Wengner et al., Blood. 111:42-49 (2008).
Yin et al., J. Cardiovasc. Pharmacol. 50:61-67 (2007).
Yoder et al., Blood 109:1801-1809 (2007).
Yoon et al., Circulation. 112:1618-1627 (2005).
Morikawa et al. (2009) J. Exp. Med 206:2483-96.

* cited by examiner

*Primary Examiner* — Michail Belyavskyi
(74) *Attorney, Agent, or Firm* — Fish & Richardson P.C.

(57) ABSTRACT

The current invention provides a method for mobilizing endothelial progenitor cells (EPC) and/or mesenchymal stem cells (MSC) in a patient, wherein the method comprises the steps of (i) administering a vascular endothelial growth factor receptor (VEGFR) agonist to the patient; and (ii) administering an antagonist of CXCR4 to the patient. Also provided are uses of EPC and MSC harvested using the methods of the invention.

19 Claims, 27 Drawing Sheets a. Experimental Protocol:

b. HPCs c. EPCs d. SPCs a. Experimental Protocol:

b. HPCs c. EPCs d. SPCs a.

b.

c.i.

ii.

iii.

iv.

d.i.

ii.

iii.

iv.

e.i.

ii.

iii.

iv.

a. HPCs b. EPCs c. SPCs

METHODS FOR MOBILIZING MESENCHYMAL STEM CELLS IN A PATIENT

This invention relates to methods for mobilising select populations of stem cells, in particular endothelial progenitor cells and mesenchymal stem cells.

BACKGROUND

Haematopoietic Progenitor Cells

Haematopoietic progenitor cells (HPCs) are bone marrow derived stem cells that form the cellular constituents of blood (i.e. erythrocytes and leukocytes) and have the capacity to re-constitute bone marrow that has previously been ablated by irradiation. HPCs are used for bone marrow transplants (BMTs). HPCs are harvested from donors by mobilizing these cells into the blood. Currently the cytokine G-CSF is used to mobilize HPCs (Cashen et al, (2004) *Curr. Haem. Rep.* 3: 406-412) and it has been shown that maximal mobilization requires treatment daily over 4 consecutive days (or over 3-5 days), with blood being collected on day 5. However, in approximately 20% of patients not enough HPCs are mobilized to perform a BMT. Thus there is a need to find more effective reagents for mobilizing HPCs. The term Haematopoietic stem cell (HSC) is used interchangeably with HPC herein and references to HSC are intended to include reference to HPC.

CD34+ HPCs express the receptor CXCR4 and migrate in response to the chemokine stromal cell-derived factor (SDF)-1α (CXCL12) (Aiuti et al, (1997) *J. Exp. Med.* 185: 111-120). CXCR4 is the receptor for CXCL12, which is expressed constitutively in the bone marrow. There is evidence that CXCL12/CXCR4 is required for both the retention of HPCs within the bone marrow and their homing back to the bone marrow. AMD3100 is a specific CXCR4 antagonist and it stimulates a rapid rise in circulating numbers of HPCs in both mice and humans (Hatse et al, (2002) *FEBS Letters* 527: 255-262; Liles et al, (2003) *Blood* 102: 2728-2730; Broxmeyer et al, (2005) *J. Exp. Med.* 201: 1307-1318).

Recently it has been shown that the CXCR4 antagonist has the capacity to rapidly mobilize HPCs from the bone marrow within 1 h. Furthermore, we and others have shown a synergistic effect of chronic G-CSF treatment combined with acute treatment with AMD3100 with respect to HPC mobilization (Martin et al, (2006) *Br. J. Haem.* 134: 326-329; Broxmeyer et al, (2005) *J. Exp. Med.* 201: 1307-1318; Flomenberg et al, (2005) *Blood* 106: 1867-1874). Such a combined treatment is currently in phase III clinical trials for HPC mobilization.

Endothelial Progenitor Cells

Endothelial progenitor cells (EPCs) are bone marrow-derived progenitor cells that have been shown to contribute to vascularisation following tissue injury. In particular, following ischemia reperfusion injury such as occurs during myocardial infarction. EPCs contribute to the formation of new blood vessels and are thus thought to be clinically beneficial. The use of EPCs for treating conditions such as ischemic heart disease is reviewed in Seeger et al, (2007) *Nature Clinical Practice: Cardiovascular Medicine* 4: S110-S113.

An increase in EPCs in the blood is seen in patients with heart disease and correlates with the clinical outcome. It has been proposed that mobilizing EPCs from the bone marrow may be beneficial in such patients and a number of clinical trials have examined the effect of G-CSF treatment on mobilisation of stem cells in patients suffering acute myocardial infarction. Overall the results of these studies have been disappointing (Ince & Nienaber, (2007) *Nature Clin. Pract* 4 suppl 1: S114-S118; Takano H (2007) *Trends Pharm. Sci.* 28(10): 512-7 (Epub 2007 Sep. 20); and Ripa R S (2007) *Circulation* 116[suppl I]: I-24-I-30 and references cited therein). We believe that this may reflect the fact, as shown here, that G-CSF is not the most efficacious treatment to mobilize EPCs. Ripa et al. (2007) *Circulation* 116[suppl I]: I-24-I-30 shows that G-CSF mobilises HPCs but causes a decrease in MSCs. This may explain why G-CSF is not appropriate as a stem cell mobilising reagent. Furthermore G-CSF has other effects that may affect disease progression. Thus G-CSF has been shown to promote the survival of cardiac myocytes, which could also be beneficial in this disease setting. G-CSF also induces granulopoiesis and a dramatic rise in circulating neutrophils which may be detrimental to the heart, exacerbating the inflammatory process (Kang et al., (2004) *Lancet*. 363: 751-756). For these reasons it is difficult to interpret the previous and on-going trials using G-CSF to mobilize stem cells. Reagents that selectively mobilize EPCs from the bone marrow may be clinically useful in the treatment of heart disease (Ferrara et al., (2003) *Nat. Medicine.* 9: 669-676).

Mesenchymal Stem Cells

Mesenchymal stem cells (MSCs) are bone marrow-derived stem cells that have the capacity to differentiate into adipocytes, chondrocytes and osteocytes, ie exhibit tri-lineage differentiation. The tri-lineage differentiation of MSCs may be tested ex vivo as proof of the presence of MSCs. Some studies suggest that MSCs may be able to differentiate into other lineages, such as neuronal and epithelial cells. However, this is still controversial and not yet widely accepted. In the context of the present invention, it is expected that the MSCs exhibit said tri-linage differentiation under appropriate culture conditions, but they may also be able to differentiate into other cells.

We would also predict mobilised MSCs to retain the ability to differentiate into a more appropriate and therapeutically useful regenerative cell type depending on the tissue which was being targeted. It is possible that MSCs will differentiate into other lineages dependent on the disease/tissue environment, eg MSCs recruited into the damaged lung may differentiate into epithelial cells to repair damaged tissues. This is suggested in Ortiz et at (2003) *PNAS USA* 100(14): 8407-8411, which provides evidence that MSCs may be useful for tissue repair in respiratory diseases. Wang et at (2005) *PNAS USA* 102(1): 186-191 provides further evidence that MSCs possess the capacity of differentiating into airway epithelia, which suggests that MSC may provide a therapy for cystic fibrosis. As such it is believed that MSCs may be used clinically for tissue regeneration, for example, in the treatment of osteogenesis imperfecta. MSCs are reviewed in Roufosse et al, (2004) *Intl. J. Biochem. & Cell Biol.* 36: 585-597.

A recent review by Prockop D J ((2007) *Clin. Pharmacol. Ther.* 82(3): 241-3) encapsulates the current view that ability of MSCs to differentiate into different cell types (e.g. osteocytes or neurons) i.e. their "stemness", may not be the reason why these cells are so effective in vivo at promoting tissue repair. The experimental evidence suggests that MSCs may repair tissues via their production of chemokines and cytokines. Potential mechanisms of tissue repair by MSCs are also discussed in Prockop at al (2003) *PNAS USA* 100 supp. 1: 11917-11923. Even though the mechanism of tissue repair has not yet been fully elucidated; it is clear that MSCs are therapeutically active and have many proven and potential uses.

EPCs and MSCs can be recognised in practice by a number of characteristics. Firstly, EPCs and MSCs only grow in defined culture media and colony growth takes on an easily identifiable morphology. Secondly, via FACS analysis, EPCs and MSCs can be further defined by the expression of distinct antigens. Antigen expression on MSCs is reviewed in Chamberlain et al., (2007) *Stem cells*. 25: 2739-2749; and Roufosse et al., (2004) *International J. Biochem. & Cell. Biol.* 36: 585-597. Antigen expression in EPCs is described in Yoon et al., (2005) *Circulation*. 112: 1618-1627; and Yoder et al., (2007) *Blood* 109: 1801-1809. A protocol for the detection, enumeration and phenotypic analysis of MSCs using flow cytometry is provided in Jones et al (2006) *Cytometry Part B (Clinical Cytometry)* 70B: 391-399.

Human MSCs are typically defined as cells that are:
1. Plastic adherent (ie adherent to typical plastic cell culture vessels);
2. Triple positive for the cell surface markers CD105, CD73 and CD90;
3. Negative for the cell surface markers, CD34, CD45, CD14, CD11b and CD19; and
4. Exhibit tri-lineage differentiation.

Murine MSCs exhibit 1 and 4 (above), but the CD markers may be different (for references see above).

Human EPCs are typically defined as cells that are:
1. Adherent to tissue culture plasticware pre-coated with an extracellular matrix protein, e.g. fibronectin;
2. Positive for the cell surface markers CD34 or CD133 and VEGFR2; and
3. Uptake acetylated LDL and stain positive for GS-Lectin.

Additionally it has been shown that MSCs are immunosuppressive. In vitro they have been shown to inhibit T cell proliferation, promote the differentiation of T cells into T reg cells and inhibit monocyte differentiation into dendritic cells. In vivo MSCs have been used in animal models for the treatment of diabetes, rheumatoid arthritis, systemic lupus erythematosus and multiple sclerosis. Finally MSCs have been shown to improve allogenic bone marrow engraftment following transplantation. It is believed that MSCs may be used for the treatment of autoimmune diseases, such as rheumatoid arthritis or sclerederma. Indeed to date >1000 people worldwide have received bone marrow transplants for autoimmune disease, for example for the treatment of therapy-resistant Graft Versus Host Disease or rejection of organ allographs. A review of the current and potential clinical uses of MSCs is provided in Giordano et al (2007) *J. Cell. Physiol.* 211: 27-35.

MSCs represent <0.001% of bone marrow cells (Tondreau et al, (2005) *Stem Cells* 23: 1105-1112). Isolation requires ex vivo expansion of MSCs in FCS containing growth medium. There are a number of problems associated with such isolation and expansion procedures, including the use of FCS, the potential of MSCs to transform and the possibility that such ex vivo culture may reduce the functionality of these cells. For example, see Procock D & Olson (2007) *Blood*. 109(8): 3147-51 (Epub 2006 Dec. 14), page 3150 indicates that MSCs expanded ex vivo may form tumours in vivo.

The factors regulating the mobilization of MSCs are currently unknown.

In the present application we identify factors regulating the mobilization of HPCs, EPCs and MSCs. We identify factors that selectively mobilize EPCs and/or MSCs are therefore useful for the clinical applications as described above.

DESCRIPTION OF THE INVENTION

In a first aspect the current invention provides a method for mobilising mesenchymal stem cells (MSC) and/or endothelial progenitor cells (EPC) in a patient, wherein the method comprises the steps of (i) administering a vascular endothelial growth factor receptor (VEGFR) agonist to the patient; and (ii) administering an antagonist of CXCR4 to the patient. The VEGFR agonist may be either a natural ligand or recombinant protein acting on the receptor ie a non-recombinant or recombinant VEGF, or placental growth factor (PIGF), or a synthetic compound that acts as an agonist. The term VEGFR agonist, as used herein, is intended to include VEGF, PIGF and any other natural, synthetic or recombinant compound (or mixture of compounds) with the property of VEGFR agonism.

As used herein, the terms mesenchymal stem cell (MSC) and stromal progenitor cell (SPC) are interchangeable. Any reference to MSC is also a reference to SPC and any reference to SPC is also a reference to MSC.

The biological actions of VEGF are mediated by three receptor tyrosine kinases (VEGFR-1, VEGFR-2, and VEGFR-3). VEGF (also named VEGFA) belongs to a gene family that includes placental growth factor (PIGF), VEGF-B, VEGF-C, VEGF-D, and VEGF-E. VEGF-A has been identified as a key regulator of blood vessel angiogenesis and also haematopoietic survival, whilst VEGF-C and VEGF-D regulate lymphatic angiogenesis. VEGF-A is able to bind to VEGFR-1 and VEGFR-2, whilst PIGF and VEGF-B selectively bind to VEGFR-1. Further selectivity has been shown with VEGF-E specifically binding to VEGFR-2, whilst VEGF-C and VEGF-D bind to VEGFR-2 and VEGFR-3 (Ferrara et al., (2003) *Nature Medicine*. 9: 669-676).

In a preferred embodiment of all aspects of the invention the VEGFR agonist is a VEGFR-2 agonist. In a particularly preferred embodiment the VEGFR-2 agonist is selective for VEGFR-2 to the exclusion of VEGFR-1 and 3. The VEGFR-2 agonist may be VEGF-E, or a derivative thereof. The VEGFR-2 agonist may alternatively be a further small molecule that selectively agonises VEGFR-2.

It is envisaged that the selective agonism of VEGFR-2 may reduce unwanted side effects in the patient by preventing agonism of unnecessary targets. Examples 3 and 4 indicate that the action of VEGF in mobilising MSCs and EPCs in response to CXCR4 antagonism is via VEGFR-2 and not VEGFR-1. Thus the reduction of VEGFR-1 agonism may increase efficacy and reduce unwanted effects.

It is envisaged that the MSC and/or EPC are mobilised principally from the bone marrow of the patient. MSCs may also be mobilised from mesenchymal tissues, adipose tissue, liver, tendons, synovial membrane, amniotic fluid, placenta, umbilical cord and teeth.

In an embodiment of the first aspect of the invention the VEGFR agonist is administered chronically to the patient. By 'chronic administration' is meant administration to the patient at regular intervals over a long period of time, for example 3-5 days. This may include administration of VEGFR agonist daily over a period of several days, for example, three-five days. The frequency of dosage to the patient and the length of time over which the VEGFR agonist is administered to the patient may be decided by the clinician with the benefit of clinical trials. This may depend on the physical condition of the patient or on other factors. For example, patients with heart disease have been shown to have elevated plasma levels of VEGF (Soeki et al (2000) *Heart Vessels* 15: 105-111). Patients who have an elevated plasma level of VEGF may require a lower dose of VEGF (or none at all) to be administered in conjunction with a CXCR4 antagonist, in the context of the current invention. Other factors that may affect the dosage of VEGFR agonist may include the age (younger patients are known to be able to mobilise HPCs better than older patients (Thomas et al (2002) *Curr. Opin.*

*Hematol.* 9: 183-9)), gender, weight, build or fitness of the patient or alternatively may include some other relevant factor.

In a further embodiment of the first aspect of the invention the antagonist of CXCR4 is administered acutely to the patient. By 'acute administration' is meant administration of the CXCR4 antagonist over a short period of time, for example, over one or several hours or less than one hour, but not more than 24 hours. It is preferred that the administration of CXCR4 antagonist is performed by way of a single injection. However, it may alternatively be administered through a number of administrations or may alternatively be a constant administration over said period of time. It is preferred that the CXCR4 antagonist is administered subcutaneously. An example of subcutaneous administration of the CXCR4 antagonist AMD-3100 is provided in Hendrix et al (2000) *Antimicrobial Agents and Chemotherapy* 44: 1667-1673. Alternatively, the CXCR4 antagonist may be administered intraperitoneally as in Example 1, orally, intravenously or by any other appropriate means. The appropriate means of administration will depend on the CXCR4 antagonist used and the condition or species of the patient. The length of time and the means for delivery may be decided by a clinician with the benefit of clinical trials. As with the administration of a VEGFR agonist, the condition of the patient may affect the means of administration of the CXCR4 antagonist.

A further aspect of the invention provides a method for mobilising mesenchymal stem cells (MSC) and/or endothelial progenitor cells (EPC) in a patient with elevated circulating levels of VEGF, wherein the method comprises administering an antagonist of CXCR4 to the patient. An example of such a patient is provided in Soeki et at (2000) *Heart Vessels* 15: 105-111, as described above. It is envisaged that the circulating levels of VEGF in such a patient would be sufficient to be equivalent to the chronic administration of a VEGFR agonist as described in other aspects of the current invention. Thus the step of administering a VEGFR agonist to the patient would not be necessary in such patients and the mobilisation of the MSC and EPC could be achieved with administration of CXCR4 antagonist alone. CXCR4 antagonist may be administered acutely to such patients.

In an embodiment of the preceding aspect the method may further comprise administering a VEGFR-1 antagonist. The VEGFR-1 antagonist may be an antibody or a fragment thereof. As indicated in Example 4, the antagonism or blocking of VEGFR-1 with an anti-VEGFR-1 antibody, in the presence of chronic VEGF administration and acute CXCR4 antagonism, led to a significant increase in MSC mobilisation. It is envisaged that provision of such a VEGFR-1 antagonist in a patient with elevated levels of VEGF and in combination with CXCR4 antagonism will increase MSC mobilisation.

A VEGFR-1 antagonist may also be used in all other aspects of the current invention.

A further aspect includes a method of inhibiting the mobilisation of HSC in a patient, wherein the method comprises the steps of (i) administering a VEGFR agonist (natural or synthetic) to the patient; and (ii) administering an antagonist of CXCR4 to the patient. MSCs and/or EPCs may be mobilised from the bone marrow of the patient in conjunction with the inhibition of HSC mobilisation. In an embodiment the VEGFR agonist may be administered chronically to the patient. In a further embodiment the antagonist of CXCR4 may be administered acutely. For example, it is envisioned that in the treatment of an individual with an inflammatory disease (e.g. COPD—chronic obstructive pulmonary disease), reducing the circulating numbers of neutrophils will prevent disease progression, while EPCs and MSCs may promote tissue repair.

In an embodiment the antagonist of CXCR4 is administered directly/locally to a perfused bone. This may be more useful in a non-human animal than in a human.

In any aspect of the current invention the antagonist of CXCR4 may be AMD3100. Other CXCR4 antagonists are also in development. Examples of CXCR4 antagonists are provided in WO 01/85196; WO 00/09152; WO 99/47158; Ichiyama et al (2003) *PNAS USA* 100: 4185-4190; WO 01/16161; WO 01/56591; WO 01/85196; WO 2004/024178; WO 2006/074426; WO 2005/121123; WO 2006/074428; WO 2004/096840; WO 2007/022385; WO 02/094261; WO 2007/064620; WO 2006/126188; and WO 99/50461, which are incorporated herein by reference. The antagonist of CXCR4 may be, for example, a peptide, peptide analogue, peptidomimetic, a small molecule such as the bi-cyclam AMD-3100 or any other molecule capable of antagonising the CXCR4 receptor.

It is intended that in any aspect of the current invention the agonist of VEGFR may be VEGF, PIGF or any other natural, synthetic or recombinant compound (or combination of compounds) with the property of VEGFR agonism.

In an embodiment of the first aspect the method is for harvesting MSC and/or EPC. This may apply to any of the preceding embodiments. The MSC and/or EPC may be harvested from a body fluid using techniques known in the art. For example, the MSC and/or EPC may be harvested from a perfused bone or extracted bone marrow, for example using the methods described in Example 1 or other methods known in the art. This may have the advantage of yielding a more highly enriched population of MSC and/or EPC than those harvested from circulating blood or other bodily fluid, though harvesting from circulating blood or other body fluid may be more convenient. A method for the isolation of human MSCs using a mAb to Low affinity nerve growth factor receptor (LNGFR) is described in Jones et al (2006) *Cytometry B Clin Cytom.* 70(B): 391-9.

The harvested MSC and/or EPC may be cultivated in vitro. This further step may facilitate the expansion of MSC and/or EPC in populations of cells where they are in a minority. This may be useful in samples from patients that respond less well to the methods of the current invention. Alternatively, cultivation in vitro may allow modifications to be made to the cells as necessary depending on their intended use. The cultivated cells may be administered back to the patient or to another patient. The use of cells in other patients will be particularly beneficial in patients who are unable to produce their own MSC and/or EPC. It may be beneficial to use cells cultivated from the same patient for treatment of that patient to reduce the risk of rejection by the patient's immune response. The cultivation step may allow treatment of a patient with his own cells where that patient is unable to produce sufficient numbers of such cells due to a deficiency in their bone marrow. The deficiency in the patient's bone marrow may be as a result of chemotherapy, radiotherapy, an autoimmune disease, a genetic condition or any other such condition. Alternatively, the reintroduction of a patient's own cells after cultivation may be useful for targeted delivery of such cells to the intended site of action. For example, in the treatment of tissue damage following ischemia cells could be targeted to the site of tissue damage. Re-introduction to the site of tissue damage/disease, may be appropriate for example in heart disease. The G-CSF clinical trials that have showed most promise are those where mobilised cells were isolated from the blood and then injected back into the heart by an intracoronary injection (Takano H (2007) *Trends Pharm. Sci.,* 28(10): 512-7 (Epub 2007 Sep. 20))

Thus, stem cells mobilised by the methods of the current invention may be used for either autologous or allogenic stem cell transplants (i.e. either mobilising cells from the patient to be put back into that same patient, or from donor to patient).

The harvested MSC and/or EPCs may be used for banking of the stem cells (i.e. younger individuals banking their stem cells for future use). For example, the banked cells could be used if that individual has a heart attack. There are many stem cell banks that have been set up to store cord blood stem cells (eg cells4life and futurehealth) and some that already offer to store adult bone marrow stem cells. There are already companies that will bank bone marrow. The reasoning behind this is that it is thought that stem cell numbers decline as you age, therefore you can harvest more when you are younger. Further, one of the advantages of obtaining adult rather than cord blood stem cells is their lifespan when frozen. Thus, most stem cell banks offer to store cord blood stem cells for a maximum of 25 years. This is fine if they are used to treat childhood leukemias or possibly an ageing parent, but for the baby they would not be there when they are 50 and have a heart attack. If a human subject stored adult bone marrow stem cells when they were 40, they would be available for that subject up to the age of 65. These cells could also be used for sports injuries and chronic wounds or for treating any other condition where tissue repair and regeneration would be beneficial. At present, injured racehorses are treated with MSCs by taking bone marrow, cultivating it ex vivo and then injecting the stem cells directly back into the site of injury (http://www.vetcell.comlindex.htm and WO 2004/022078). Thus the MSCs harvested by the current method may also be used in patients with sports injuries and chronic wounds as MSCs are effective at promoting tissue repair and can form cartilage and osteocytes. The cultivated cells may be genetically modified. This may be carried out in vitro or in vivo. This could be used to replace dysfunctional cells. The genetic modification may lead to cells that are more efficacious or more compatible with the recipient of such cells. The genetically modified cells may be more resistant to apoptosis than the wild-type cells. This could be achieved by the introduction of, or knockout of, genes involved in apoptotic mechanisms. It may alternatively be achieved by fusion with another cell. For example, the cultivated cells may be fused with immortal cells. The cultivated cells may also be fused with cells that express chemokine receptors or adhesion molecules, to facilitate trafficking to damaged tissues.

The cultivated cells may be targeted to damaged tissue in the recipient of said cultivated cells. This may be achieved by introducing genes encoding specific receptors, adhesion molecules or antibodies into the cultivated cells. Alternatively, this may be achieved by attaching antibodies targeted to the damaged tissue, to the surface of the cells. Methods for targeting cells in this way are known in the art. A method for directing stem cells to the heart by direct injection into the coronary artery has been utilised in a number of clinical trials (Takano H (2007) *Trends Pharm. Sci.,* 28(10): 512-7 (Epub 2007 Sep. 20)). The damaged tissue where the cultivated cells may be targeted may have been damaged by ischemia, radiotherapy, chemotherapy, auto-immune disease or physical injury.

It is envisaged that the population of MSC and/or EPC in the sample from the patient would be further enriched by the property of inhibition of HSC mobilisation by a VEGFR agonist and CXCR4 antagonism demonstrated herein (FIGS. 3 and 4). HSC are much more abundant in the bone marrow than MSC and EPC as can be seen in FIG. 19. The method of the current invention will lead to a reduction in HSC mobilisation in conjunction with the increase in MSC and EPC mobilisation.

In a further aspect the invention provides a population of MSC or EPC or combination thereof, mobilised and harvested from a patient, after administration of a VEGFR agonist and an antagonist of CXCR4 to that patient, for use in repairing damaged blood vessels, for tissue regeneration, for treating myocardial infarction, stroke (heart disease), peripheral ischaemia, diabetes, autoimmune disease (e.g. rheumatoid arthritis, sclerederma, graft versus host disease, rejection of organ allografts), systemic lupus erythematosus, multiple sclerosis, cystic fibrosis or other respiratory disease, for immunosuppression, for treating sports injuries or for the healing of chronic wounds. Populations of mobilised cells can be distinguished in terms of the ratios of MSCs:EPCs:HSCs released. For example in murine blood under basal conditions the ratio of MSCs:EPCs:HSCs is 0:1:10. Following G-CSF+CXCR4 antagonist treatment the ratio becomes 0:1:200, whilst following treatment with the VEGFR agonist+CXCR4 antagonist the ratio becomes 1:12:5.

A yet further aspect provides the use of a population of MSC or EPC or combination thereof, that has been mobilised and harvested from a patient after administration of a VEGFR agonist and an antagonist of CXCR4 to that patient, in the manufacture of a medicament for repairing damaged blood vessels, for tissue regeneration, for treating myocardial infarction, stroke (heart disease), peripheral ischaemia, diabetes, autoimmune disease (e.g. rheumatoid arthritis, sclerederma, graft versus host disease, rejection of organ allografts), systemic lupus erythematosus, multiple sclerosis, cystic fibrosis or other respiratory disease, for immunosuppression, for treating sports injuries or for the healing of chronic wounds.

A further aspect provides a method for repairing damaged blood vessels, for tissue regeneration, for treating myocardial infarction, stroke (heart disease), peripheral ischaemia, for treating diabetes, autoimmune disease (e.g. rheumatoid arthritis, sclerederma, graft versus host disease, rejection of organ allografts), systemic lupus erythematosus, multiple sclerosis, cystic fibrosis or other respiratory disease, for immunosuppression, for treating sports injuries or for the healing of chronic wounds in a patient, the method comprising the step of administering an effective amount of a population of MSC or EPC or combination thereof, that has been mobilised and harvested from a patient after administration of a VEGFR agonist and an antagonist of CXCR4 to that patient.

In a further aspect the invention provides a method of identifying an effective antagonist of CXCR4 in a patient, wherein the method comprises the steps of (i) administering a VEGFR agonist to the patient; (ii) administering a test compound to the patient; and (iii) determining the level of MSC and/or EPC in a sample from the patient. It is envisioned that the sample is a blood sample but it may also be a sample of lymph or other bodily fluid.

A further aspect provides the use of a VEGFR agonist in combination with an antagonist of CXCR4 in the manufacture of a medicament for treating myocardial infarction, stroke, peripheral ischaemia, for treating diabetes, rheumatoid arthritis, systemic lupus erythematosus, multiple sclerosis, cystic fibrosis or other respiratory disease, an autoimmune disease, sclerederma or ischemia, for treating sports injuries or for the healing of chronic wounds. It is envisioned that such diseases may be treated by stimulating the increased mobilisation of MSC and/or EPC in a patient, which may naturally home to damaged tissue. Such cells would circulate to the site of action in the patient and stimulate the repair of tissue, immunosuppression or other effect as necessary. The methods of the current invention may enable mobilisation of cells in patients where the use of other mobilisation methods has been shown to be potentially harmful to the patient. For example, the use of G-CSF for mobilisation in patients with sickle cell anaemia has resulted in severe sickle cell crisis and even death (Larochelle et al, (2006) *Blood* 107: 3772-3778). The use of a VEGFR agonist and a CXCR4 antagonist may have fewer or no side effects in such patients.

The invention also provides a VEGFR agonist in combination with an antagonist of CXCR4 for use in treating myocardial infarction, stroke, peripheral ischaemia, treating diabetes, rheumatoid arthritis, systemic lupus erythematosus, multiple sclerosis, cystic fibrosis or other respiratory disease, an autoimmune disease, sclerederma, ischemia, Alzheimer's disease or Parkinson's disease.

A further aspect provides a method for mobilising MSC and/or EPC for use in treating diabetes, heart disease, rheumatoid arthritis, systemic lupus erythematosus, multiple sclerosis, cystic fibrosis or other respiratory disease, an autoimmune disease, sclerederma or ischemia or for use in repairing damaged blood vessels, for tissue regeneration, or for immunosuppression in a patient, wherein the MSC and/or EPC are mobilised using a VEGFR agonist in combination with an antagonist of CXCR4.

A yet further aspect provides the use of a VEGFR agonist in combination with an antagonist of CXCR4 in the manufacture of a medicament for mobilising MSC and/or EPC. The mobilising of MSC and/or EPC may be for treating myocardial infarction, stroke, peripheral ischaemia, diabetes, rheumatoid arthritis, systemic lupus erythematosus, multiple sclerosis, cystic fibrosis or other respiratory disease, an autoimmune disease, sclerederma or ischemia or for use in repairing damaged blood vessels, for tissue regeneration, or for immunosuppression in a patient.

The invention also provides a population of stem cells isolated from a patient, wherein the patient has been treated with a VEGFR agonist in combination with an antagonist of CXCR4, the population of stem cells having a ratio of MSC: EPC:HPC which is significantly different to that found in the patient before said treatment. The ratio of MSC:EPC:HSC before treatment is envisaged to be, for example, 0:1:10. The ratio after treatment may be, for example, 0:12:5. In murine blood under basal conditions the ratio of MSCs:EPCs:HSCs is 0:1:10. Following G-CSF+CXCR4 antagonist treatment the ratio becomes 0:1:200, whilst following treatment with the VEGFR agonist+CXCR4 antagonist the ratio becomes, for example 1:12:5. Thus, a population of the invention may have a MSC:ESC:HSC ratio of A:B:C, wherein C is less than 200×B, preferably less than 100×B, still more preferably less than 50, 20, 15, 10, 5, 2, 1 or 0.5×B and wherein A is preferably at least 0.1, preferably 0.2×C.

In the current invention the patient may be any mammal. It is intended that the patient is a human but it may also be a mouse, rat or other rodent, a goat, sheep or other farm mammal, a horse, rabbit, dog, cat or other domestic pet, an ape or a monkey. The patient may be a racing or sporting animal, for example a racehorse, polo pony or greyhound.

Any documents referred to herein are hereby incorporated by reference. The listing or discussion of a prior-published document in this specification should not necessarily be taken as an acknowledgement that the document is part of the state of the art or is common general knowledge.

The invention will now be described in more detail by reference to the following, non-limiting, Figures and Examples.

FIGURES

FIG. 1: HPC mobilization from mouse femoral bone marrow after G-CSF pre-treatment and subsequent AMD3100 stimulation.

Mice were administered 2.5 µg G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last G-CSF injection. Perfusate was collected for an additional 50 minutes, and haematopoietic progenitor cell colonies were established.

FIG. 2: Circulating HPC numbers after pre-treatment with G-CSF and subsequent AMD3100 stimulation.

Mice were administered 2.5 µg G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last G-CSF injection. Cardiac punctures were performed 60 minutes later and blood was collected for enumeration of HPC colonies.

FIG. 3: HPC mobilization from mouse femoral bone marrow after VEGF pre-treatment and subsequent AMD3100 stimulation.

Mice were administered 2.5 µg VEGF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF injection. Perfusate was collected for an additional 50 minutes, and haematopoietic progenitor cell colonies were established.

FIG. 4: Circulating HPC numbers after pre-treatment with VEGF and subsequent AMD3100 stimulation.

Mice were administered 2.5 µg VEGF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF injection. Cardiac punctures were performed 60 minutes later and blood was collected for enumeration of HPC colony formation.

FIG. 5: EPC mobilization from mouse femoral bone marrow after G-CSF pre-treatment and subsequent AMD3100 stimulation.

Mice were administered 2.5 µg G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last G-CSF injection. Perfusate was collected for an additional 50 minutes, and EPC colonies were established.

FIG. 6: Circulating EPC numbers after pre-treatment with G-CSF and subsequent AMD3100 stimulation.

Mice were administered 2.5 µg G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last G-CSF injection. Cardiac punctures were performed 60 minutes later and blood was collected for enumeration of EPC colonies.

FIG. 7: EPC mobilization from mouse femoral bone marrow after VEGF pre-treatment and subsequent AMD3100 stimulation.

Mice were administered 2.5 µg VEGF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF injection. Perfusate was collected for an additional 50 minutes, and both early and late endothelial progenitor cell colonies were established.

FIG. 8: Circulating EPC numbers after pre-treatment with VEGF and subsequent AMD3100 stimulation.

Mice were administered 2.5 μg VEGF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF injection. Cardiac punctures were performed 60 minutes later and blood was collected for enumeration of EPC colony formation.

FIG. 9: MSC mobilization from mouse femoral bone marrow after G-CSF pre-treatment and subsequent AMD3100 stimulation.

Mice were administered 2.5 μg G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last G-CSF injection. Perfusate was collected for an additional 50 minutes, and haematopoietic progenitor cell colonies were established.

FIG. 10: Circulating MSC numbers after pre-treatment with VEGF and subsequent AMD3100 stimulation.

Mice were administered 2.5 μg G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last G-CSF injection. Cardiac punctures were performed 60 minutes later and blood was collected for enumeration of MSC colonies.

FIG. 11: MSC mobilization from mouse femoral bone marrow after VEGF pre-treatment and subsequent AMD3100 stimulation.

Mice were administered 2.5 μg VEGF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF injection. Perfusate was collected for an additional 50 minutes, and mesenchymal stem cell colonies were established.

FIG. 12: Circulating MSC numbers after pre-treatment with VEGF and subsequent AMD3100 stimulation.

Mice were administered 2.5 μg VEGF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF injection. Cardiac punctures were performed 60 minutes later and blood was collected for enumeration of MSC colony formation.

FIG. 13: Effect of chronic G-CSF or VEGF administration on AMD3100 induced HPC mobilization.

Mice were administered 2.5 μg VEGF, G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF or G-CSF injection. Perfusate was collected or an additional 50 minutes, and HPC colonies were established.

FIG. 14: Circulating HPC numbers after pre-treatment with G-CSF or VEGF and AMD3100 stimulation.

Mice were administered 2.5 μg VEGF, G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF or G-CSF injection. Cardiac punctures were performed 60 minutes later and blood was collected for enumeration of HPC colonies.

FIG. 15: Effect of chronic G-CSF or VEGF administration on AMD3100 induced EPC mobilization.

Mice were administered 2.5 μg VEGF, G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF or G-CSF injection. Perfusate was collected for an additional 50 minutes, and EPC colonies were established.

FIG. 16: Circulating EPC numbers after pre-treatment with G-CSF or VEGF and AMD3100 stimulation.

Mice were administered 2.5 μg VEGF, G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF or G-CSF injection. Cardiac punctures were performed 60 minutes later and blood was collected for enumeration of HPC colonies.

FIG. 17: Effect of chronic G-CSF or VEGF administration on AMD3100 induced MSC mobilization.

Mice were administered 2.5 μg VEGF, G-CSF or vehicle (naïve) on 4 consecutive days (groups represented by bars). These groups were then infused with AMD3100 (AMD, a CXCR4 antagonist 0.1 mM) or vehicle (0) for 10 minutes into the hind limb 24 h after the last VEGF or G-CSF injection. Perfusate was collected for an additional 50 minutes, and MSC colonies were established.

FIG. 18: Circulating MSC numbers after pre-treatment with G-CSF or VEGF and AMD3100 stimulation.

Mice were administered 2.5 μg VEGF, G-CSF or vehicle (naïve) on 4 consecutive days (groups represented by bars). These groups were then injected with AMD3100 (AMD, a CXCR4 antagonist 5 mg/kg i.p) or vehicle (0) 24 h after the last VEGF or G-CSF injection. Cardiac punctures were performed 60 minutes later and blood was collected for enumeration of MSC colonies.

FIG. 19: Frequency of HPC, EPC and MSC colonies in Bone Marrow.

FIG. 20: G-CSF and VEGF pre-treatment differentially regulate circulation of progenitor cells in response to a CXCR4 antagonist.

a, Experimental protocol. Mice were pre-treated with G-CSF, VEGF, or vehicle (PBS) once daily for 4 days (100 μg/kg i.p.). 24 hours after the last injection, mice were administered a CXCR4 antagonist (AMD3100 5 mg/kg i.p, closed bars) or vehicle (PBS, open bars). 60 minutes later, blood was taken for analysis of circulating: b, CFU-HPC; c, CFU-EPC; and d, CFU-SPC. CFU-HPC, CFU-EPC, and CFU-SPC are shown as number of colonies per ml blood. n=5-8 mice per group. Data: means±s.e.m. *: P<0.05, : P<0.01, *: P<0.001 between selected groups.

FIG. 21: G-CSF and VEGF pre-treatment differentially regulate mobilization of progenitor cells in response to a CXCR4 antagonist.

a, overview of procedures set up for identifying the direct mobilization of progenitor cells from the femoral bone marrow. Mice were pre-treated with G-CSF, VEGF, or vehicle (PBS) once daily for 4 days (100 μg/kg i.p.). 24 hours after the last injection, mice underwent perfusion of the right hind limb. CXCR4 antagonist (AMD3100 0.1 mM, closed bars) or vehicle (PBS, open bars) were then infused directly into the femoral artery for 10 minutes. The hind limb was then perfused for a further 50 minutes to allow collection of b, CFU-HPC; c, CFU-EPC; or d, CFU-SPC; via the femoral vein. CFU-HPC, CFU-EPC, and CFU-SPC are shown as total number of colonies collected in the perfusate. n=5-8 mice per group. Data: means±s.e.m. *: P<0.05, : P<0.01, *: P<0.001 between selected groups.

FIG. 22: VEGF-treatment does not alter the number of progenitor cells residing in the bone marrow, or the morphology of the bone marrow.

Mice were treated with G-CSF, VEGF, or vehicle (PBS), administered once daily for 4 days (100 μg/kg i.p.). 24 hours after the last injection, bone marrow was aspirated for the enumeration of a, CFU-HPC bone marrow frequency; b, CFU-EPC bone marrow frequency; and c, CFU-SPC bone marrow frequency. Femurs from other mice were fixed in situ and processed for: d, bone marrow morphology of vehicle and VEGF-treated mice, at ×20, and ×60 objective. n=4-8 per group. Data: mean±s.e.m. *: P<0.05, ***: P<0.001 between selected groups.

FIG. 23: VEGF-treatment does not alter the expression of CXCR4 on HPCs or EPCs. However, VEGF suppress bone marrow-derived HPC chemotaxis towards SDF-1α.

Mice were treated with G-CSF, VEGF, or vehicle (PBS), administered once daily for 4 days (100 µg/kg i.p.). Bone marrow was aspirated on day 5 and harvested cells were used to determine a, SDF-1α levels in bone marrow supernatant as determined by ELISA; b, % of bone marrow Lin$^-$ Sca-1$^+$ cells expressing CXCR4; and c, % of bone marrow CD34$^+$ VEGFR2$^+$ cells expressing CXCR4. Harvested cells were also utilized in the following chemotaxis assays: d, number of HPCs; and e, EPCs undergoing chemotaxis towards 30 nM SDF-1α. Cells taken from bone marrow of mice treated with G-CSF (closed bars) or vehicle (PBS, open bars). f, number of HPCs; and g, EPCs undergoing chemotaxis towards 30 nM SDF-1α. Cells taken from bone marrow of mice treated with VEGF (closed bars) or vehicle (PBS, open bars). n=4-8 per group. Data: mean±s.e.m. *: P<0.05, ***: P<0.001 between selected groups.

FIG. 24: VEGF pre-treatment suppresses neutrophil mobilization, but does not affect their ability to undergo chemotaxis.

Mice were pre-treated with G-CSF, VEGF, or vehicle (PBS), administered once daily for 4 days (100 µg/kg i.p.). 24 hours later these mice underwent perfusion of the right hind limb. CXCR4 antagonist (AMD3100 0.1 mM, closed bars) or vehicle (PBS, open bars) were then infused directly into the femoral artery for 10 minutes. The hind limb was then perfused for a further 50 minutes to allow collection of a, neutrophils via the femoral vein. In other perfusion experiments, CXCR4 antagonist or PBS were infused in addition to VEGF (50 nM), G-CSF (50 nM), or vehicle (PBS) into the femoral artery of naïve mice for 10 minutes. The hind limb was again perfused for a further 50 minutes to allow b, collection of neutrophils. In some groups of mice pre-treated with VEGF over 4 days, KC (30 µg/kg i.v.) was administered 24 hours after the last injection of VEGF and c, circulating neutrophil numbers (determined by blood smears) were counted 60 minutes after administration of KC (closed bars) or vehicle (PBS, open bars). d, % of Gr-1$^{high}$ neutrophils expressing CXCR2; and e, Neutrophil chemotaxis towards KC (30 nM) of neutrophils taken from bone marrow of mice pre-treated with VEGF, or vehicle (PBS). f, leukocyte counts of bone marrow taken from mice pre-treated with VEGF, G-CSF or vehicle (PBS). n=4-8 mice per group. Data: mean±s.e.m. *: P<0.05, ***: P<0.001 between selected groups.

FIG. 25: VEGF pre-treatment, acting via VEGFR1 enhances HPC cell cycling compared to EPCs.

a, number of cells per colony; and b, mean colony area; of CFU-HPC grown for 12 days in methocult. Cells were taken from bone marrow of mice treated (once daily for 4 days) with G-CSF, VEGF, or vehicle (PBS) (100 µg/kg i.p.). Representative histograms of PI stain of DNA content for Lin$^-$ Sca-1$^+$ HPCs, c.i, PBS-treated, c.ii VEGF-treated, c.iii G-CSF-treated, and c.iv, % of Lin$^-$ Sca-1$^+$ HPCs residing in S/G$_2$/M phase of the cell-cycle. Representative histograms of PI stain of DNA content for CD34$^+$ VEGFR2$^+$ EPCs d.i, PBS-treated, d.ii VEGF-treated, d.iii G-CSF-treated, and d.iv, % of CD34$^+$ VEGFR2$^+$ EPCs residing in S/G$_2$/M phase of the cell-cycle.

In another experiment, mice were treated with anti-VEGFR1 antibody (2.5 mg/kg) or control IgG on days 1 and 3, 30 minutes before VEGF administration. Representative histograms of PI stain of DNA content for Lin$^-$ Sca-1$^+$ HPCs, e.i, PBS-treated, e.ii VEGF-treated+anti-IgG, e.iii VEGF-treated+anti-VEGFR1 antibody, and e.iv, % of Lin$^-$ Sca-1$^+$ HPCs residing in S/G$_2$/M phase of the cell-cycle. n=4-7 per group. Data: mean±s.e.m. *: P<0.05, **: P<0.01 between selected groups.

FIG. 26: VEGFR1 blockade reverses VEGF-induced suppression of HPC mobilization in response to a CXCR4 antagonist.

Mice were pre-treated with VEGF, or vehicle (PBS) once daily for 4 days (100 µg/kg i.p.). Mice pre-treated with VEGF were additionally administered control IgG or anti-VEGFR1 antibody (2.5 mg/kg) on days 1 and 3, 30 minutes before VEGF administration. 24 hours after the last injection, mice were administered a CXCR4 antagonist (AMD3100 5 mg/kg i.p, closed bars) or vehicle (PBS, open bars). 60 minutes later, blood was taken for analysis of circulating: a, CFU-HPC; b, CFU-EPC. c, Representation of the divergent roles of G-CSF and VEGF treatment on HPC and EPC status in bone marrow. n=4 per group. Data: mean±s.e.m. *: P<0.05, ***: P<0.001 between selected groups.

FIG. 27: Immunostaining of bone marrow-derived HPCs and EPCs.

Colonies of HPCs a, and EPCs b, derived from bone marrow cells, were stained for the expression of CD115 (red), CD34 (red), CD45 (red), VEGFR1 (red), VEGFR2 (green), VE-Cadherin (red), vWF (green). Nuclei were counterstained with DAPI (blue).

FIG. 28: GS-Lectin stain, AC-LDL uptake, and tubule formation of bone marrow derived EPCs.

a, CFU-EPC were stained for GS-Lectin (green) and their ability to uptake Ac-LDL (red). Resuspended EPCs were added to a angiogenesis supporting matrix gel for the evaluation of tubule formation. b, EPCs 1 hour after addition to matrix; c, tubule formation was apparent after 18 hours in culture, when luminal structures were evident, d.

FIG. 29: Immunostaining of mobilized EPCs.

Colonies of mobilized EPCs were stained for the expression of CD115 (red), CD14 (red), CD45 (red), CD34 (red), VEGFR1 (red), VEGFR2 (green), VE-Cadherin (red), and vWF (green). Nuclei were counterstained with DAPI (blue).

FIG. 30: Immunostaining of bone-marrow-derived SPCs, mobilized SPCs, and tri-lineage differentiation potential.

a, colonies of SPCs derived from bone marrow cells were stained for the expression of CD29 (red), Cd105 (red), CD45 (red), CD34 (red), VEGFR1 (red), VEGFR2 (green), and VE-Cadherin (red). b, colonies of mobilized SPCs were stained for the expression of CD29 (red), CD105 (red), CD45 (red), CD34 (red), VEGFR1 (red), VEGFR2 (green), VE-Cadherin (red), and vWF (green). Nuclei were counterstained with DAPI (blue). Expanded colonies subjected to specific differentiation media revealed SPCs were able to display a tri-lineage differentiation potential towards c, adipocytes (oil red O); d, osteocytes (Alizarin red); e, chondrocytes (toluidine blue).

FIG. 31: Acutely administered VEGF or G-CSF do not selectively modulate progenitor cell mobilization either alone, or in combination with a CXCR4 antagonist.

Mice underwent perfusion of the right hind limb. CXCR4 antagonist (AMD3100 0.1 mM, closed bars) or vehicle (PBS, open bars) alone, or in combination with G-CSF (50 nM), or VEGF (50 nM) were then infused directly into the femoral artery for 10 minutes. The hind limb was then perfused for a further 50 minutes to allow collection of a, CFU-HPC; b, CFU-EPC; and c, CFU-SPC via the femoral vein. CFU-HPC, CFU-EPC, and CFU-SPC are shown as total number of colonies per perfusate. n=5-8 mice per group. Data: means±s.e.m. : P<0.01, *: P<0.001 between selected groups.

FIG. 32: Blocking the VEGFR1 increases the mobilization of SPCs after treatment a with VEGF and administration of CXCR4 antagonist.

Mice were pre-treated with VEGF, or vehicle (PBS) once daily for 4 days (100 μg/kg i.p.). Mice pre-treated with VEGF were additionally administered control IgG or anti-VEGFR1 antibody (2.5 mg/kg) on days 1 and 3, 30 minutes before VEGF administration. 24 hours after the last injection, mice were administered a CXCR4 antagonist (AMD3100 5 mg/kg i.p, closed bars) or vehicle (PBS, open bars). 60 minutes later, blood was taken for analysis of circulating SPCs. n=4 per group. Data: mean±s.e.m. ***: P<0.001 between selected groups.

FIG. 33 Effect of VEGF & AMD3100 pre-treatment on serum TNFα levels in LPS peritonitis For 4 days prior to LPS challenge mice received either 2.5 μg VEGF in 250 μL PBS i.p. or 250 μL PBS i.p. 30 minutes prior to LPS challenge on day 5 mice received either 150 μg AMD3100 in 100 μL saline i.p. or 100 μL saline i.p. Mice were challenged with either 50 μg LPS in 100 μL PBS or 100 μL PBS i.p (control). Mice were anaesthetised with urethane after 1 h, blood was obtained by cardiac puncture and serum collected. TNFα levels were measured by ELISA. n=3.

EXAMPLE 1

Effect of a CXCR4 Antagonist in Combination with Either G-CSF or VEGF on Mobilisation of HPC, EPC and MSC In Vivo Methodology Chronic Pre-Treatment with G-CSF or VEGF.

Female BALB/c mice were given a subcutaneous injection of vascular endothelial growth factor (VEGF, 2.5 μg/mouse, Peprotech 450-32), Granulocyte-colony stimulating factor (G-CSF, 2.5 μg/mouse, Peprotech 250-05) or vehicle on 4 consecutive days. 24 hours after the last injection, mice were administered a CXCR4 antagonist (AMD3100, 5 mg/kg i.p), or vehicle and blood was collected via cardiac puncture 1 hour later for enumeration of circulating leukocyte, HPC, EPC and MSC levels. In other experiments, mice pre-treated with G-CSF or VEGF were used for in situ perfusion of the mouse hind limb as explained below.

In Situ Perfusion of Mouse Hind Limb

On day 5, mice were anaesthetized with urethane (25% 0.2 ml i.p.) and the femoral artery and vein exposed. The hind limb was isolated by occlusion of the external iliac artery, superficial epigastric and muscular branch with 5/0 braided silk suture. Polyethylene cannulae (0.61 mm OD, Portex, London, UK) were immediately inserted into the femoral artery and vein and tied in place with 5/0 braided silk suture. Perfusion buffer (modified Krebs-Ringer bicarbonate buffer) at 37° C. was infused (0.15 ml/min) via the arterial cannula and removed from the venous cannula using a Minipuls peristaltic pump (Anachem, Luton, UK). The hind limb was perfused for an initial 10 minutes to remove remaining blood from the vasculature and then perfused for a further 60 min with vehicle alone or AMD3100, a CXCR4 antagonist (0.1 mM, Sigma UK) infused over the first 10 minutes using an infusion/withdrawal pump (Harvard Instruments, U.K.).

Analysis of Mobilized Cells from the Bone Marrow in Blood and Perfusate.

The perfusate was collected and centrifuged and the cell pellet re-suspended in Dulbecco's modified eagles medium (DMEM) with 20% fetal bovine serum (FBS). A total cell count was performed before the perfusate was lysed for red blood cells, re-suspended again in DMEM (20% FBS) and used for assays outlined below to enumerate haematopoietic progenitor cells (CFU-HPC), endothelial progenitor cells (CFU-EPC), and leukocyte populations.

In some experiments blood was taken to enumerate HPCs, EPCs and leukocytes. A total cell count was performed on citrated blood before being lysed for red blood cells and re-suspended in DMEM (20% FBS).

Enumeration of Leukocyte Populations

Bone marrow and perfusate cytospins, and blood smears were stained using DiffQuick. Mononuclear cells, eosinophils, and neutrophils were counted using standard morphological criteria using a microscope under a ×100 objective.

CFU-HPC Assay $5 \times 10^4$ cells were added to 1 ml of Methocult medium (M3434, purchased from Stem cell technologies) supplemented with specific cytokines and growth factors to enable formation of CFU-GMs, BFU-Es and CFU-GEMMs. Assay was performed in duplicate Mobilised cells were maintained in semi-solid methylcellulose cultures for 11 days before quantification of the number of CFU-HPCs.

CFU-EPC Assay $1 \times 10^6$ cells were added to 3 ml EPC colony media (EGM-2 basal media+supplements, and additional VEGF: 60 μg/L, and FBS: 16% final concentration). Assay was performed in duplicate. Dishes were incubated for 7 days before media was changed, and then incubated for a further 14 days before the enumeration of late outgrowth endothelial progenitor cells. Early outgrowth endothelial progenitor cells were enumerated on day 5.

CFU-MSC Assay $4 \times 10^5$ cells were added to 3 ml Mesencult media including supplements (05501 and 05502 Stemcell Technologies). Assay was performed in duplicate. Dishes were incubated for 7 days before media was changed, and then incubated for a further 14 days before the enumeration of mesenchymal stem cell colonies.

In each of the above assays, the total number of colony forming units mobilised is calculated according to the number of colonies per plate×by the total number of leukocytes mobilized/number of cells seeded.

Results

Two types of experiments have been performed. In both sets of experiments mice are pre-treated with the cytokine (G-CSF or VEGF) for 4 days by single subcutaneous injections. On day 5 (i.e. 24 hours after the last injection) the mice were divided into 2 groups.

Group 1—Bone Marrow Perfusion System

Mice were anaesthetised and the femoral artery and vein was cannulated such that the femoral bone marrow could be perfused (Martin et al, (2006) *Br. J. Haem.* 134: 326-329). In these mice the CXCR4 antagonist, AMD3100, (or vehicle control) was infused into the femoral vasculature for 10 mins and the perfusate was collected over a period of 60 mins. Thus the results represent stem cells mobilised from the bone marrow over 60 min.

Group 2—In Vivo Technique

Mice were injected i.p. with the CXCR4 antagonist, AMD3100, (or vehicle control) and 1 h later the mice were killed. Blood was collected by cardiac puncture and stem cell numbers in the blood were determined. This methodology measures circulating numbers of stem cells 60 min after the administration of AMD3100.

An important finding of this study was that the pattern of stem cell mobilisation was the same irrespective of the method used to quantify mobilisation.

Haematopoietic Progenitor Cells (HPC)

Endothelial Progenitor Cells (EPC)

Figure 5:
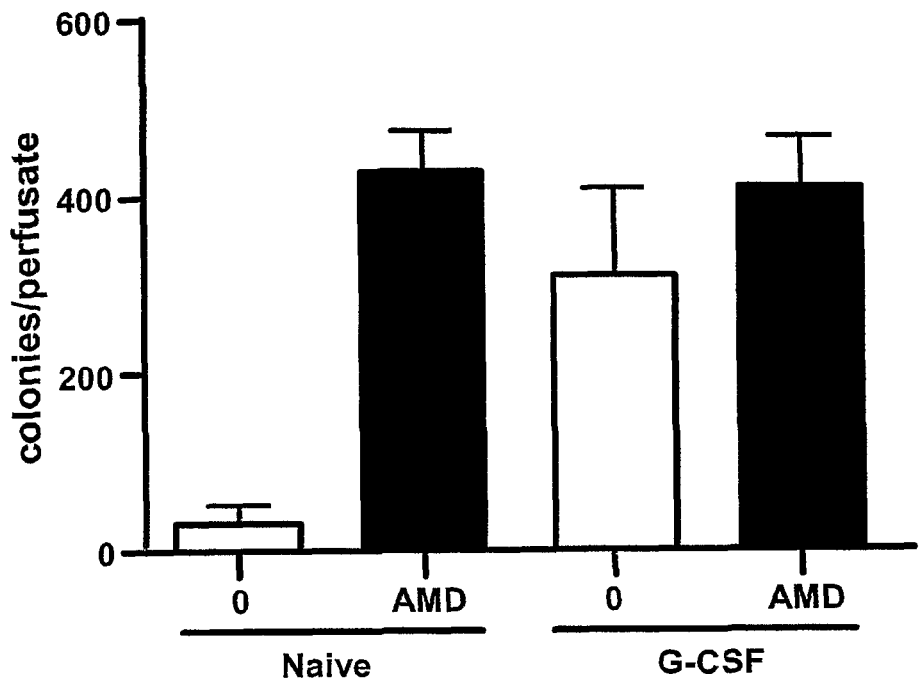
Figure 6:
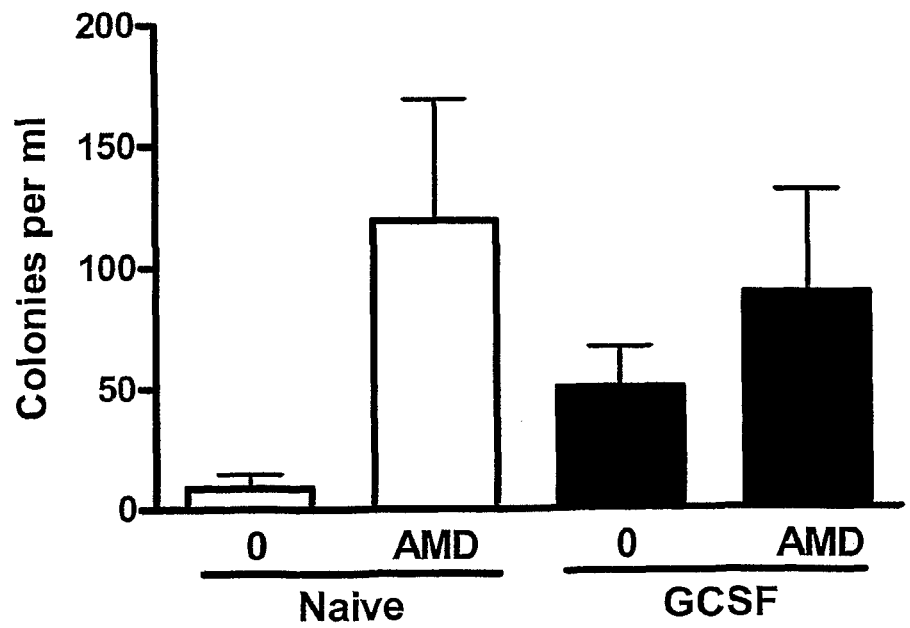

FIGS. 5 and 6 show that AMD3100 (CXCR4 antagonist) alone stimulates the mobilization of EPCs. This effect is not enhanced by pre-treatment with G-CSF.

Figure 1:
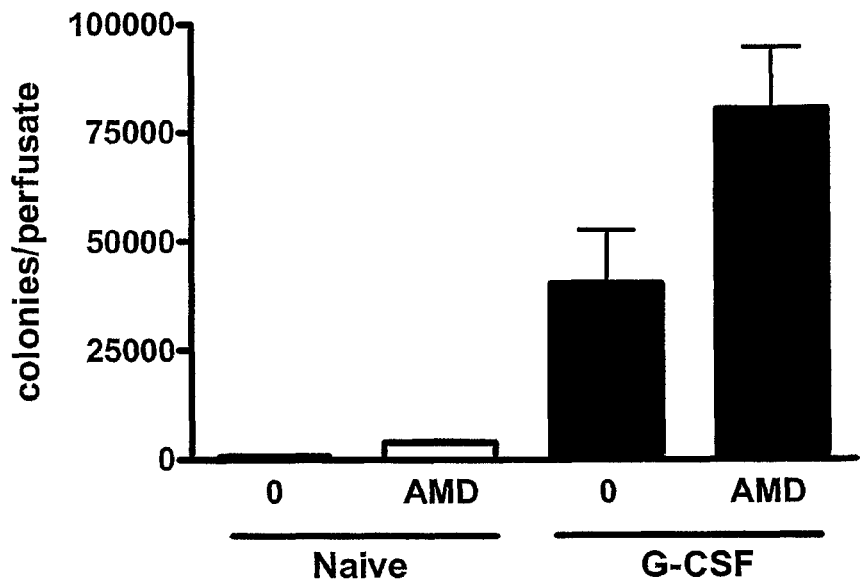
FIGS. 1 and 2 show the effect of G-CSF pre-treatment on the mobilization of HPCs from the bone marrow. Consistent with previous data published by us and others G-CSF acts synergistically with AMD3100 to mobilize HPCs.
Figure 2:
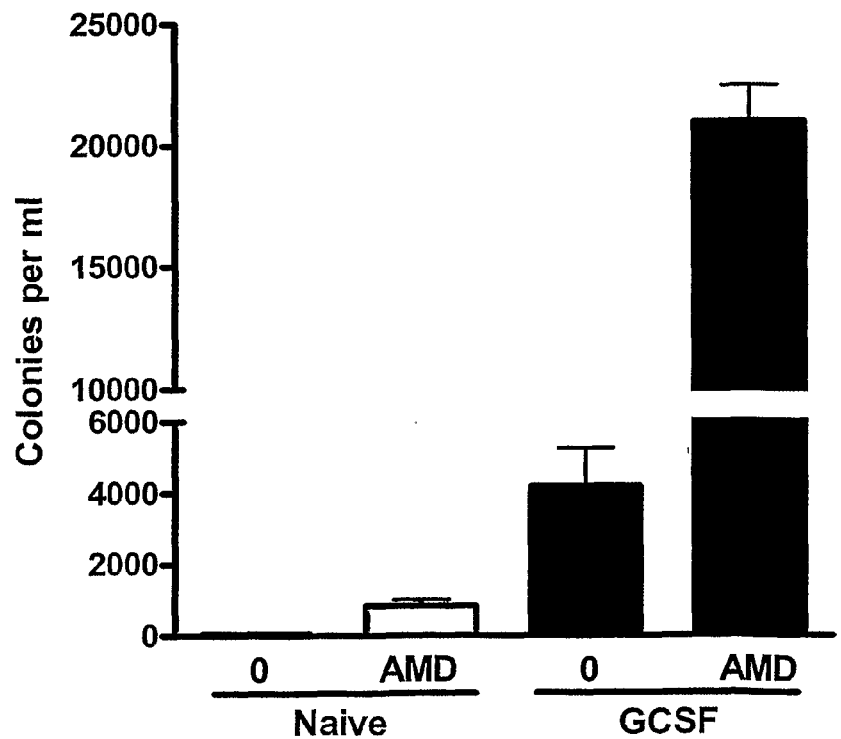
Figure 3:
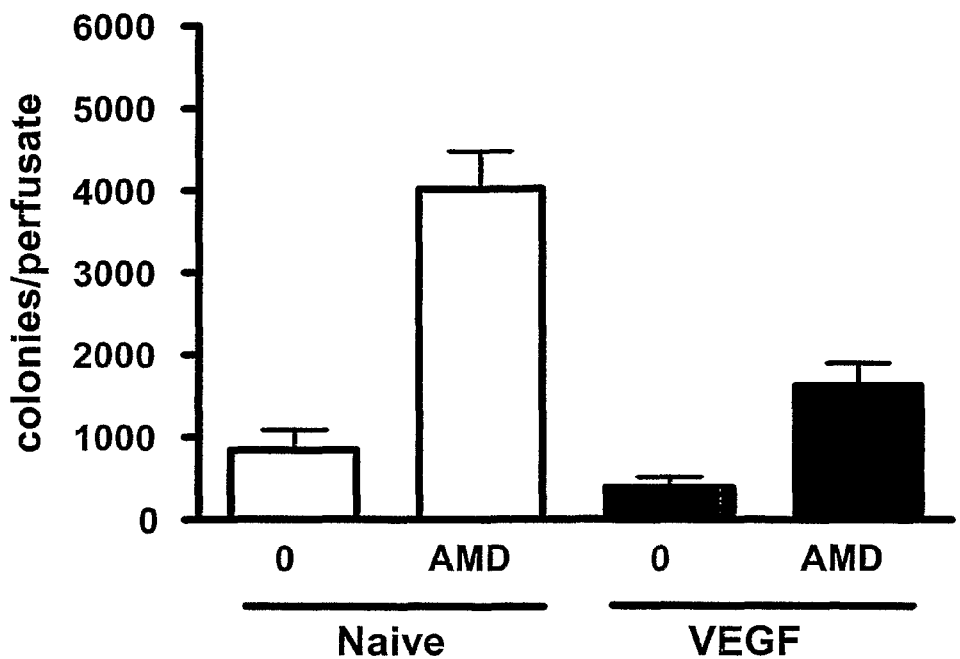
FIGS. 3 and 4 show that in contrast to G-CSF, pre-treatment with VEGF actually inhibits the capacity for AMD3100 to mobilize HPCs.
Figure 4:
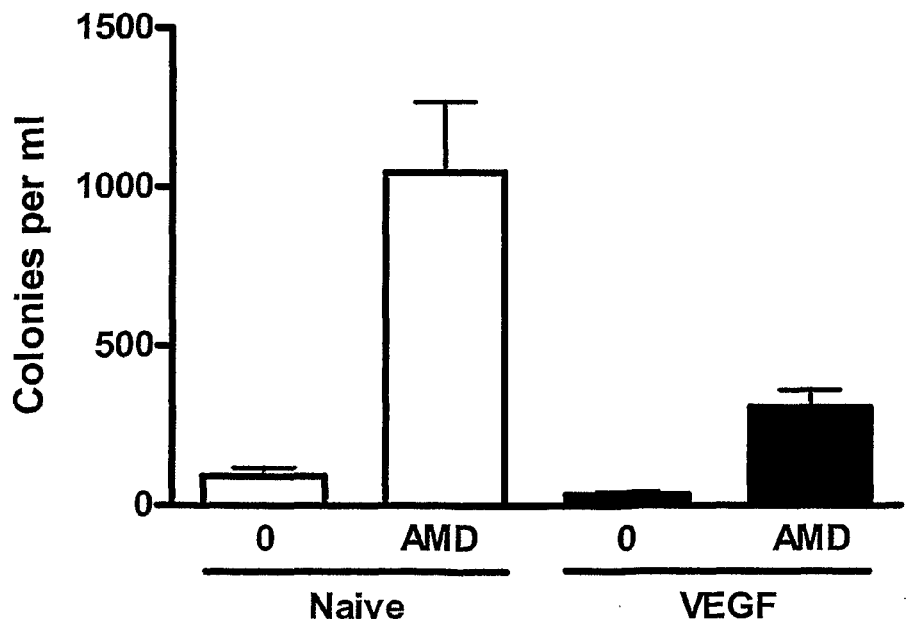

Interestingly, comparing FIGS. 3 and 5, AMD3100 mobilises about 4000 HPCs in FIG. 3 versus 400 EPCs in FIG. 5. This reflects the difference in the frequency of these two types of stem cells within the bone marrow.

Figure 7:
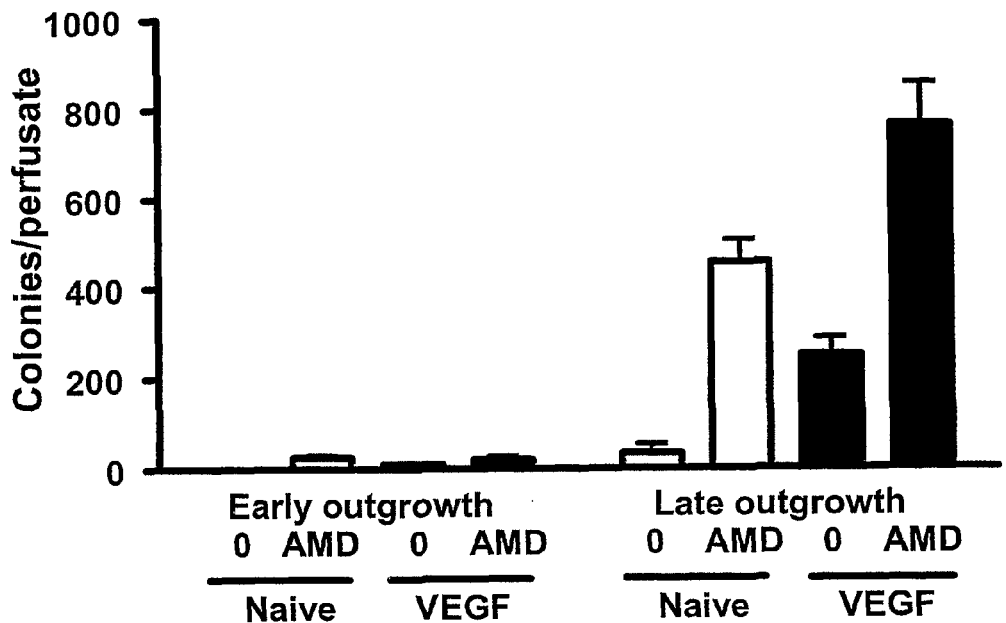
Figure 8:
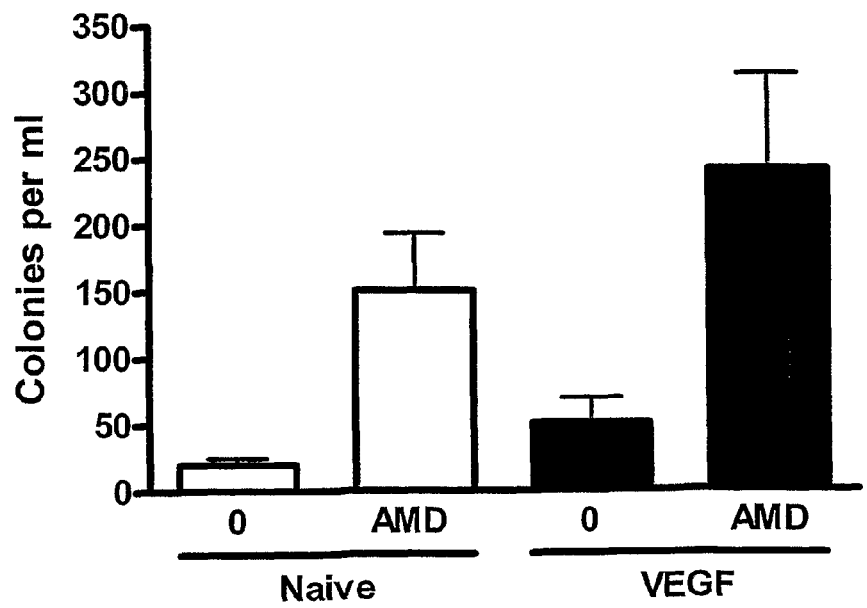

FIGS. 7 and 8 show that there is an additive effect of AMD3100 and VEGF with respect to EPC mobilization. Maximal mobilization of EPCs is seen with the combination of VEGF pre-treatment and AMD3100 acute administration.

Mesenchymal Stem Cells (MSC)

Figure 9:
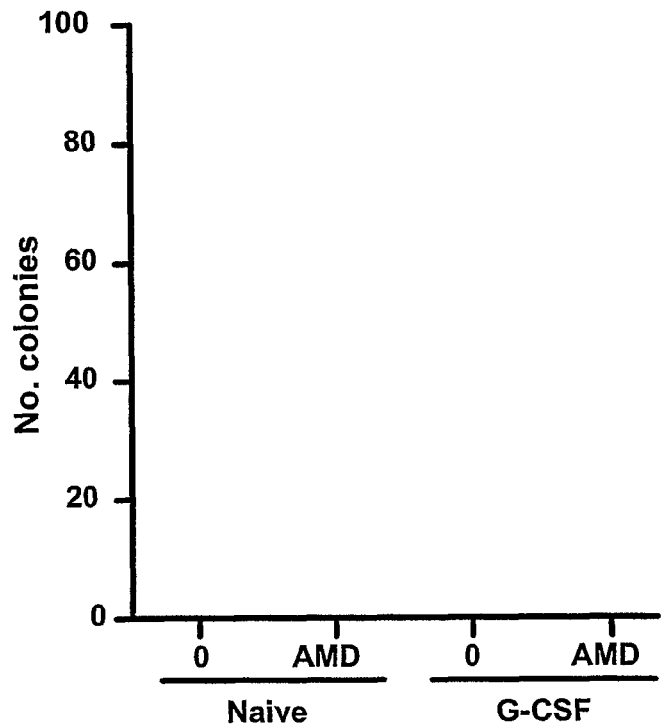
Figure 10:
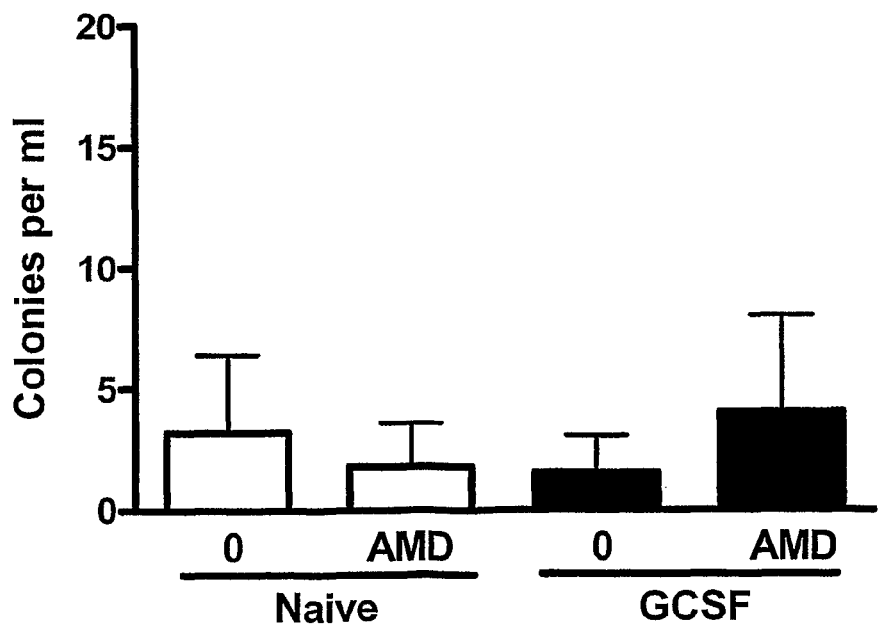

FIGS. 9 and 10 show that AMD3100 alone does not mobilize MSCs. G-CSF alone or in combination with AMD3100 does not mobilize MSCs.

Figure 11:
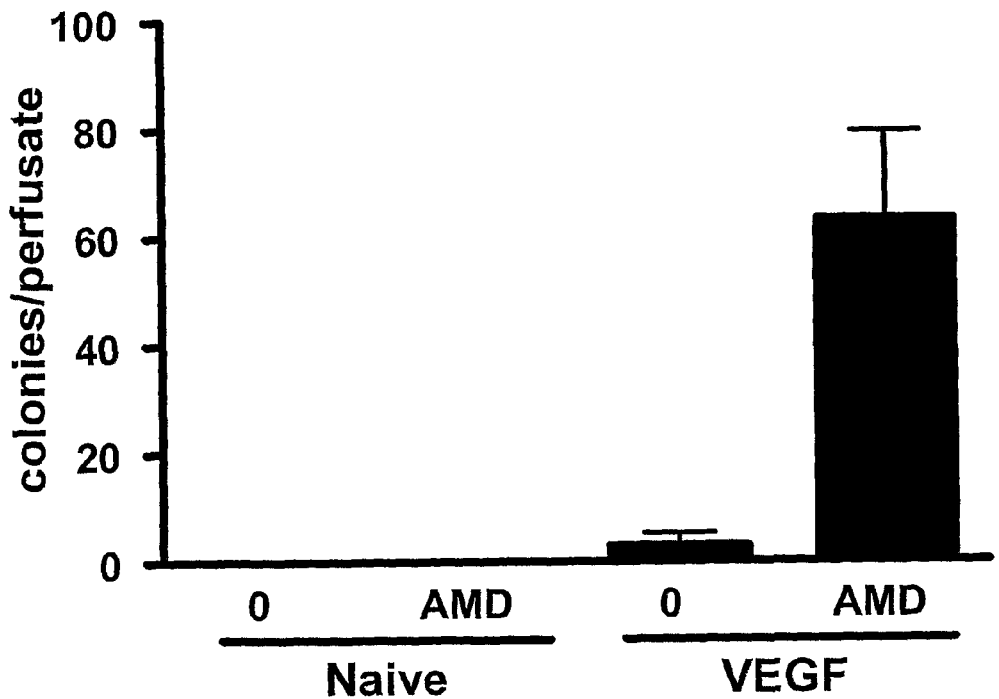
Figure 12:
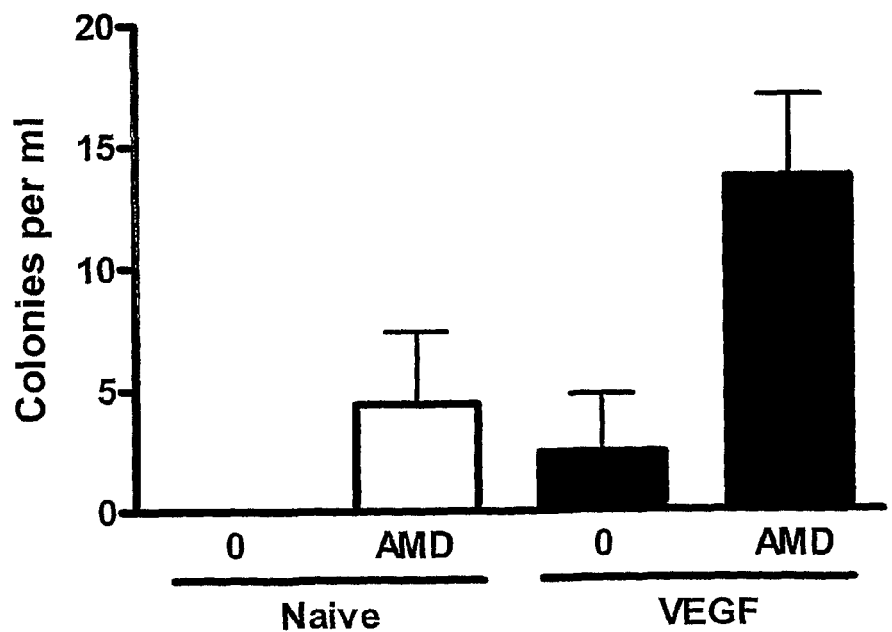
Figure 13:
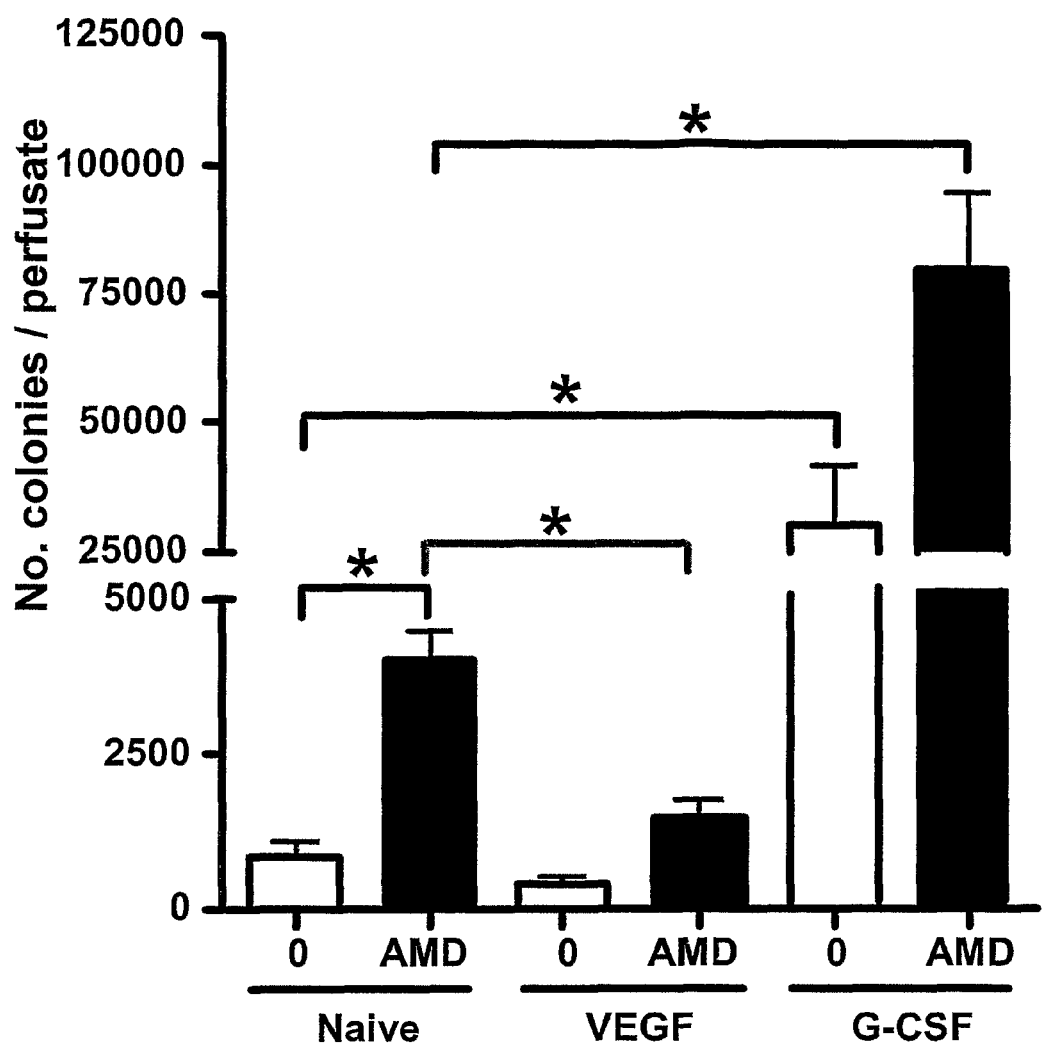
Figure 14:
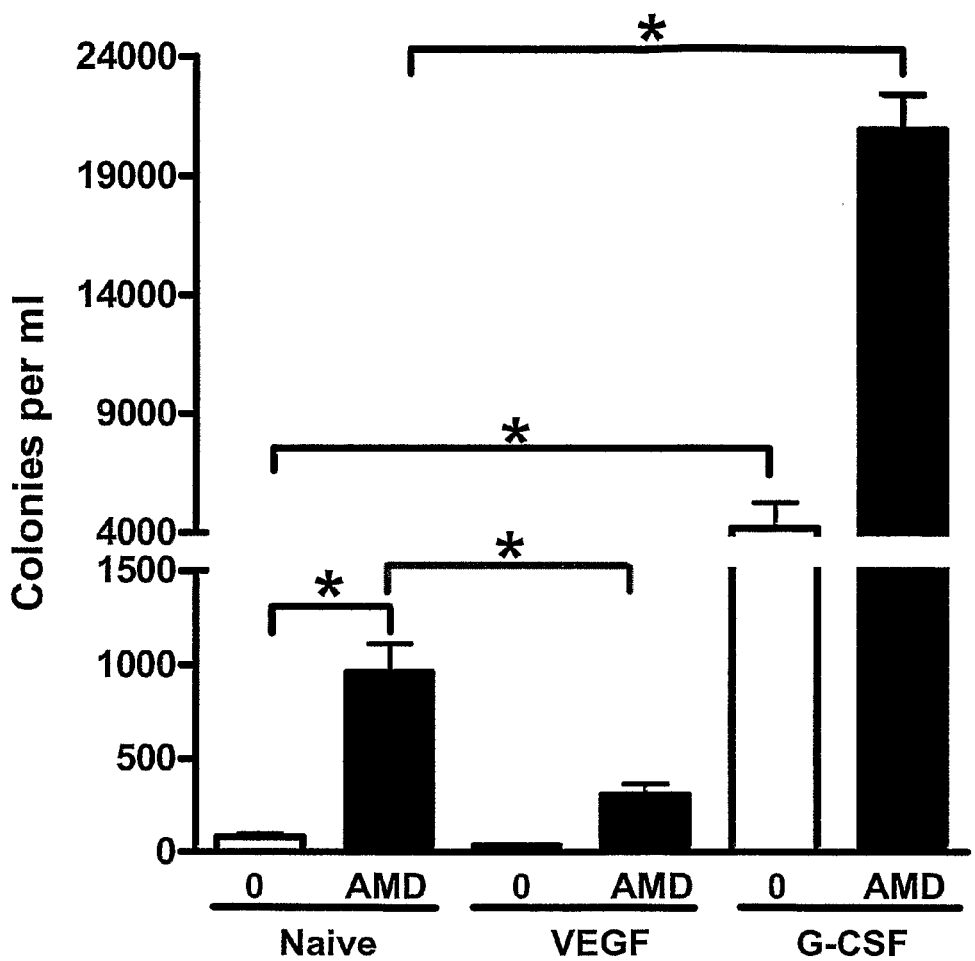
Figure 15:
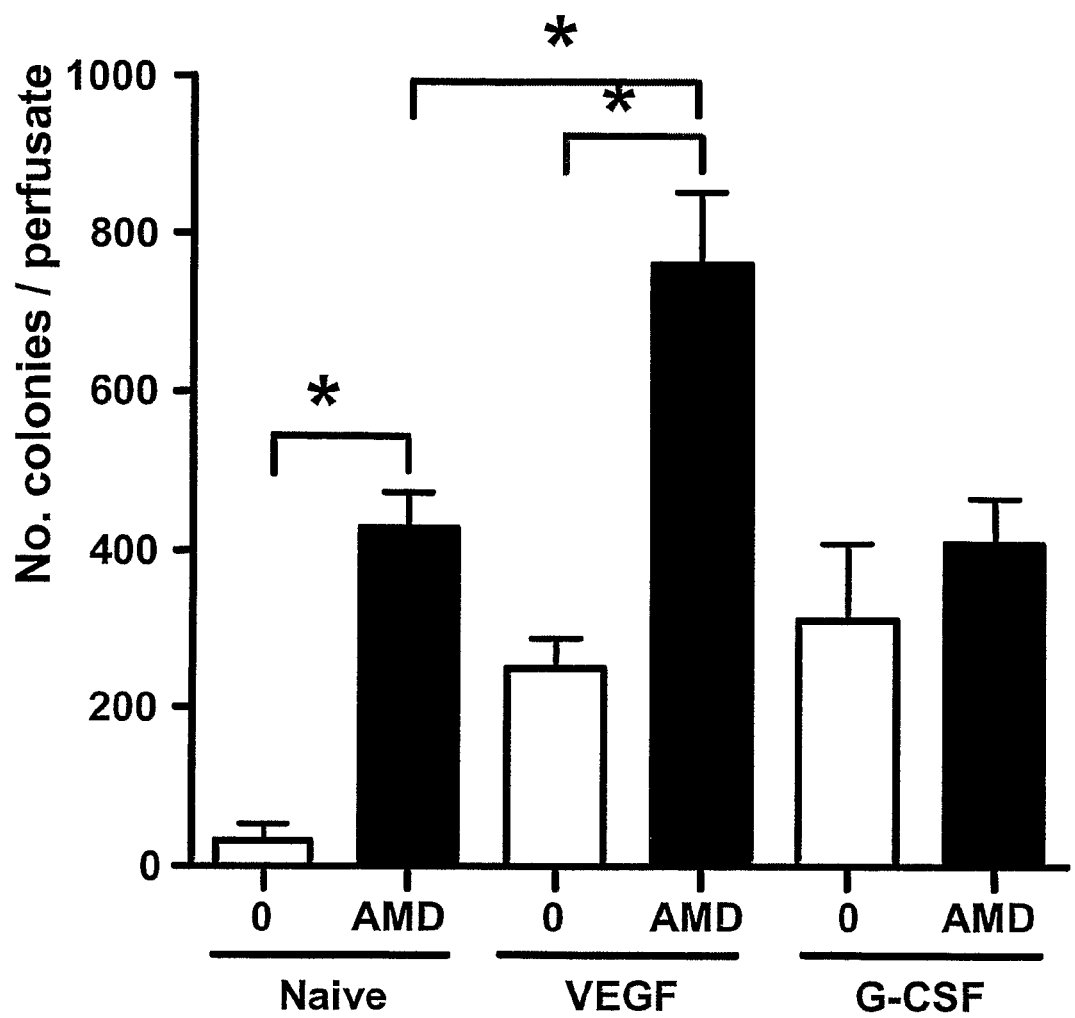
Figure 16:
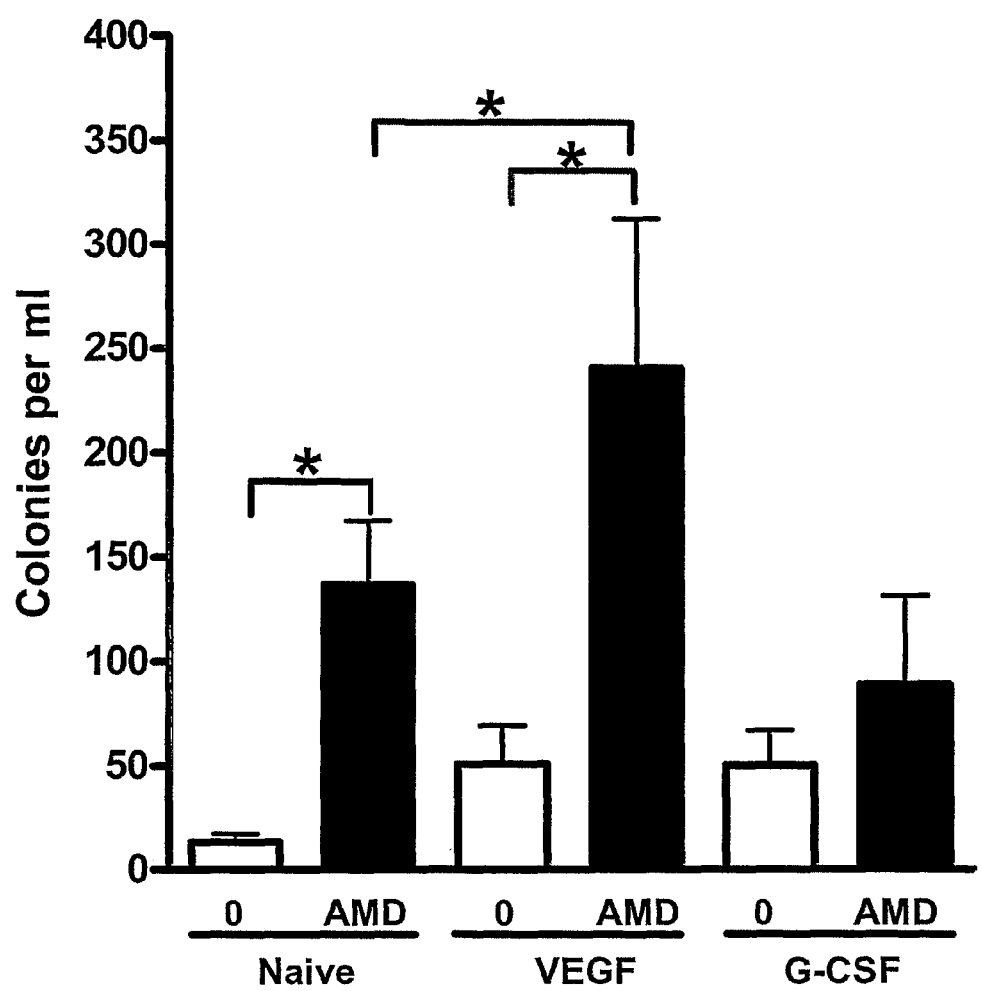
Figure 17:
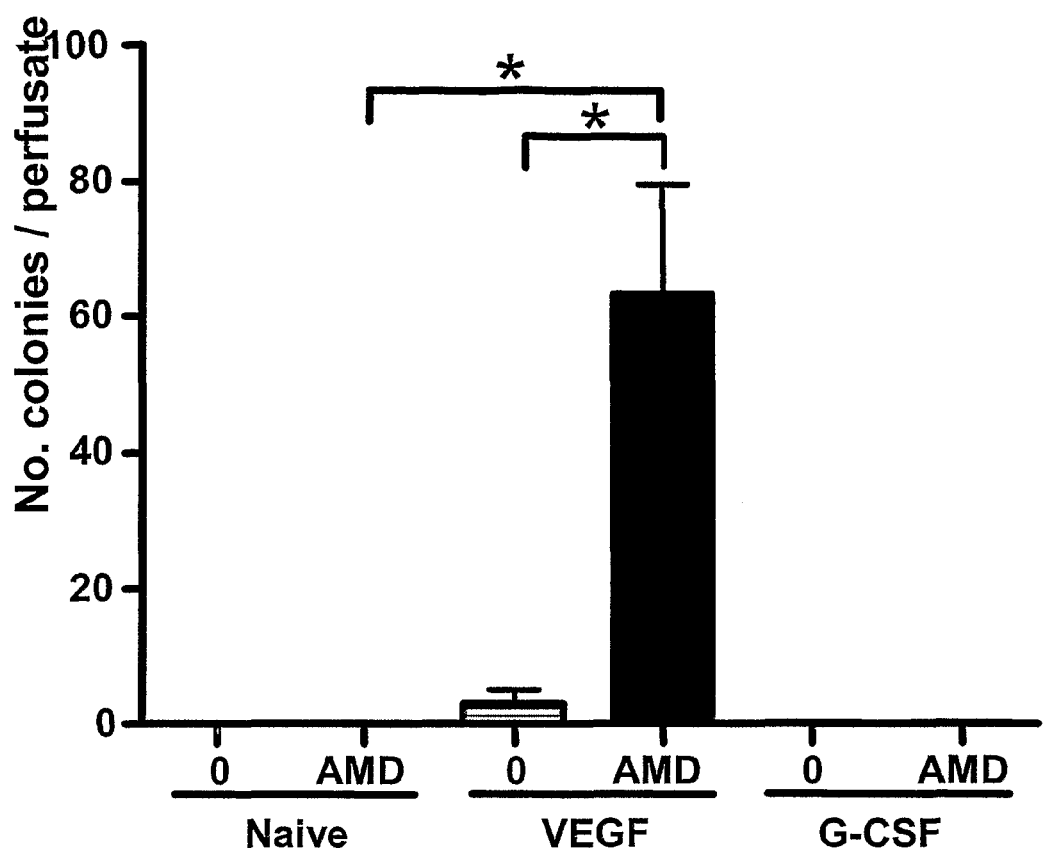
Figure 18:
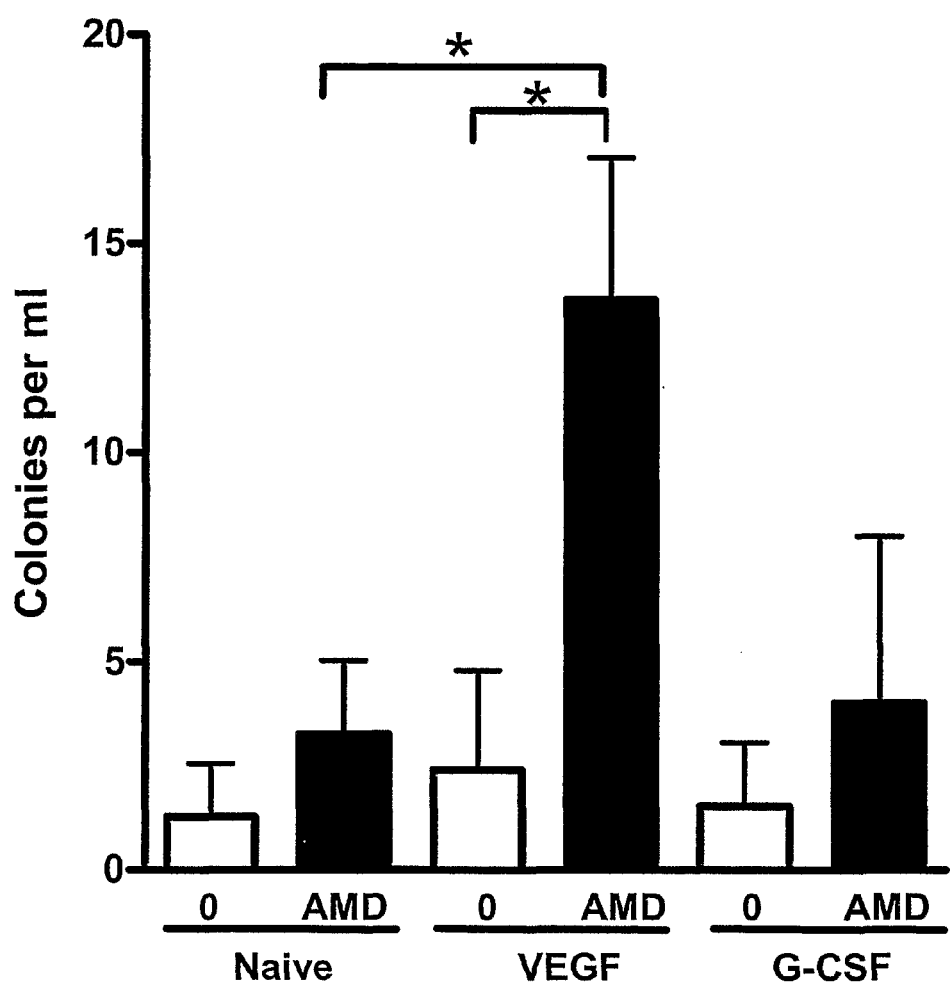
Figure 19:
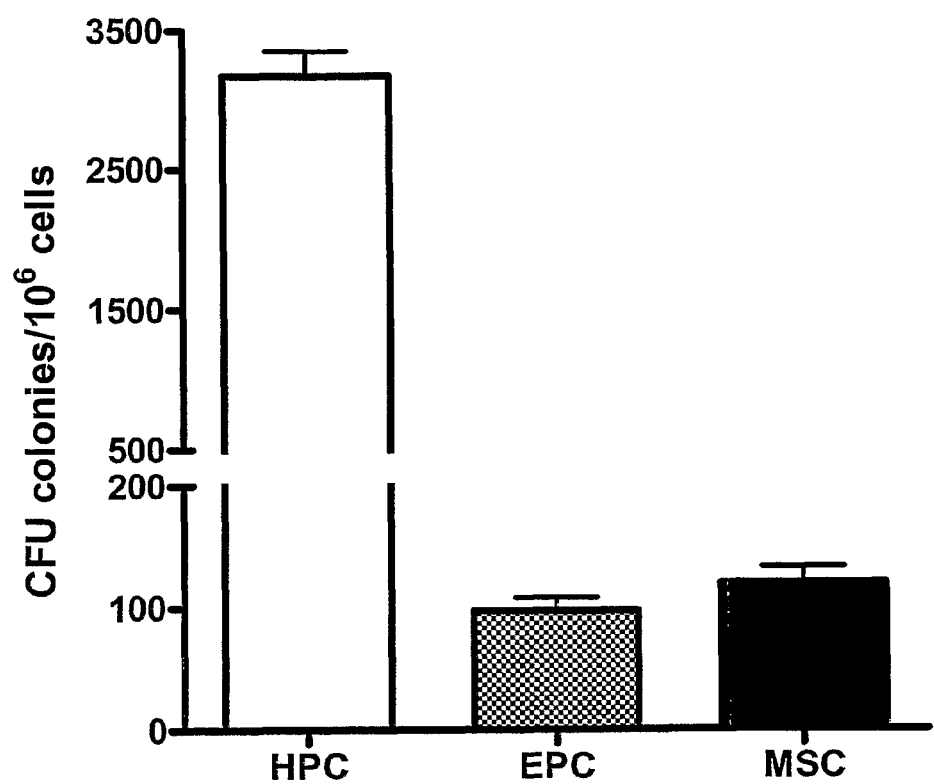
FIG. 19 shows the relative frequency of HPCs, EPCs and MSCs in the bone marrow. The ratio of HPCs:EPCs:MSCs in the bone marrow is 30:1:1.

FIGS. 11 and 12 show that VEGF alone does not mobilize MSCs. VEGF pre-treatment in combination with AMD3100 mobilizes MSC into the blood.

The combined data are represented in FIGS. 13 to 18. This enables comparisons to be made between the effects of G-CSF/AMD3100 compared with VEGF/AMD3100. FIGS. 13 to 18 do not combine the different methods of measuring the mobilisation of the stem cells (bone marrow perfusion versus in vivo), they combine the results obtained with the same techniques.

EXAMPLE 2

A patient in need of mobilisation of MSCs or ESCs in order to repair injured tissue may be administered VEGF daily subcutaneously for 3-5 days, followed by administration subcutaneously of a single dose of a CXCR4 antagonist such as AMD3100. The mobilised cells can be harvested and then returned to the site of injury in the patient or can be allowed naturally to home to the site of injury.

EXAMPLE 3

Differential Mobilization of Subsets of Progenitor Cells from the Bone Marrow

Introduction

The bone marrow is a reservoir of progenitor cells, including haematopoietic progenitor cells (HPCs), fibrocytes, mesenchymal stem cells (MSCs) and endothelial progenitor cells (EPCs). In response to disease or tissue injury these cells are mobilized from the bone marrow and recruited into tissues where they contribute either to disease progression or tissue repair (Takahashi et al., 1999; Orlic et al., 2001; Rankin 2008). Thus, for example, fibrocyte recruitment detrimentally contributes to fibrosis and tissue remodelling in diseases such as idiopathic lung fibrosis and ischemic cardiomyopathy (Philips et al., 2004; Haudek et al., 2006). In contrast, EPCs recruited into ischemic tissues promote angiogenesis and thereby contribute to tissue regeneration (Asahara et al., 1997; 1999; Takahashi et al., 1999; Nolan et al., 2008). Further, the identity of an EPC type, which is distinct from a HPC phenotype has now been reported (Hur et al., 2004; Yoder et al., 2007; Nolan et al., 2007) Indeed, EPCs have been demonstrated to repair damaged myocardium and improve cardiac function (Kocker et al., 2001). Mesenchymal stem cells have the capacity to differentiate into adipocytes, chondrocytes and osteocytes and potentially other cell types including epithelial, myocardial or neuronal cells (Pittenger et al., 1999). It is thought, therefore, that MSCs may be used to promote tissue regeneration in the treatment of diseases such as osteogenesis imperfecta and Parkinsons (Hess & Borlongan 2008; Bielby et al., 2007). Additionally MSCs have been reported to have immunosuppressive properties and as such they may be therapeutically useful for the treatment of autoimmune diseases (Le Blanc & Ringden 2007). The therapeutic application of these distinct sub-populations of stem cells in the context of specific diseases is therefore widely anticipated. Currently however, there are both practical and technical complications associated with harvesting, isolation, ex vivo expansion and delivery of these cells. An alternative strategy for stem cell therapy is to stimulate the mobilization of stem cells from the bone marrow into the circulation, thereby circumventing these issues. This approach has been established clinically with respect to the treatment of donors over 3-5 days with the cytokine G-CSF to mobilize of HPCs for bone marrow transplants (BMT) (Cashen et al., 2004).

Mobilization of progenitor cells is a multi-stage process; with initial release from their bone marrow niche followed by active migration across the bone marrow sinusoidal endothelium. The chemokine axis SDF-1α/CXCR4 is critically involved in the retention of haematopoietic stem cells within the bone marrow (Levesque et al., 2003). At a molecular level, G-CSF has been shown to act by disrupting the SDF-1α/CXCR4 retention axis, both by reducing CXCR4 expression on HPCs and levels of SDF-1α in the bone marrow (Levesque et al., 2003; Semerad et al., 2002). This knowledge has led to the development of CXCR4 antagonists as HPC mobilizing agents. In contrast to G-CSF, such antagonists work acutely, mobilizing HPCs within an hour. Moreover, we and others have shown that chronic G-CSF therapy combined with acute administration of a CXCR4 antagonist synergistically enhances HPC mobilization from the bone marrow (Broxmeyer et al., 2005; Martin et al., 2006). This combination therapy has recently shown greater efficacy compared to G-CSF alone in phase III clinical trials for BMT (Calandra et al., 2008). While it has been shown that administration of a CXCR4 antagonist alone increases the circulating numbers of EPCs and improves tissue perfusion following ischemia in animals (Capoccia et al., 2006; Shepherd et al., 2006) it is not known whether G-CSF therapy in combination with acute administration of the CXCR4 antagonist acts synergistically to mobilize EPCs.

In addition to factors that disrupt the retention of EPCs in the bone marrow, EPCs may also be mobilized by factors, such as VEGF, that stimulate their migration (Asahara et al., 1997). Indeed treatment of mice with VEGF has been shown to increase the circulating numbers of EPCs (Asahara et al., 1999), however, the relative efficacy of VEGF versus G-CSF alone or in combination with other mobilizing reagents has not been specifically assessed with respect to EPC mobilization. There is evidence that bone marrow-derived MSCs contribute to tissue regeneration, suggesting that these cells are also mobilized in response to tissue injury, however the factors and mechanisms regulating the mobilization of MSCs are currently unknown (Rochefort et al., 2006; Au et al., 2008).

We have previously shown that different sub-populations of leukocytes are selectively mobilized from the bone marrow in response to specific blood-borne mediators via distinct mechanisms (Palframan et al., 1998; 1998a; Martin et al., 2003; Wengner et al., 2008). In this study we have identified pathways regulating the differential mobilisation of discrete populations of progenitor cells.

Results

The CXCR4 Antagonist Mobilizes Discrete Populations of Progenitor Cells in Mice Pre-Treated with G-CSF or VEGF.

Figure 20:
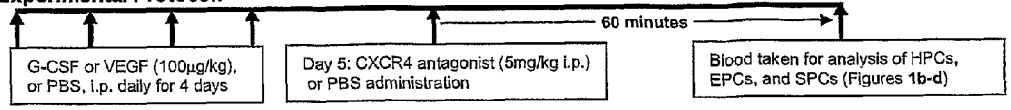
Figure 20:
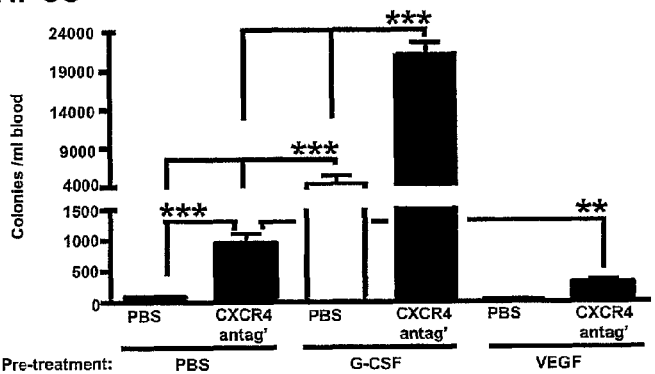
Figure 20:
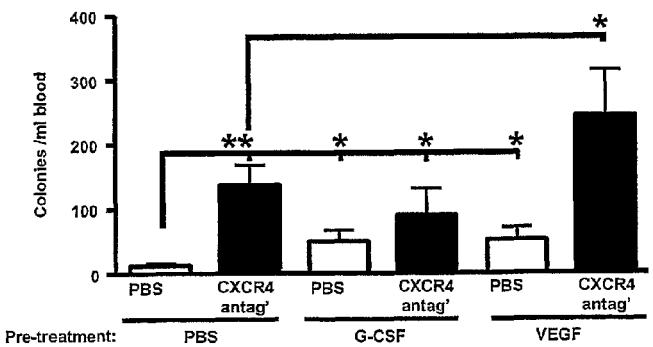
Figure 20:
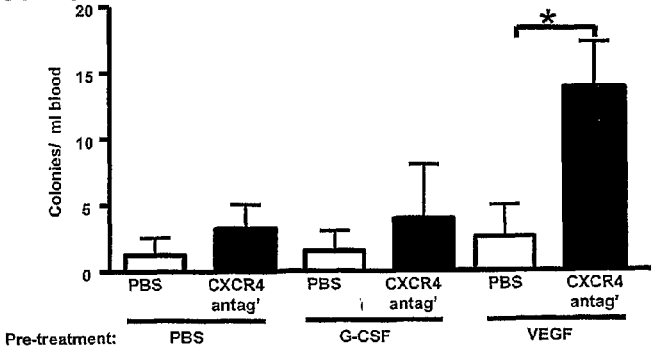
Figure 27:
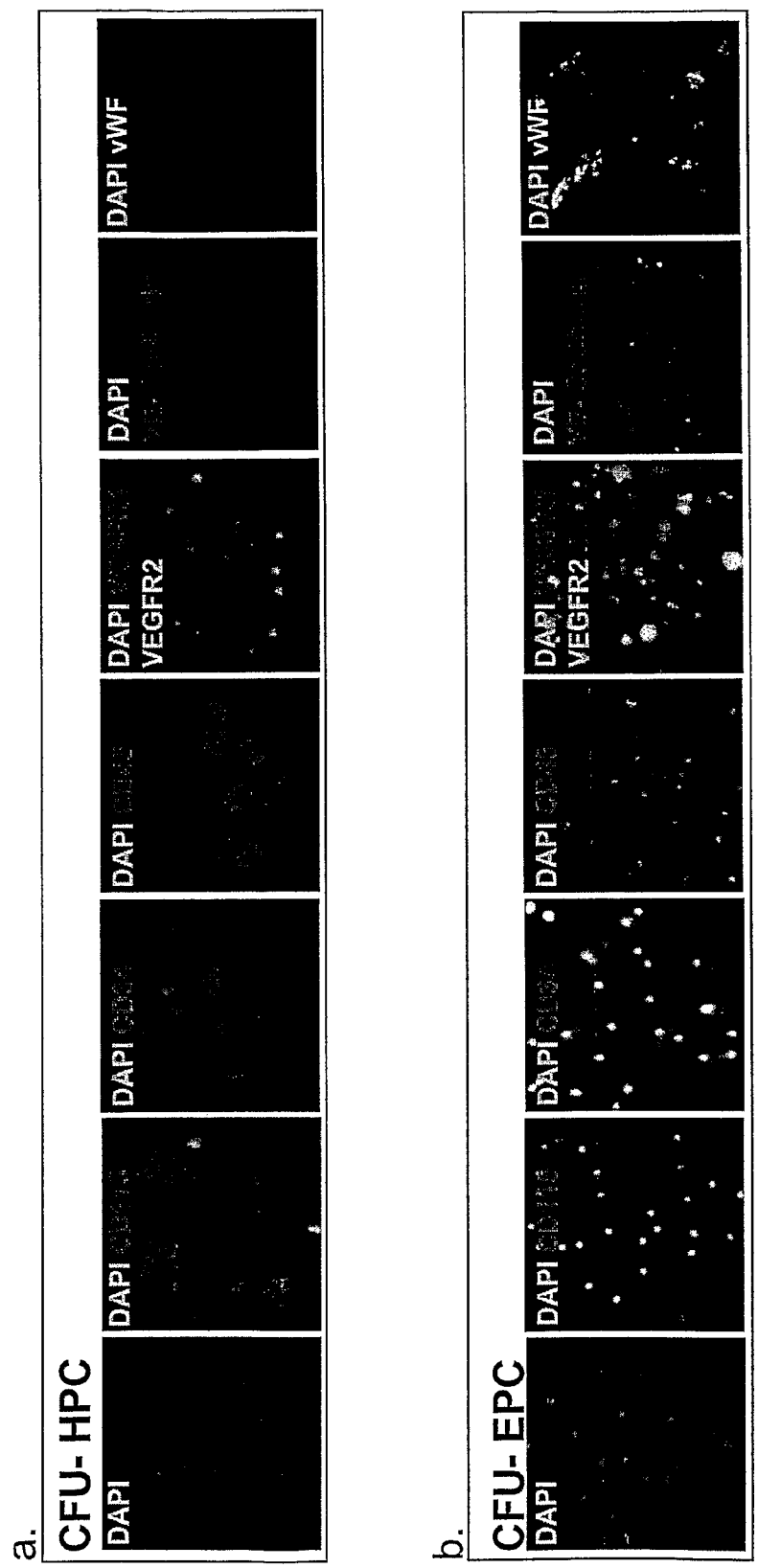
Figure 28:
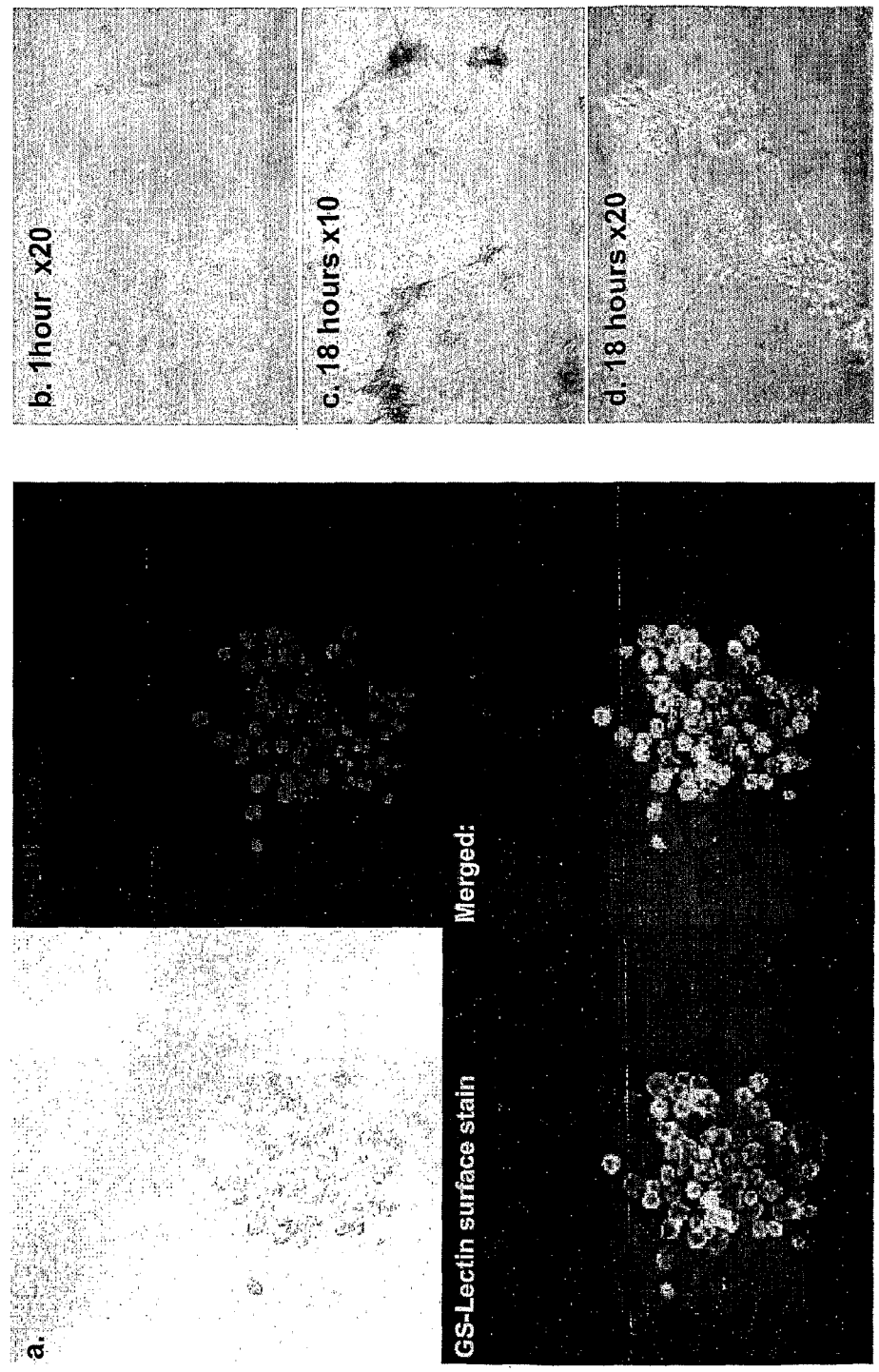
Figure 29:
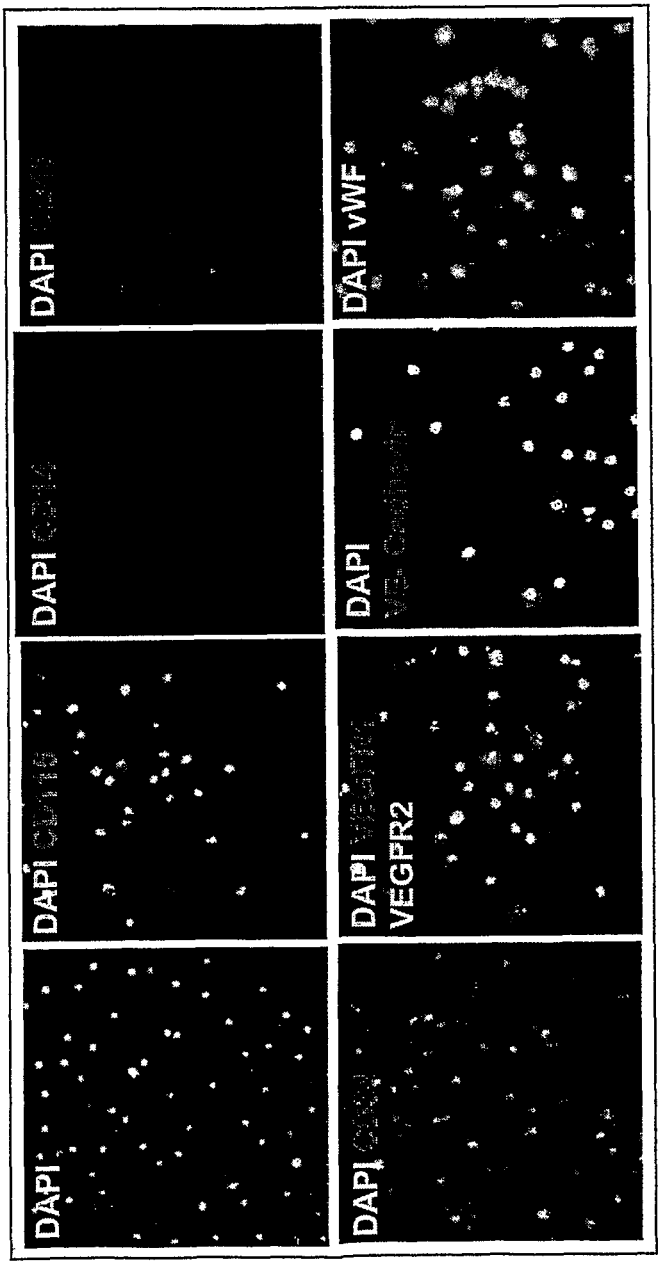

It has previously been established that G-CSF and the CXCR4 antagonist act synergistically to mobilize HPCs from the bone marrow (Broxmeyer et al., 2005; Martin et al 2006). In the first experiment we examined whether this treatment protocol similarly mobilized maximal numbers of EPCs and stomal progenitor cells (SPCs). Furthermore we investigated whether the profile and numbers of progenitors in the blood changed if mice were pre-treated with VEGF instead of G-CSF. We determined circulating numbers of HPCs, EPCs and SPCs one hour after the administration of the CXCR4 antagonist, AMD3100, to mice pre-treated over 4 days with either G-CSF, VEGF or vehicle control. Administration of the CXCR4 antagonist alone increased circulating numbers of HPCs and EPCs within 1 hour (FIGS. 20b and 20c, and Shepherd et al., 2006). Interestingly, SPCs were not detected in the blood. G-CSF pre-treatment of mice also increased circulating numbers of HPCs, and to a lesser extent EPCs. (FIGS. 20b and 20c). Intriguingly, no SPCs were detected (FIG. 20d). Whilst G-CSF pre-treatment followed by acute administration of the CXCR4 antagonist synergistically enhanced circulating numbers of HPCs (FIG. 20b and Broxmeyer et al., 2005; Martin et al 2006), no such synergism (or even additive effect) was apparent for EPC mobilization (FIG. 20c). Furthermore, SPCs could not be detected. Of note, EPCs were scored after 21 days in culture and were shown to be CD34, VEGFR2, VE-Cadherin, and vWF positive (FIGS. 27, 28 and 29). Furthermore these EPCs stained positively with GS-lectin, took up acetyl-LDL and formed tubules in vitro. These EPCs are therefore equivalent to the so-called late outgrowth EPCs that have the capacity to form vessels in vivo (Hur et al., 2004; Yoder et al., 2007; Nolan et al., 2007; Hirschi et al., 2008). Importantly the mobilized EPCs did not express CD115, CD14, or CD45 and are thus distinct from both HPCs and the EPCs that are of monocytic origin (FIGS. 27, 28 and 29) (Hur et al., 2004; Yoder et al., 2007; Nolan et al., 2007; Hirschi et al., 2008)

Figure 30:
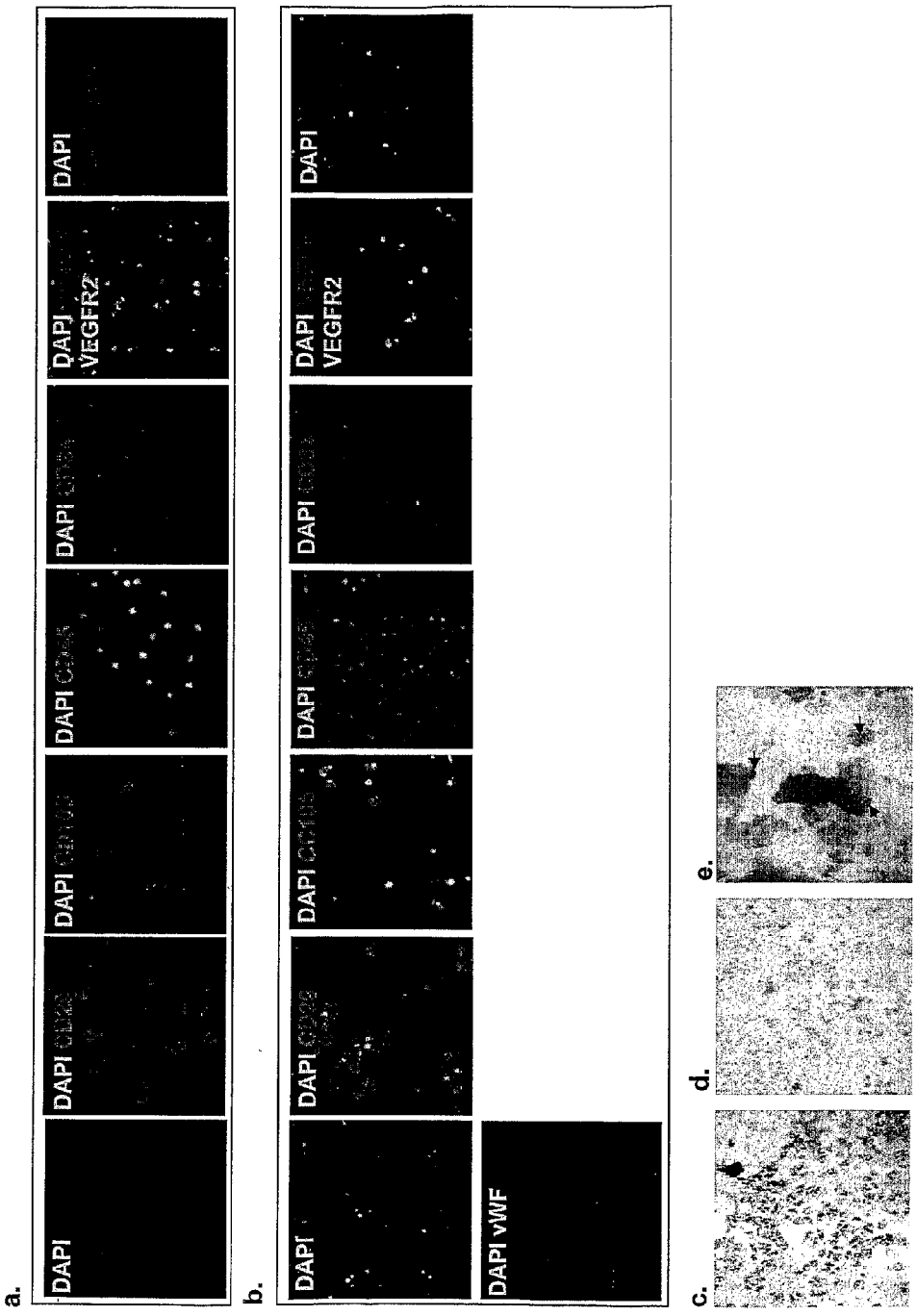

VEGF administration can increase circulating number of cells with an EPC phenotype (Asahara et al., 1997). Similarly we observed an increase in EPC numbers following VEGF treatment of mice over 4 days (FIG. 20c). Moreover, a more than additive increase in EPC numbers was observed when the CXCR4 antagonist was administered acutely to mice pre-treated with VEGF as compared to mice treated with VEGF alone or administered a CXCR4 antagonist alone ($P<0.05$ FIG. 20c). In contrast to G-CSF, VEGF-treatment did not increase circulating numbers of HPCs (FIG. 20b). Further, we found unexpectedly that VEGF pre-treatment profoundly suppressed circulating numbers of HPCs (77% reduction) mobilized by the CXCR4 antagonist ($P<0.01$, FIG. 20b). Uniquely, VEGF-treatment combined with the CXCR4 antagonist led to a significant increase in circulating SPCs (CFU-F $P<0.001$, FIG. 20d). Importantly, mobilized SPCs displayed the same antigen expression phenotype as bone marrow-derived SPCs (FIG. 30a) which on expansion exhibited tri-lineage differentiation potential (FIG. 30c-e). Mobilized SPCs were plastic adherent cells, shown to be CD29 and CD105, positive; yet were CD34 and CD45 negative (FIG. 30b). Mobilized SPCs had the same characteristics as murine mesenchymal stem cells (Phinney et al., 1999; Pittenger et al., 1999; Mereilles & Nardi 2003). Mobilized SPCs were also negative for VE-Cadherin and vWF and were therefore distinct from mobilized EPCs (FIG. 30b). These results suggest that fundamentally different mechanisms regulate the mobilization of phenotypically distinct HPCs, EPCs and SPCs.

Figure 21:
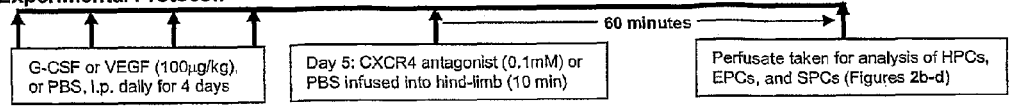
Figure 21:
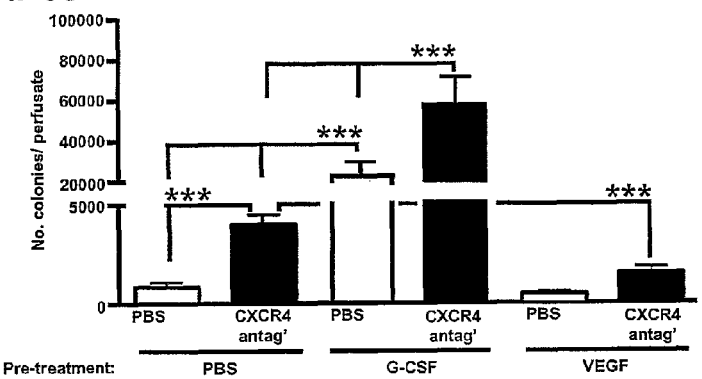
Figure 21:
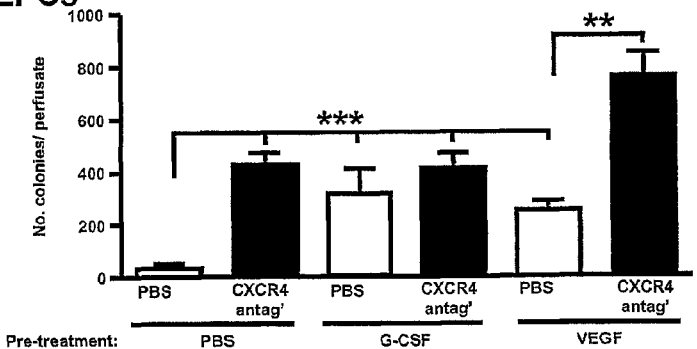
Figure 21:
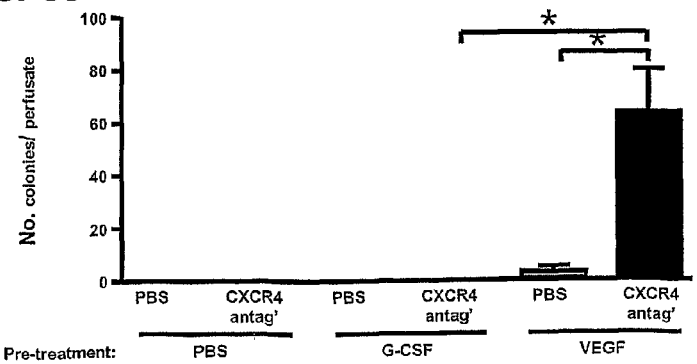

G-CSF and VEGF Pre-Treatment Differentially Regulate the Rate of Egress of Progenitor Cell Sub Populations from the Bone Marrow in Response to a CXCR4 Antagonist To determine whether the differences in circulating numbers of progenitors cells was due specifically to differences in their rate of egress out of the bone marrow we used an in situ perfusion model of the murine hind-limb developed by our group to directly assess mobilization. In this system, the femoral artery and vein are cannulated in situ such that the femur and tibia bone marrow are perfused in isolation. Mobilized cells are then collected via the femoral vein (Martin et al., 2003; 2006; Wengner et al., 2008). This technique allows direct comparisons of the number of cells mobilized over a defined period of time, without the complications of progenitor cell trafficking into other tissues including their return to the bone marrow. Mice were pre-treated with vehicle, G-CSF or VEGF for 4 days. On day 5, the femoral artery was infused for 10 minutes with either vehicle or the CXCR4 antagonist and cells mobilized were collected over a period of 1 hour (FIG. 21a: experimental protocol). When the CXCR4 antagonist was infused into vehicle pre-treated mice, HPCs and EPCs, but not SPCs were mobilized from the bone marrow ($P<0.001$, FIG. 21b-21d). Pre-treatment of mice with G-CSF over 4 days enhanced the basal rate of HPC and EPC egress from the bone marrow ($P<0.001$, FIGS. 21b and 21c). However, G-CSF pre-treatment did not lead to the mobilization of SPCs (FIG. 21d). As indicated above, G-CSF pre-treatment followed by the CXCR4 antagonist led to a synergistic mobilization of HPCs ($P<0.001$, FIG. 21b), but not EPCs (FIG. 21c). Furthermore, no SPCs were mobilized with the combination of G-CSF pre-treatment followed by the CXCR4 antagonist (FIG. 21d). VEGF pre-treatment resulted in significant EPC mobilization ($P<0.001$, FIG. 21c), however, HPCs and SPCs were not mobilized (FIGS. 21b and 21d). Furthermore, VEGF pre-treatment almost completely suppressed HPC mobilization induced by infusion of the CXCR4 antagonist ($P<0.001$ FIG. 20e, 75% reduction), whilst an additive effect was observed for EPC mobilization ($P<0.01$ FIG. 21c). Uniquely with this treatment regime, SPCs were mobilized ($P<0.001$, FIG. 21d). These experiments definitively show that changes in circulating numbers of progenitors are due to changes in their rate of egress from the bone marrow.

Acute Administration of Cytokines does not Result in the Differential Mobilization of HPCs, EPCs and SPCs in Response to the CXCR4 Antagonist.

Figure 31:
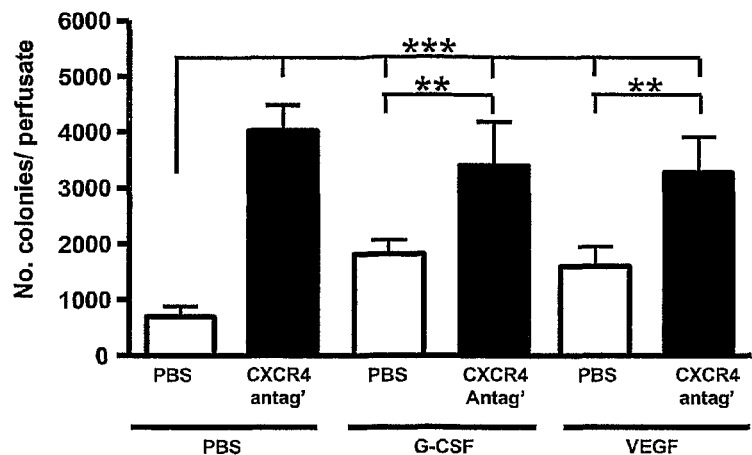
Figure 31:
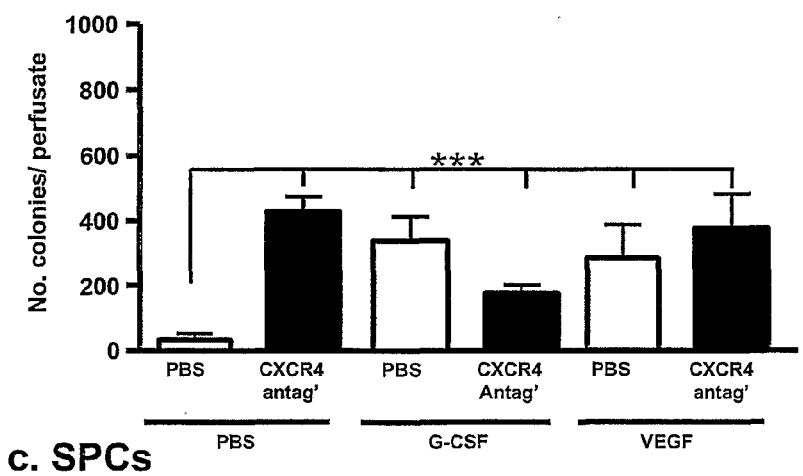
Figure 31:
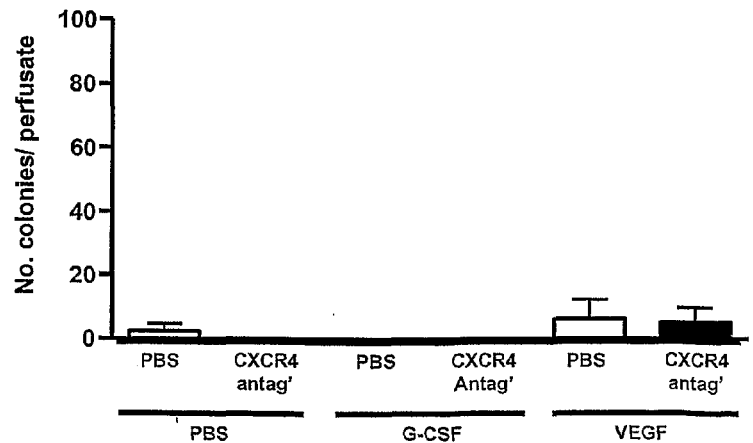

The selective mobilization of EPCs and SPCs achieved by treating mice over 4 days with VEGF followed by administration of the CXCR4 antagonist was not reproduced when mice were treated acutely with a combination of VEGF and the CXCR4 antagonist. Infusion of either G-CSF or VEGF directly into the femoral artery for 10 minutes and collection up to 60 minutes mobilized both HPCs and EPCs ($P<0.001$ FIGS. 31a and 31b). However, acute administration of VEGF (in contrast to VEGF pre-treatment over 4 days) did not inhibit the mobilization of HPCs with a CXCR4 antagonist and acute administration of G-CSF did not act synergistically with the CXCR4 antagonist to mobilize HPCs (FIGS. 31a and 31b). Further, neither growth factor, when administered acutely or in combination with the CXCR4 antagonist led to mobilization of SPCs (FIG. 31c). This suggested that the ability of G-CSF and VEGF to promote the differential mobilization of progenitor cell subsets is dependent on changes to the bone marrow environment or the progenitor cell phenotype that occurs over a number of days.

VEGF-Treatment does not Alter Bone Marrow Morphology or Progenitor Cell Frequency We next determined whether treatment of mice over 4 days with VEGF or G-CSF affected the number of progenitor cells in the bone marrow. The total number of cells in the femurs of mice treated with VEGF ($1.07\pm0.11\times10^7$ cells/femur) or G-CSF ($1.41\pm0.28\times10^7$ cells/femur) was not significantly different compared to control mice ($1.19\pm0.07\times10^7$ cells/femur). Furthermore, no difference was observed in the frequency of HPCs (FIG. 22a), EPCs (FIG. 22b) or SPCs (FIG. 22c) in the bone marrow of VEGF-treated mice compared to controls. However, G-CSF-treatment did cause a significant reduction in the number of bone marrow EPCs ($P<0.001$ FIG. 22b), and an increase in the number of SPCs ($P<0.05$ FIG. 3c).

Figure 22:
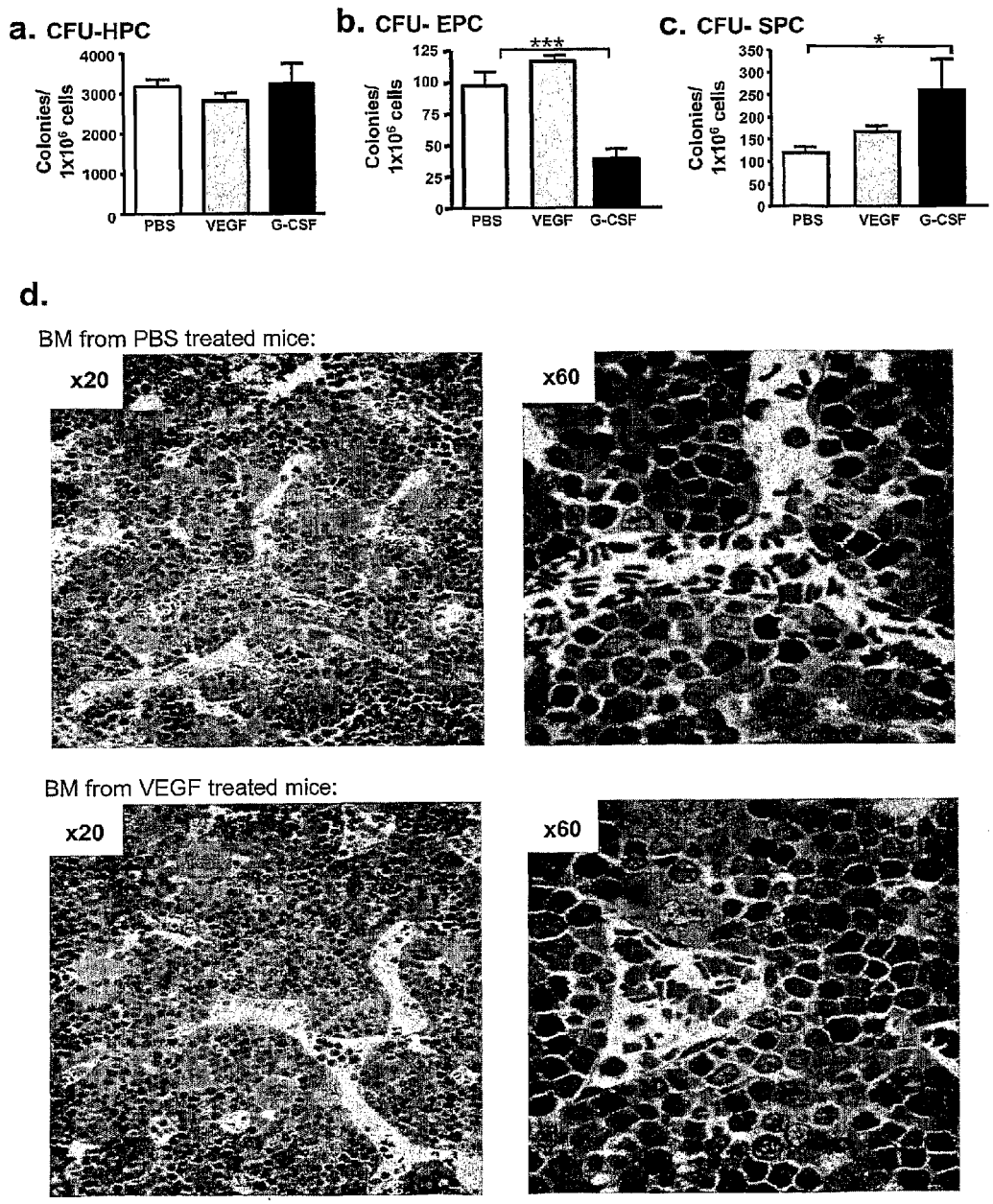

To determine whether VEGF-treatment of mice affected the gross morphology of the bone marrow, we performed histological analysis of bone marrow in mice treated over 4 days with PBS or VEGF. As shown in FIG. 22d we observed no differences in the gross morphology, the number of sinusoidal blood vessels, or endothelial integrity (FIG. 22d). Thus, with no gross morphological changes occurring to the bone marrow of mice treated with VEGF which might affect cellular egress, we next examined whether the molecular retention mechanisms had been disturbed.

VEGF-Treatment does not Alter the Expression of CXCR4 on HPCs or EPCs.

Figure 23:
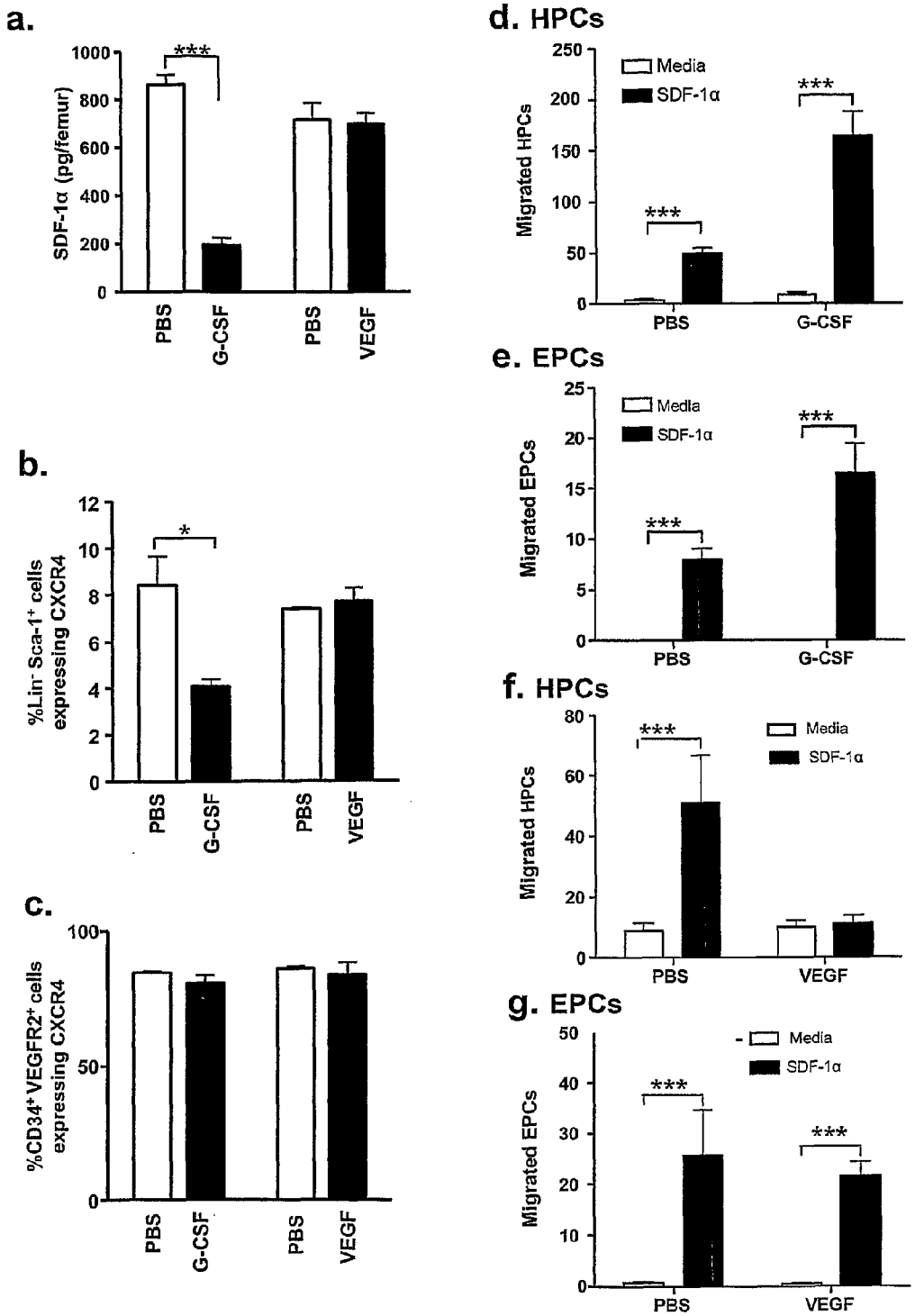

The CXCR4/SDF-1α chemokine axis is critical for the retention of HPCs in the bone marrow (Levesque et al., 2003). Indeed, G-CSF mobilizes HPCs by reducing their expression of CXCR4 and decreasing levels of SDF-1α in the bone marrow. To determine whether VEGF similarly mobilized progenitor cells by disrupting this chemokine axis, we analyzed CXCR4 expression on progenitor cells and SDF-1α levels in the bone marrow of VEGF and G-CSF-treated mice. In mice treated with G-CSF we observed a significant reduction in levels of SDF-1α ($P<0.001$, FIG. 23a) and CXCR4 expression on HPCs ($P<0.05$, FIG. 23b), however, the expression of CXCR4 on EPCs was unchanged (FIG. 23c), suggesting that G-CSF does not directly effect EPC retention. This explains why G-CSF is far more effective in mobilizing HPCs than EPCs (FIGS. 20b-20c and 21b-21c). In contrast, VEGF-treatment did not alter the expression of CXCR4 on either HPCs or EPCs (FIGS. 23b, and 23c). Moreover, SDF-1α levels in bone marrow supernatant following VEGF-treatment were not altered (FIG. 23a). Whilst the anti-CXCR4 antibody used here is targeted to the epitope matching the first 63 amino acids starting from the N-terminus of a GST-NCXCR4 fusion protein (Forster et al., 1998), it is noted that G-CSF will cleave part of this epitope, and therefore inhibiting the function of CXCR4 (Levesque et al., 2003). Thus reduced antibody binding will therefore indicate either a reduction in the expression of the functional receptor, or an absolute loss of the receptor. Thus we can conclude that VEGF-treatment does not inhibit the function of CXCR4 or affect its cell-surface expression.

These data indicate that VEGF-treatment does not disrupt the CXCR4/SDF-1α retention pathway and therefore explains why VEGF alone does not mobilize HPCs from the bone marrow.

VEGF-Treatment Inhibits HPC but not EPC Chemotaxis Towards SDF-1α.

Mobilization is dependent on cellular migration across the bone marrow sinusoidal endothelium. Given that VEGF did not alter CXCR4 expression on HPCs or EPCs (FIGS. 23b and 23c) we examined the ability of bone marrow derived HPCs and EPCs from G-CSF or VEGF-treated mice to undergo chemotaxis towards SDF-1α in vitro since in PBS-treated mice, both HPCs and EPCs migrated to SDF-1α ($P<0.001$ FIG. 23d-23g). G-CSF-treatment lead to further increased migration of HPCs and EPCs to SDF-1α ($P<0.001$ FIGS. 23d and 23e). In contrast, VEGF-treatment abolished the ability of HPCs to migrate to SDF-1α but had no effect on EPC migration (FIGS. 23f and 23g). The suppression of HPC chemotaxis towards SDF-1α suggested that HPCs from VEGF-treated mice were refractory to migratory stimuli despite expressing CXCR4.

VEGF-Treatment does not Affect the Ability of Neutrophils to Undergo Chemotaxis

Figure 24:
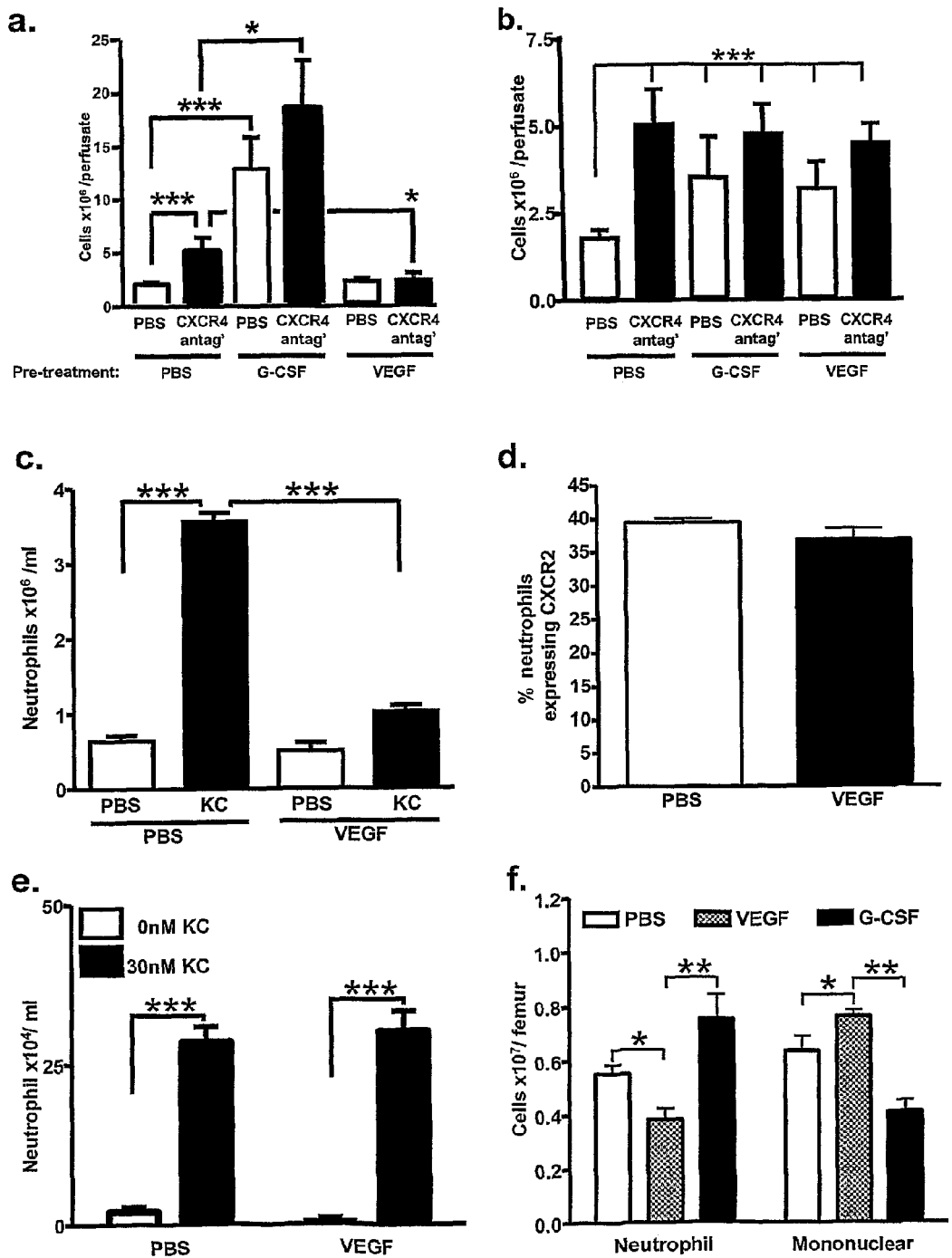

Neutrophils, like progenitor cells, are also retained within the bone marrow by the CXCR4/SDF-1α axis, and as such can be mobilized by G-CSF-treatment or CXCR4 antagonism ($P<0.001$, FIG. 24a and Martin et al., 2003). We therefore investigated whether VEGF pre-treatment of mice suppressed neutrophil mobilization as we observed for HPC mobilization (FIGS. 20b and 21b). As shown in FIG. 24a, VEGF pre-treatment profoundly suppressed neutrophil mobilization in response to the CXCR4 antagonist ($P<0.05$, 92% reduction). This effect was not seen when VEGF was administered acutely to mice (FIG. 24b). We therefore investigated whether the migratory capacity of neutrophils after VEGF-treatment was impaired in a similar manner to HPCs. During inflammatory reactions, neutrophils are rapidly mobilized from the bone marrow by ELR$^+$ CXC chemokines (e.g. KC) which stimulate neutrophil migration across the bone marrow sinusoidal endothelium (Martin et al., 2003; Wengner et al., 2008). Surprisingly, KC-induced mobilization of neutrophils in vivo was completely abrogated in mice pre-treated with VEGF ($P<0.001$, FIG. 24c). However, VEGF-treatment did not affect either the proportion of Gr-1$^+$ bone marrow neutrophils expressing CXCR2 (FIG. 24d), or the ability of bone marrow neutrophils to migrate towards KC in vitro (FIG. 24e). Thus, whilst VEGF pre-treatment suppressed both HPC and neutrophil mobilization in vivo; neutrophils, but not HPCs, retained the ability to undergo chemotaxis in vitro, suggesting that the suppression of HPC chemotaxis was particular to their character as progenitor cells compared to neutrophils which are terminally differentiated cells. Analysis of bone marrow revealed a significant reduction in absolute numbers of mature neutrophils (band and segmented nuclei) following VEGF-treatment compared to controls (FIG. 24f). It is unclear, however, whether this reduction in the bone marrow reserve accounts for the dramatic reduction in neutrophil mobilization.

VEGF-Treatment Stimulates Entry of HPCs Bit not EPCs into the Cell Cycle

Figure 25:
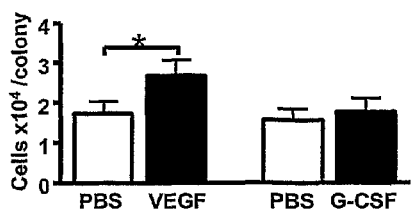
Figure 25:
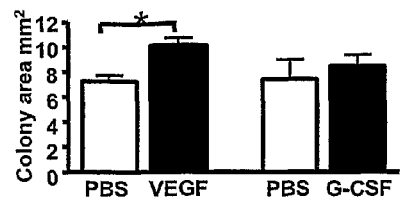
Figure 25:
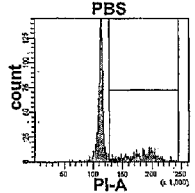
Figure 25:
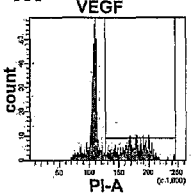
Figure 25:
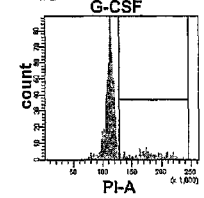
Figure 25:
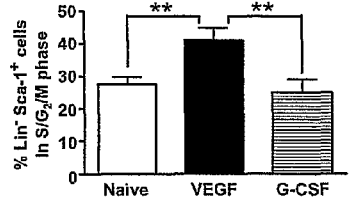
Figure 25:
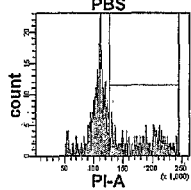
Figure 25:
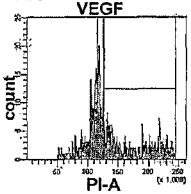
Figure 25:
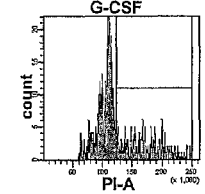
Figure 25:
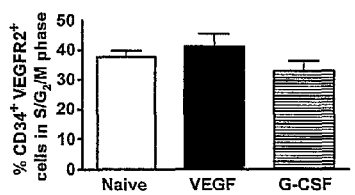
Figure 25:
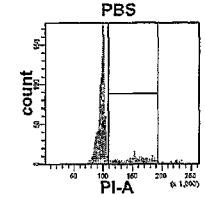
Figure 25:
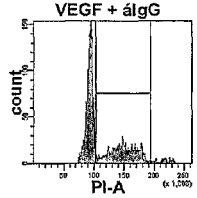
Figure 25:
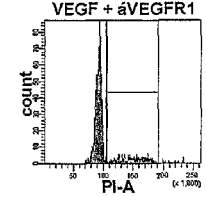
Figure 25:
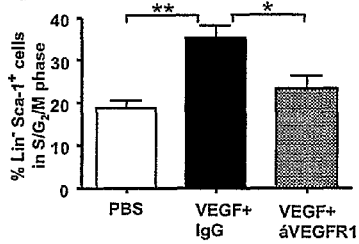

Activation of HPCs via VEGFR1 is required for cell survival and cell-cycling (Hattori et al., 2001; Gerber et al., 2002). Since a refractoriness of HPCs to migrate is a feature of cell-cycling (Bowie et al., 2006; Uchida et al., 1997; Roberts & Metcalf 1995), we next tested whether VEGF-treatment of mice stimulates HPC proliferation. Examination of HPC colonies grown from bone marrow of VEGF-treated mice revealed a significant increase in both their cellular content and size compared to controls (FIGS. 25a, 25b), suggesting that VEGF promotes proliferation of CFU-HPC ex viva. In vivo analysis revealed that VEGF-treatment led to a significant increase in the percentage of BM-HPCs (Lin⁻ Sca-1⁺ cells) in the S/G$_2$/M proliferative phase of the cell-cycle (FIG. 25c). In direct contrast, VEGF-treatment did not alter the percentage of CD34⁺VEGFR2⁺ EPCs in the S/G$_2$/M phase of the cell-cycle (FIG. 25d). Moreover, whilst VEGF has the capacity, as a primary growth factor, to alter the cell cycle status of HPCs (Gerber et al., 2002), we show, as previously described, that G-CSF does not stimulate entry of either HPCs (FIG. 25c) or EPCs (FIG. 25d) into the S/G$_2$/M phase of the cell cycle (McKinstry et al., 1997; Nicola et al., 1985; Colvin et al., 2007), However, as shown by others G-CSF does promote expansion and differentiation of granulocytes as evident by the increased numbers of neutrophils in the bone marrow (FIG. 24f) (McKinstry et al., 1997; Lord et al., 1989; 1991).

HPCs are known to express VEGFR1, therefore we next investigated whether the effect of VEGF in stimulating the entry of HPCs into the cell cycle in vivo was mediated via this receptor (FIG. 27). We show here that in vivo administration of an antibody directed against VEGFR1 completely suppressed the VEGF-stimulated entry of HPCs into the cell cycle (FIG. 25e).

VEGFR1 Antagonism Reverses VEGF-Induced Suppression of HPC Mobilization in Response to a CXCR4 Antagonist.

Figure 26:
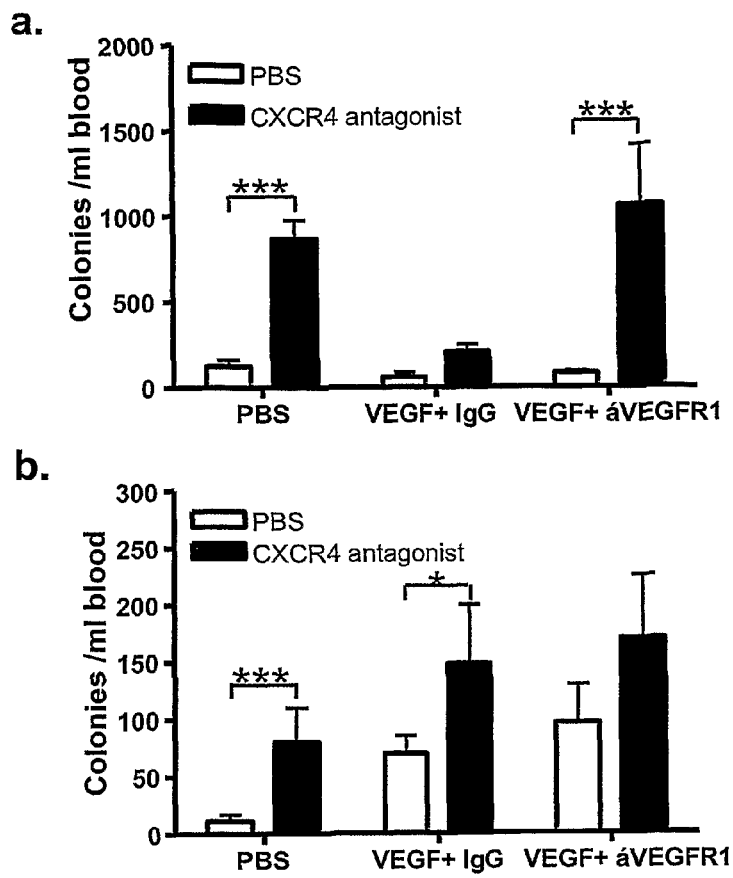
Figure 26:
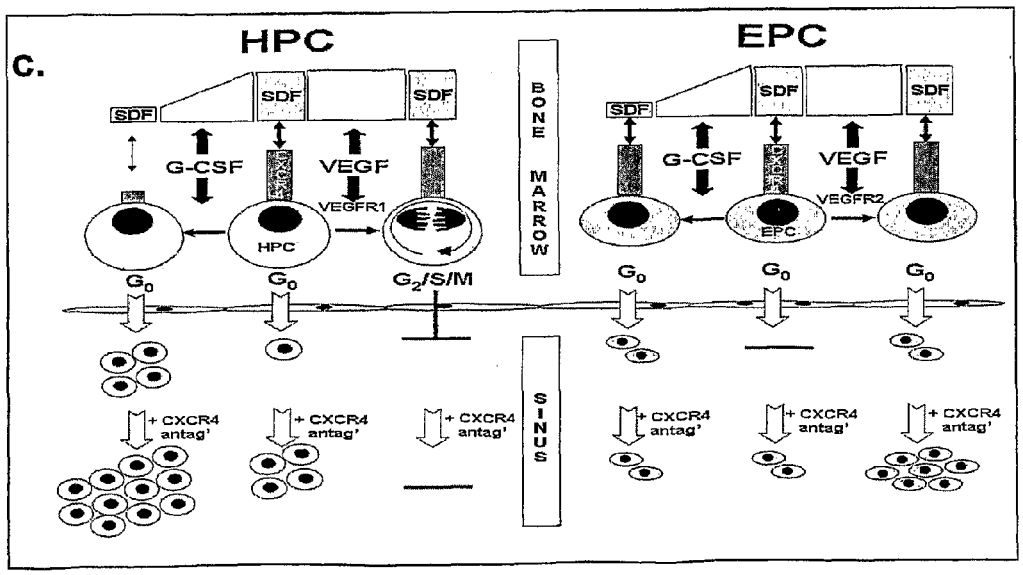

Since activation of VEGFR1 was demonstrated to lead to an accumulation of Lin⁻ Sca-1⁺ HPCs within the proliferative phase of the cell cycle (FIG. 25e). We next determined whether blocking of VEGFR1 in vivo would reverse VEGF-induced suppression of HPC mobilization in response to a CXCR4 antagonist. We show that administration of a VEGFR1 blocking mAb to VEGF-treated mice, completely restored the ability of the CXCR4 antagonist to mobilize HPCs from the bone marrow (P<0.001, FIG. 26a). In contrast, anti-VEGFR1 antibody administration did not affect VEGF-induced mobilization of EPCs (FIG. 26b). This data indicate that VEGF acting via VEGFR1 stimulates the entry of HPCs into the cell cycle and blocks their mobilization from the bone marrow, while effects of VEGF on VEGFR2 stimulate the mobilization of EPCs. Hence the differential effects of VEGF in regulating HPC and EPC mobilization are due to actions via distinct receptors.

Discussion

We show here, for the first time, that the mobilization of progenitor cell subsets, are differentially regulated by growth factors affecting their retention and cell cycle status. Specifically we show that whilst maximal mobilization of HPCs occurs when the CXCR4 antagonist is administered to mice pre-treated with G-CSF, under these conditions, EPC mobilization is sub-maximal and SPCs are not mobilized. In contrast, when mice are pre-treated with VEGF, the acute administration of a CXCR4 antagonist stimulates mobilization of EPCs and SPCs while suppressing HPC and neutrophil mobilization. As such, the profile of progenitor cells in the blood changes dramatically dependent on the treatment protocol.

The retention of HPCs and mature neutrophils within the bone marrow is dependent on the SDF-1α/CXCR4 chemokine axis. Thus, mechanisms that disrupt this axis promote the egress of HPCs and neutrophils (Martin et al., 2003; Levesque et al., 2003). Consistent with previous reports, we show here, that G-CSF mobilizes both neutrophils and HPCs, by reducing their expression of CXCR4 and decreasing levels of SDF-1α within the BM (Levesque et al., 2003; Wengner et al., 2008). In contrast, G-CSF alone mobilized only modest numbers of EPCs and no additive or synergistic effects were observed when mice pre-treated with G-CSF were administered the CXCR4 antagonist. There are no reports that EPCs express G-CSF receptors. Further, in this study G-CSF had no effect on the expression of CXCR4 by EPCs. This data suggests that G-CSF does not have a direct effect on EPCs, which may explain why mobilization of EPCs with the CXCR4 antagonist could not be enhanced by pre-treatment of mice with G-CSF.

Unexpectedly, pre-treatment of mice with VEGF suppressed the mobilization of both neutrophils and HPCs in response to the CXCR4 antagonist. This was not due to a change in CXCR4 expression by these cells. HPCs mobilized by G-CSF have been found to be exclusively in the G$_0$/G$_1$ phase of cell cycle, whereas HPCs remaining in the bone marrow are actively cycling (Bowie et al., 2006; Uchida et al., 1997; Roberts et al., 1995). This may be explained by the fact that proliferating HPCs cannot migrate, a necessary step in their mobilization from the bone marrow. Here we show, for the first time, that the exogenous administration of VEGF to naïve mice stimulates the entry of HPCs into the S/G2/M phase of the cell cycle in vivo and thereby severely impairs the migratory capacity of these cells, in vitro. Furthermore, as a consequence of their inability to migrate, the mobilization of HPCs by the CXCR4 antagonist is completely abrogated in mice treated with VEGF. It has previously been proposed that there are two pools of HPCs, a quiescent dormant reserve of HPCs residing in the endosteal niche that accounts for approximately one third of the HPCs and a 'mobilizable' pool of HPCs, that have the potential to proliferate, residing in the vascular niche adjacent to the sinsusoidal endothelium (Wilson et al., 2007). We propose that in stimulating HPCs in the vascular niche to enter the cell cycle VEGF has a profound effect on HPC mobilization.

It has previously been shown that in vivo treatment of immuno-suppressed mice with a blocking mAb to VEGFR1 reduces cell cycling of HPCs and the survival of HSCs following engraftment (Gerber et al., 2002 Hattori et al., 2002). This suggests that in this model endogenous VEGF acting via VEGFR1, expressed by HPCs, can regulate the proliferation/survival of HPCs/HSCs (Gerber et al., 2002). In this study we show that that selective blockade of VEGFR1 abolishes the ability of exogenous VEGF to stimulate HPC entry into the cell cycle in vivo and restores the ability of the CXCR4 antagonists to mobilize HPCs from the bone marrow.

Interestingly, the mobilization of neutrophils in response to both the CXCR4 antagonist and the chemokine, KC, was dramatically inhibited in mice pretreated with VEGF. This is not due to an effect on cell proliferation as these are terminally differentiated cells, indeed neutrophils harvested from the bone marrow of VEGF-treated mice migrated normally in response to chemokines. This suggests that VEGF may affect egress of mature cells from the bone marrow by other, as yet identified mechanisms. Tissue specific expression of VEGF has been shown to induce the perivascular expression of SDF-1α (Grunewald et. al., 2006). It is possible, therefore, that neutrophils may be retained within the vascular niche of the bone marrow following chronic VEGF-treatment due to locally increased SDF-1α expression, acting to re-enforce the retention of neutrophils via the CXCR4/SDF-1α axis (Martin et al 2003).

VEGF stimulates the migration and promotes survival of endothelial cells via signals emanating from VEGFR2 (Gerber et al., 1998). Interestingly, we observed that VEGF-treatment of mice did not stimulate the proliferation of VEGFR2+/CD34+ EPCs and as such EPCs in the bone marrow of these mice retained their ability to migrate towards chemokines in vitro and to be mobilized in response to CXCR4 antagonists in vivo. We show here that, anti-VEGFR1 antibody administration did not affect VEGF-induced mobilization of EPCs, indicating that EPC mobilization stimulated by VEGF is indeed mediated via VEGFR2. Hence the differential effects of VEGF in regulating HPC and EPC mobilization are mediated via distinct receptors, VEGFR1 on HPC and VEGFR2 on EPCs. The ability of VEGF to differentially promote the cell cycling of HPCs as compared to EPCs, explains why EPCs can be selectively mobilized by the CXCR4 antagonist in mice treated over 4 days with VEGF. Consistent with this data is the finding that acute administration of VEGF alone or in combination with the CXCR4 antagonist did not selectively mobilize EPCs from the bone marrow. Mechanistic differences between acute and chronic VEGF exposure are unknown, however acute administration of high doses of VEGF, delivered by adenovirus, is associated with capillary leakiness which may facilitate the escape of progenitor cells from the BM (Moore et al., 2001). Indeed adVEGF has been shown to induce the non-selective mobilization of myeloid cells, HPCs, and EPCs, as observed here with acute VEGF administration (Hattori et al., 2001).

The G-CSF-treatment protocol used here, has been evaluated to promote cardiac regeneration in patients with MI (Orlic et al., 2001; 2001a; Kocker et al., 2001; Powell et al., 2005; Zolnhofer et al., 2006; Ince et al., 2005; Ripa et al., 2006; Ellis et al., 2006; Hill et al., 2005). These trials have been disappointing with only 1 out of 5 trials showing any significant clinical benefit (Zolnhofer et al., 2006; Ince et al., 2005; Ripa et al., 2006; Ellis et al., 2006; Hill et al., 2005). As we reveal here, such limited clinical success might be because G-CSF administration is not a particularly efficacious regime for mobilizing EPCs or SPCs which may be important for cardiac regeneration. Indeed, we have shown that G-CSF treatment actually decreases the number of EPCs in bone marrow, thus depleting the available reservoir for tissue recruitment and revascularization. Further, G-CSF also stimulates neutrophil mobilization, which may exacerbate the inflammatory response and negatively impact cardiac regeneration (Hill et al., 2005; Kang et al., 2004; Zemecke et al., 2008). In this study we have identified a treatment protocol that selectively mobilizes EPCs and SPCs, but not HPCs or neutrophils, from the bone marrow. Future studies will investigate the therapeutic efficacy of this mobilizing regime for cardiac regeneration following myocardial infarction.

Taken together, the results presented here indicate that different factors and molecular mechanisms regulate the mobilization of discrete populations of progenitor cells from the bone marrow. This has far reaching implications for our understanding of mechanisms regulating the selective recruitment of different populations of progenitor cells in disease and the development of therapeutic strategies to mobilize specific sub-populations for regenerative medicine.

Experimental Procedures.

Reagents

Recombinant murine chemokines and growth factors KC/CXCL1, SDF-1α/CXCL12, G-CSF, and VEGF were from PeproTech (London, U.K.). For in vivo blocking experiments, anti-murine polyclonal VEGFR1 antibody (AF471) was purchased from RnD Systems (Abingdon, UK): Control rat IgG was purchased from Jackson Immunoresearch (Newmarket U.K.) The CXCR4 antagonist AMD3100, propidium iodide (PI), Triton X, and RNase were purchased from Sigma Aldrich (Poole, U.K.). Dulbecco's Modified Eagles medium (DMEM) was purchased from Life Sciences (Paisley, U.K.). Methocult and supplements was obtained from StemCell Technologies (Vancouver, Canada). EGM-2 basal media and supplements were purchased from Lonza (Wokingham, U.K.). 3 µm pore size transwell chemotaxis plates were purchased from Neuroprobe (Gaithersburg U.S.A.). 5 µm pore size transwell chemotaxis inserts were purchased from Corning (New York U.S.A). Anti-human/mouse CXCL12/SDF-1 antibody, biotinylated anti-human/mouse CXCL12/SDF-1 antibody, and streptavidin-HRP for ELISA were purchased from RnD Systems (Abingdon, U.K.). Rat anti-mouse CD34-FITC antibody (IgG2a) was purchased from AbD Serotec (Nottingham U.K.). Rat anti-mouse Sca-1-APC (Ly-6A/E) antibody (IgG2a) and rat anti-mouse VEGFR2-APC (Flk-1) antibody (IgG2a) were purchased from eBioscience (Wembley U.K.). Rat anti-mouse CD11b-FITC antibody (IgG2b), Rat anti-mouse Gr-1-FITC (Ly-6G and Ly-6C) antibody (IgG2b), rat anti-mouse CD45R/B220-FITC antibody (IgG2a), rat anti-mouse CD3e-FITC antibody (IgG2a), rat anti-mouse TER119-FITC antibody (IgG2b), rat anti-mouse CXCR4-PE antibody (IgG2b) were purchased from BD Pharmingen (Oxford U.K.). Rat anti-mouse CXCR2-APC antibody (IgG2a) was purchased from RnD Systems (Abingdon, U.K.). Rat anti-mouse CD16/CD32 Fc-block (IgG2b) was purchased from BD Pharmingen (Oxford U.K.). The following isotype control antibodies were purchased: rat IgG2a-FITC, IgG2b-FITC, and rat IgG2b-PE (BD Pharmingen, Oxford U.K.). Rat IgG2a-APC was purchased from RnD Systems (Abingdon, U.K.). For immunohistochemistry, the following antibodies were used: goat anti-mouse VEGFR1 antibody, rabbit anti-mouse VEGFR2 antibody, rat antimouse CD34 antibody, goat anti-mouse VE-Cadherin antibody were purchased from Santa-Cruz Biotech (Santa Cruz, U.S.A.). Rat anti-mouse CD45 antibody, rat anti-mouse CD29 antibody, rat anti-mouse CD105 antibody were purchased from BD Pharmingen (Oxford, U.K.). rat anti-mouse CD115 antibody was purchased from eBioscience (Wembley, U.K.). Rabbit anti-human vWF antibody was purchased from DAKO (Glostrup, Denmark). The following isotype controls were used: Rat IgG1 from BD Pharmingen (Oxford, U.K.), goat IgG and rabbit IgG from Santa-Cruz Biotech (Santa Cruz, U.S.A.). The following fluorescently labeled secondary antibodies were used: donkey anti-goat Alexafluor 568 antibody, goat anti-rat Alexafluor 594 antibody, goat anti-rabbit Alexafluor 488 antibody were purchased from Molecular Probes (Paisley, U.K.)

Pre-Treatment with G-CSF or VEGF

Female BALB/c mice were purchased from Harlan (Oxford, United Kingdom). Mice, at the age of 8-10 weeks were administered VEGF (2.5 µg/mouse i.p.), G-CSF (2.5 µg/mouse i.p.), or vehicle on 4 consecutive days. 24 hours after the last injection, mice were administered a CXCR4 antagonist (AMD3100, 5 mg/kg i.p), KC (30 µg/kg i.v.) or vehicle and blood was collected via cardiac puncture 60 minutes later for enumeration of circulating leukocyte, HPC, EPC, and stromal progenitor cell levels. In other experiments, mice pre-treated with G-CSF or VEGF were used for in situ perfusion of the mouse hind limb as explained below. All studies were carried out under the United Kingdom's Animals (Scientific Procedures) Act of 1986 and local ethical approval from Imperial College, London.

Administration of Anti-VEGFR1 Antibody

Mice were administered anti-VEGFR1 or control IgG (2.5 mg/kg i.p. Ohki et al., 2005) 30 minutes before VEGF administration on days 1 and 3 of the 4 day VEGF-treatment protocol.

In Situ Perfusion of Mouse Hind Limb

On day 5 following pre-treatment of growth factors, mice were anaesthetized and the femoral artery and vein exposed. The hind limb was isolated by occlusion of the external iliac artery, superficial epigastric and muscular branch. Polyethylene cannulae (Portex, London, UK) were immediately inserted into the femoral artery and vein as previously described (Martin et al., 2003; 2006; Wengner et al., 2008). Perfusion buffer was infused via the arterial cannula and removed from the venous cannula using a Minipuls peristaltic pump (Anachem, Luton, UK). The hind limb was perfused for an initial 2 minutes to remove remaining blood from the vasculature and then perfused for a further 60 min with vehicle alone or the CXCR4 antagonist (AMD3100, 0.1 mM), infused over the first 10 minutes using an infusion/withdrawal pump (Harvard Instruments, U.K.).

In some studies the effects of acute administration of G-CSF or VEGF on HPC, EPC, and stromal progenitor cell mobilization were examined. G-CSF or VEGF (50 nM) were added to the perfusion buffer for an initial 10 minutes.

Analysis of Mobilized Cells from the Bone Marrow in Blood and Perfusate.

The perfusate was centrifuged and re-suspended in DMEM+20% FBS. In some experiments citrated blood was obtained via cardiac bleed and lysed for red blood cells. Bone marrow and perfusate cytospins, and blood smears were stained using DiffQuik for the enumeration of mononuclear cells, eosinophils, and neutrophils. Bone marrow, perfusate and lysed blood were then used for assays outlined below to enumerate HPCs (CFU-HPC), EPCs (CFU-EPC), SPCs (CFU-F).

CFU-HPC Assay $5 \times 10^4$ cells were added to Methocult medium (Stem cell technologies) supplemented with specific cytokines and growth factors to enable formation of CFU-HPC. Mobilized cells were incubated for 11 days before quantification. Further characteristics of CFU-HPC colonies were obtained on day 12, namely the mean number of cells in each colony, and the mean colony area. The mean colony area ($mm^2$) was determined by image analysis using Scion Image analysis program (NIH). The cell number was determined by diluting colonies grown in Methocult into DMEM (to disperse the methylcellulose) and aspirating the colonies into a single cell suspension before obtaining a cell count. Cells taken from HPC colonies and immunostained showed CD1155, CD34, CD45, VEGFR1 positive cells, but were negative for VEGFR2, VE-Cadherin, and von Willebrand Factor (vWF) (FIG. 27)

CFU-EPC Assay $5 \times 10^5$ cells were added to EPC colony media (EGM-2 basal media+supplements, and additional VEGF: 60 µg/L, and FBS: 16% final concentration) on fibronectin-coated plates. Dishes were incubated for 7 days before media was changed, and then incubated for a further 14 days before the enumeration of EPC colonies (CFU-EPC). These "late outgrowth" EPC colonies exhibited a cobblestone morphology and by immunohistochemical analysis (Protocol: see below) expressed CD34, VEGFR2, VE-Cadherin, and vWF (FIG. 27) stained positively with GS-lectin and were able to uptake acetyl-LDL (FIG. 28a), as reported by others (Nolan et al., 2007; Yoder et al., 2007; Hur et al., 2004). Importantly, 'late outgrowth' CFU-EPC did not express CD115, CD14 or CD45 (FIG. 27), and are therefore not of a monocyte-macrophage lineage (Hirschi et al., 2008). Moreover, CFU-EPC were able to form tubules in an in vitro EC Matrix angiogenesis assay (See below) whereby complete mesh-like structures formed after 18 hours in culture (FIG. 28b-d).

CFU-SPC (CFU-F) Assay $5 \times 10^5$ cells were added to Mesencult media including supplements (Stemcell Technologies). Dishes were incubated for 7 days before media was changed, and then incubated for a further 14 days before the enumeration of SPC colonies (CFU-F). Plastic adherent bone marrow derived SPCs were shown to express CD29 and CD105 and were negative for CD45 and CD34 (FIG. 30a) as demonstrated in previous studies on stromal progenitor cells (Phinney et al., 1999; Pittenger et al., 1999). Furthermore, expanded SPC colonies were assessed for their ability to differentiate into other cell types (see below), and were capable of mesenchymal tri-lineage differentiation into adipocytes (FIG. 21c), osteocytes (FIG. 21d) and chondrocytes (FIG. 21e) These progenitor cells exhibit all the characteristics of murine mesenchymal stem cells (Pittenger et al., 1999)

The total number of colony forming units mobilized was calculated according to the number of colonies per plate×by the total number of leukocytes mobilized/number of cells seeded.

Flow Cytometry Analysis of Chemokine Receptor Expression on Cells Residing in Bone Marrow.

For flow cytometric analysis, cells were re-suspended in FACS buffer. To identify neutrophils in the bone marrow, surface expression of the granulocyte marker Ly-6G/Ly6C (Gr-1) was determined. Neutrophils were identified as $Gr-1^{high}$ positive cells with a characteristic high side scatter profile. HPCs residing in the BM were selected as being negative for lineage (Lin⁻) markers: CD3e, CD11b, CD45R, Ly-76, and Gr-1 and positive for Sca-1 (Lin⁻ Sca-1⁺ cells) (Gerber et al., 2002; Uchida, et al., 1997). EPCs residing in the BM were selected as being positive for both CD34 and VEGFR2 (CD34⁺ VEGFR2⁺ cells) (Asahara et al., 1997; Yoon et al., 2005). Furthermore, neutrophils were stained for the surface expression of CXCR2, whilst Lin⁻ Sca-1⁺ cells and CD34⁺ VEGFR2⁺ cells were stained for the cell surface expression of CXCR4. Samples were then washed and then quantified on a FACSAria cell sorter (BD Biosciences, Oxford, United Kingdom) and analysed using FACSDiva software.

PI Staining to Determine Cell Cycle Status

Lin⁻ Sca-1⁺ cells and CD34⁺ VEGFR2⁺ cells were analysed to determine their cell cycling status using a propidium iodide (PI) stain. Unfixed cells were initially stained as explained above to identify their cell type before the addition of 50 µL PI (100 µg/ml), and 50 pL RNase (100 µg/ml) was added to minimise PI binding to RNA. 5 minutes before flow cytometric analysis, 50 µL of 0.1% Triton X (in saline) was added to sample to permeabilize the cell membrane and allow DNA binding. Analysis of flow cytometry data of PI-stained cells was performed using FACSDiva software. A dotplot of PI-Width against PI-Area was recorded. Aggregates of cells were detected as cells having a larger PI-W profile and were not included in the gate. A PI-A histogram of the gated cells showed the first peak to represent cells in $G_0/G_1$, the second peak cells in $G_2/M$, and the in between area S phase cells. To calculate the percentage of cells undergoing active cell cycling, a marker was set to exclude the $G_0/G_1$ peak and the percentage of cells in $S/G_2/M$ was calculated.

Bone Marrow Histology

Femoral bone marrow was fixed by infusion of 2.5% glutaraldehyde in a modified Krebs-Ringers buffer for 15 minutes using the in situ perfusion technique previously described (Martin et al., 2003; 2006; Wengner et al., 2008). The femur was removed and placed in fresh glutaraldehyde fixative before being processed and stained with toluidine blue.

In Vitro Chemotaxis Assays of Neutrophils, HPCs and EPCs

Bone marrow-derived neutrophils were tested for migration towards KC (30 nM) using 3 µm pore sized transwell chemotaxis plates as previously described (Wengner et al., 2008). To measure HPC and EPC migration towards SDF-1α, murine bone marrow cells ($2 \times 10^6$ cells) were placed in the upper chamber of transwell inserts (5 μm pore size Corning). These in turn were placed in individual wells of a 24 well cell culture plate with 30 nM SDF-1α added. Chambers were incubated for 4 hours at 37° C. and migrated cells were then placed in methocult or EPC colony media as described above for the enumeration of CFU-HPC and CFU-EPC respectively.

SDF-1α ELISA on Bone Marrow Supernatants

Supernatant from bone marrow aspirates was analyzed for SDF-1α content as per the recommended protocol for the capture and detection antibody (MAB350 and BAF310 respectively. RnD systems).

Statistical Analysis

Data are expressed as mean±SEM. In vivo mobilization data and in vitro chemotaxis data were analysed using two-way analysis of variance (ANOVA), followed by Bonferroni multiple-comparisons test. Flow cytometry data of PI stain were analysed using one-way ANOVA, followed by Bonferroni multiple-comparisons test. Flow cytometry data of chemokine receptor expression were analysed using Student's T-test. All analyses were conducted using the GraphPad Prism statistical package (version 4.0; Graph Pad, San Diego, Calif.). P values less than 0.05 were considered significant.

Immunohistochemistry of HPC, EPC, and SPC Colonies.

EPC and SPC colonies grown in chamber slides, and cytospins of cells from HPC colonies were fixed in ice cold methanol for 10 minutes, before washing in PBS+1% BSA. Slides were blocked for 30 minutes with PBS+10% BSA. Slides were then stained with the following antibodies: goat anti-mouse VEGFR1, rabbit anti-mouse VEGFR2, rat anti-mouse CD34, goat anti-mouse VE-Cadherin, rat anti-mouse CD45, rat anti-mouse CD29, rat anti-mouse CD105, rat anti-mouse CD115, rabbit anti-human vWF, or goat anti-mouse CD14. The following isotype controls were used: Rat IgG1, goat IgG, and rabbit IgG. After 90 minutes, slides were washed and incubated with the following appropriate fluorescently labeled secondary antibodies: donkey anti-goat Alexafluor 568 antibody, goat anti-rat Alexafluor 594 antibody, goat anti-rabbit Alexafluor 488 antibody. After a further wash, slides were mounted onto coverslips using glycerol based mounting medium containing a 4',6-diamidino-2-phenylindole (DAPI) counterstain. Slides were analyzed using a fluorescent microscope (Leica, Germany).

Staining of EPC Colonies with GS-Lectin and Uptake of Ac-LDL

DIL-labeled Acetylated-low density lipoprotein (Ac-LDL) was added to EPC media (5 μg/ml) and cells were incubated for 4 hours at 37° c. Colonies were then washed in PBS and fixed with 2% PFA for 10 minutes before incubation with fluoroscein conjugated griffonia-simplicifolia (GS)-lectin (10 μg/ml in PBS) for 60 minutes. Colonies were then analyzed using a fluorescent microscope (Leica, Germany).

In Vitro Angiogenesis Assay

The ability of EPCs to form tubules was assessed using an in vitro angiogenesis assay (Madri & Pratt 1986; Salani et al., 2000). EC Matrix Gel solution and EC Matrix diluent buffer (Chemicon) were mixed in a ratio of 9:1 at 4° c. 50 μl was then added wells of a pre-cooled 96 well plate and this was then incubated at 37° C. for 1 hour to allow the matrix solution to solidify. EPC colonies were harvested by trypsinization and re-suspended in EPC growth media at a density of $1 \times 10^5$ cells/ml and seeded (150 μl) onto the surface of the polymerized matrix. Cells were then incubated for 24 hours, and cellular network structures were fully developed by 12-18 hours.

Tri-Lineage Differentiation of SPC Colonies

To induce differentiation of SPCs into adipogenic and osteogenic lineages appropriate differentiation media was added to SPC colonies. Basic differentiation media consisted of 10% FBS, penicillin/streptomycin and fungizone. Osteogenic differentiation was induced by adding 50 μg/ml ascorbic acid-2-phosphate, 10 nM dexamethasone and 10 mM β-glycerol to basic media (Eslaminejad et al., 2006). Adipogenic differentiation was induced by adding 50 μg/ml indomethacine, 100 nM dexamethasone and 10 ng/ml insulin to basic media (Zuk et al., 2002). Control cultures were incubated in basic media. The differentiation media was replaced three times a week for a period of 20 days. To promote chondrogenic differentiation the micromass culture technique was used (Eslaminejad et al., 2006, Pevsner-Fischer et al., 2006, Pittenger et al., 1999). SPCs were detached by trypsinization and pelleted in a conical polypropylene tube. Chondrogenic differentiation media consisting of basic media supplemented with 10 ng/ml TGF-β, 50 nM ascorbic acid-2-phosphate and 6.25 μg/ml insulin was added to the cells (Pevsner-Fischer et al., 2006). The chondrogenic differentiation media was changed three times a week for a period of 2-3 weeks.

To confirm differentiation of SPCs to mesenchymal lineages, osteocytes, adipocytes and chondrocytes were stained with cell type specific dyes as reported in previous publications (Pittenger et al., 1999, Zuk et al., 2002). SPCs cultured in osteogenic media were stained with Alizarin red. This dye is used to demonstrate the presence of calcium. Interaction of Alizarin dye with calcium ions results in a bright red stain. SPCs cultured in adipogenic media were stained with Oil red O (Sigma-Aldrich) which is a fat soluble dye that stains triglycerides and lipids of fixed cells with a deep red colour. Cells cultured in chondro-inductive media were stained using Toluidine Blue, which stains the background blue (orthochromatic staining) and the areas of cartilage matrix red-purple (metachromatic staining).

REFERENCES

Asahara, T., Murohara, T., Sullivan, A., Silver, M., van der Zee, R., Li, T., Witzenbichler, B., Schatteman, G., Isner, J. M. (1997) Isolation of putatative progenitor endothelial cells for angiogenesis. Science. 275, 964-967

Asahara, T., Masuda, H., Takahashi, T., Kalka, C., Pastore, C., Silver, M., Kearne, M., Magner, M., Isner, J. M. (1999) Bone marrow origin of endothelial progenitor cells responsible for post natal vasculogenesis in physiological and pathological neovascularization. Circ. Res. 85, 221-228

Au, P., Tam, J., Fukumura, D., Jain, R. K. (2008). Bone marrow derived mesenchymal stem cells facilitate engineering of long-lasting functional vasculature. Blood. *DOI* 10.1182/*blood*-2007-10-118273

Bielby, R., Jones, E., McGonagle, D. (2007) The role of mesenchymal stem cells in maintenance and repair of bone. Injury. 38, S26-S32

Bowie, M. B., McKnight, K. D., Kent, D. G., McCaffrey, L., Hoodless, P. A., Eaves, C. J. (2006). Hematopoietic stem cells proliferate until after birth and show a reversible phase-specific engraftment defect. J. Clin. Invest. 116, 2808-2816

Broxmeyer, H. E., Orschell, C. M., Clapp, D. W., Hangoc, G., Cooper, S., Plett, P. A., Liles, W. C., Li, X., Graham-Evans, B., Campbell, T. B. et al. (2005). Rapid mobilization of murine and human hematopoietic stem and progenitor cells with AMD3100, a CXCR4 antagonist. J. Exp. Med. 201, 1307-1318

Calandra, G., McCarty, J., McGuirk, J., Tricot, G., Crocker, S. A., Badel, K., Grove, B., Dye, A., Bridger, G. (2008). AMD3100 plus G-CSF can successfully mobilize CD34+ cells from non-Hodgkin's lymphoma, Hodgkin's disease and multiple myeloma patients previously failing mobilization with chemotherapy and/or cytokine treatment: compassionate use data. Bone Marrow Transplantation. 41, 331-338

Cashen, A. F., Link, D., Devine, S., DiPersio, J. (2004). Cytokines and stem cell mobilization for autologous and allogeneic transplantation. Curr. Hematol. Rep. 3, 406-12

Capoccia, B. J., Shepherd, R. M., Link, D. C. (2006). G-CSF and AMD3100 mobilize monocytes into the blood that stimulate angiogenesis in vivo through a paracrine fashion. Blood. 108, 2438-2445

Colvin. G. A., Dooner, M. S., Dooner, G. J., Sanchez-Guijo, F. M., Demers, D. A., Abedi, M., Ramanathan, M., Chung, S., Pascual, S., Quesenberry, P. J. (2007) Stem cell continuum: differentiation hotspots. Exp. Hematol. 35, 96-107.

Ellis, S. G., Penn, M. S., Bolwell, B., Garcia, M., Chacko, M., Wang, T., Brezina, K. J., McConnell, G., Topol, E. J. (2006) Granulocyte colony stimulating factor in patients with large acute myocardial infarction: Results of a pilot dose-escalation randomized trial. Am. Heart J. 152, e9-e14

Eslaminejad, M. B., Nikmahzar, A., Taghiyar, L., Nadri, S. & Massumi, M. (2006) Murine mesenchymal stem cells isolated by low density primary culture system. Dev Growth Differ, 48, 361-370.

Forster, R., Kremmer, E., Schubel, A., Breitfeld, D., Kleinschmidt A., Nerl, C., Bernhardt, G., Lipp, M. (1998). Intracellular and surface expression of the HIV-1 coreceptor CXCR4/fusin on various leukocyte subsets: rapid internalization and recycling upon activation J. Immunol. 160, 1522-1531

Gerber, H-P., McMurtrey, A., Kowalski, J., Yan, M., Keyt, B. A., Dixit, V., Ferrara, N. (1998). Vascular endothelial growth factor regulates endothelial cell survival through the phosphatidylinositol 3'-kinase/Akt signal transduction pathway. J. Biol Chem. 273, 30336-30343

Gerber, H-P., Malik, A. K., Solar, G. P., Sherman, D., Liang, X. H., Meng, G., Hong, K., Marsters, J. C., Ferrara N. (2002). VEGF regulates haematopoietic stem cell survival by an internal autocrine loop mechanism. Nature. 417, 954-958

Grunewald, M., Avraham, I., Dor, Y., Bachar-Lustig, E., Itin, A., Yung, S., Chimenti, S., Landsman, L., Abramovitch, R., Keshet, E. (2006). VEGF-induced adult neovascularisation: recruitment. Retention, and role of accessory cells. Cell. 124, 175-189

Haudek, S. B., Xia, Y., Huebener, P., Lee, J. M., Carlson, S., Crawford, J. R., Pilling, D., Gomer, R. H., Trial, J., Frangogiannis, N. G., Entman, M. L. (2006). Bone marrow-derived fibroblast precursors mediate ischemic cardiomyopathy in mice. Proc Natl Acad Sci USA. 103, 18284-9

Hattori, K., Dias, S., Heissig, B., Hackett, N. R., Lyden, D., Tateno, M., Hicklin, D. J., Zhu, Z., Witte, L., Crystal, R. G., et al. (2001). Vascular endothelial growth factor and angiopoietin-1 stimulate postnatal hematopoiesis by recruitment of vasculogenic and hematopoietic stem cells. J. Exp. Med. 193, 1005-1014

Hattori, K., Heissig, B., Wu, Y., Dias, S., Tejada, R., Ferris, B., Hicklin, D. J., Zhu, Z., Bohlen, P., Witte, L., et al. (2002). Placental growth factor reconstitutes hematopoiesis by recruiting VEGFR1(+) stem cells from bone-marrow microenvironment. Nat Med. 8, 841-849.

Hess, D. C. & Borlongan, C. V. (2008). Stem cells and neurological diseases. Cell Prolif. 41, Suppl 1 94-114

Hill, J. M., Syed, M. A., Arai, A. E., Powell, T. M., Paul, J. D., Zalos, G., Read, E. J., Khuu, H. M., Leitman, S. F., Horne, M., et al. (2005). Outcomes and risks of granulocyte colony-stimulating factor in patients with coronary artery disease. J. Am. Coll. Cardiol, 46, 1643-1648

Hirschi, K. K., Ingram, D. A., Yoder, M. C. (2008). Assessing identity, phenotype, and fate of endothelial progenitor cells. Arterioscler. Thromb. Vasc. Biol. 28, 1584-1695

Hur, J., Yoon, C-H., Kim, H-S., Choi, J-H., Kang, H-J., Hwang, K-K., Oh, B-H., Lee, M-M., Park, Y-B. (2003). Characterization of two types of endothelial progenitor cells and their different contributions to neovasculogenesis. Arterioscler. Thromb. Vasc. Biol. 24, 288-293.

Ince, H., Petzsch, M., Kleine, H. D., Schmidt, H., Rehders, T., Körber, T., Schümichen, C., Freund, M., Nienaber, C. A. (2005) Preservation from left ventricular remodelling by front-integrated revascularization and stem cell liberation in evolving acute myocardial infarction using granulocyte-colony-stimulating factor (FIRSTLINE-AMI). Circulation. 112, 3097-3106

Kang, H. J., Kim, H. S., Zhang, S. Y., Park, K. W., Cho, H. J., Koo, B. K., Kim, Y. J., Soo Lee, D., Sohn, D. W., Han, K. S., Oh, B. H., et al. (2004). Effects of intracoronary infusion of peripheral blood stem-cells mobilized with granulocyte-colony stimulating factor on left ventricular systolic function and restenosis after coronary stenting in myocardial infarction: the MAGIC cell randomised clinical trial. Lancet, 363, 751-756

Kocker, A. A., Schuster, M. D., Szabolcs, M. J., Takuma, S., Burkhoff, D., Wang, J., Homma, S., Edwards, N. M., Itescu, S. (2001) Neovascularization of ischaemic myocardium by human bone marrow-derived angioblasts prevents cardiomyocyte apoptosis, reduces remodelling and improves cardiac function. Nat. Med. 7, 430-436

Le Blanc, K. & Ringden, O. (2007) Immunomodulation by mesenchymal stem cells and clinical experience. J. Intern Med. 262, 509-525

Levesque J. P., Hendy, J., Takamatsu, Y., Simmons, P. J., Bendall, L. J. (2003). Disruption of the CXCR4/CXCL12 chemotactic interaction during hematopoietic stem cell mobilization induced by G-CSF or cyclophosphamide. J. Clin. Invest. 111, 187-196

Lord, B. I., Bronchud, M. H., Owens, S., Chang, J., Howell, A., Souza, L., et al. (1989). The kinetics of human granulopoiesis following treatment with granulocyte colony-stimulating factor in vivo. Proc. Natl. Acad. Sci. USA. 86, 9499-9503

Lord, B I., Molineux, G., Pojda, Z., Souza, L. M., Mermod, J. J., Dexter, T. M. (1991). Myeloid cell kinetics in mice treated with recombinant interleukin-3, granulocyte colony stimulating factor (CSF), or granulocyte-macrophage CSF in vivo. Blood. 77, 2154-2159

Madri, J. A., & Pratt, B. M. (1986). Endothelial cell-matrix interactions: in vitro models of angiogenesis. J. Histochem. Cytochem. 34, 85-91

Martin, C., Burdon, P. C., Bridger, G., Gutierrez-Ramos, J. C., Williams, T. J., Rankin, S. M. (2003). Chemokines acting via CXCR2 and CXCR4 control the release of neutrophils from the bone marrow and their return following senescence. Immunity. 19, 583-593

Martin, C., Bridger, G. J., Rankin, S. M. (2006) Structural analogues of AMD3100 mobilise haematopoietic progenitor cells from bone marrow in vivo according to their ability to inhibit CXCL12 binding to CXCR4 in vitro. Br. J. Haematol. 134, 326-329

Meirelles, L. D. S., & Nardi, N. B. 2003. Murine marrow-derived mesenchymal stem cell: isolation, in vitro expansion, and characterization. Br. J. Haematol. 123, 703-711

Moore, M. A., Hattori, K., Heissig, B., Shieh, J. H., Dias, S., Crystal, R. G., Rafii, S. (2001). Mobilization of endothelial and hematopoietic stem and progenitor cells by adenovector-mediated elevation of serum levels of SDF-1, VEGF, and angiopoietin-1. Ann. N. Y. Acad. Sci. 938, 36-45. Discussion 45-47

McKinstry, W. J., Li, C-L., Rasko, J. E. J., Nicola, N. A., Johnson, G. R., Metcalf, D. (1997) Cytokine receptor expression on hematopoietic stem and progenitor cells. Blood. 89, 65-71

Nicola, N. A., Metcalf, D. (1985). Binding of 125I-labeled granulocyte colony stimulating factor to normal hemopoietic cells. J. Cell Physiol. 124, 313-321

Nolan, D. J., Ciarrocchi, A., Mellick, A. S., Jaggi, J. S., Bambino, K., Gupta, S., Heikamp, E., McDevitt, M. R., Scheinberg, D. A., Benezra, R., Mittal, V. (2007). Genes & Development. 21, 1546-1558

Ohki, Y., Heissig, B., Sato, Y., Akiyama, H., Zhu, Z., Hicklin, D. J., Shimada, K., Ogawa, H., Daida, H., Hattori, K., Ohsaka, A. (2005). Granulocyte colony-stimulating factor promotes neovascularisation by releasing vascular endothelial growth factor from neutrophils. FASEB J. 19, 2005-2017

Orlic, D., Kajstura, J., Chimenti, S., Jakoniuk, I., Anderson, S. M., Li, B., Pickel, J., McKay, R., Nadal-Ginard, B., Bodine, D. M., Leri, A, et al. (2001) Bone marrow cells regenerate infarcted myocardium. Nature. 410, 701-705

Orlic, D., Kajstura, J., Chimenti, S., Limana, F., Jakoniuk, I., Quaini, F., Nadal-Ginard, B., Bodine, D. M., Leri, A., Anversa, P. (2001a). Mobilized bone marrow cells repair the infarcted heart, improving function and survival. Proc. Natl. Acad. Sci. USA. 98, 10344-10349

Palframan, R. T., Collins, P. D., Severs, N. J., Rothery, S., Williams, T. J., Rankin, S. M. (1998). Mechanisms of acute eosinophil mobilization from the bone marrow stimulated by interleukin 5: the role of specific adhesion molecules and phosphatidylinositol 3-kinase. J. Exp. Med. 88, 1621-1632

Palframan, R. T., Collins, P. D., Williams, T. J., Rankin, S. M. (1998a). Eotaxin induces a rapid release of eosinophils and their progenitors from the bone marrow. Blood. 91, 2240-8

Pevsner-Fischer, M., Morad, V., Cohen-Sfady, M., Rousso-Noori, L., Zanin-Zhorov, A., Cohen, S., Cohen, I. R. & Zipori, D. (2007) Toll-like receptors and their ligands control mesenchymal stem cell functions. Blood, 109, 1422-1432.

Philips, R. J., Burdick, M. D., Hong, K., Lutz, M. A., Murray, L. A., Xue, Y. Y., Belperio, J. A., Keane, M. P., Strieter, R. M. (2004). Circulating fibrocytes traffic to the lungs in response to CXCL12 and mediate fibrosis. J. Clin. Invest. 114, 438-446

Phinney, D. G., Kopen, G., Isaacson, R. L., Prockop, D. J. (1999). Plastic adherent stromal cells from the bone marrow of commonly used strains of inbred mice: variations in yield, growth, and differentiation. J. Cell. Biochem. 72, 570-585

Pittenger, M. F., Mackay, A. M., Beck, S. C., Jaiswal, R. K., Douglas, R., Mosca, J. D., Moorman, M. A., Simonetti, D. W., Craig, S., Marshak, D. R. (1999). Multilineage potential of adult human mesenchymal stem cells. Science. 284, 143-147

Powell, T. M., Paul, J. D., Hill, J. M., Thompson, M., Benjamin, M., Rodrigo, M., McCoy, J. P., Read, E. J., Khuu, H. M., Leitman, S. F., Finkel, T., et al. (2005). Granulocyte colony-stimulating factor mobilizes functional endothelial progenitor cells in patients with coronary artery disease. Arterioscler Thromb Vasc Biol. 25, 296-301

Rankin, S. M. (2008) Impact of bone marrow on respiratory disease. Curr. Opin Pharmacol. 8, 1-6

Ripa, R. S., Jørgensen, E., Wang, Y., Thune, J. J., Nilsson, J. C., Søndergaard, L, Johnsen, H. E., Køber, L., Grande, P., Kastrup, J. (2006) Stem cell mobilization induced by subcutaneous granulocyte-colony stimulating factor to improve cardiac regeneration after acute ST-elevation myocardial infarction: result of the double-blind, randomized, placebo-controlled stem cells in myocardial infarction (STEMMI) trial. Circulation. 113, 1983-1992

Roberts A. W. & Metcalf, D. (1995). Noncycling status of peripheral blood progenitor cells mobilized by granulocyte colony-stimulating factor and other cytokines. Blood. 86, 1600-1605

Rochefort, G. Y., Deforme, B., Lopez, A., Herault, O., Bonnet, P., Charbord, P., Eder, V., Domenech, J. (2006). Multipotential mesenchymal stem cells are mobilized into peripheral blood by hypoxia. Stem Cells. 24, 2202-2208.

Salani, D., Taraboletti, G., Rosano, L., Di Castro, V., Borsotti, P., Giavazzi, R., Bagnato, A. (2000). Endothelin-1 induces an angiogenic phenotype in cultured endothelial cells and stimulates neovascularization in vivo. Am. J. Pathol. 157, 1703-1711.

Semerad, C. L., Liu, F., Gregory, A. D., Stumpf, K., Link, D. C. (2002) G-CSF is an essential regulator of neutrophil trafficking from the bone marrow to the blood. Immunity. 17, 413-423

Shepherd, R. M., Capoccia, B. J., Devine, S. M., Dipersio, J., Trinkaus, K. M., Ingram, D., Link, D. C. (2006). Angiogenic cells can be rapidly mobilized and efficiently harvested from the blood flowing treatment with AMD3100. Blood. 108, 3662-3667

Takahashi, T., Kalka, C., Masuda, H., Chen, D., Silver, M., Kearney, M., Magner, M., Isner, J. M., Asahara, T. (1999). Ischemia- and cytokine-induced mobilization of bone marrow-derived endothelial progenitor cells for neovascularization. Nature. Med. 5, 434-438.

Uchida, N., He, D., Friera, A. M., Reitsma, M., Sasaki, D., Chen, B., Tsukamoto, A. (1997). The unexpected G0/G1 cell cycle status of mobilized hematopoietic stem cells from peripheral blood. Blood. 89, 465-472

Wengner, A. M., Pitchford, S. C., Furze, R. C., Rankin, S. M. (2008). The coordinated action of G-CSF and ELR+ CXC chemokines in neutrophil mobilization during acute inflammation. Blood. 111, 42-49

Wilson, A., Oser, G. M., Jaworski, M., Blanco-Bose, W. E., Laurenti, E., Adolphe, C., Essers, M. A., Macdonald, H. R., Trumpp, A. (2007). Dormant and Self-renewing hematopoietic stem cells and their niches. Ann. N.Y. Acad. Sci. 1106, 64-75

Yoder, M. C., Mead, L. E., Prater, D., Krier, T. R., Mroueh, K. N., Li, F., Krasich, R., Temm, C. J., Prchal, J. T., Ingram, D. A. (2007) Redefining endothelial progenitor cells via clonal analysis and hematopoietic stem/progenitor cell principals. Blood. 109, 1801-1809.

Yoon, C.-H., Hur, J., Park, K. W., Kim, J. H., Lee, C. S., Oh, I. Y., Kim, T. Y., Cho, H. J., Kang, H. J., Chae, I. H., et al. (2005). Synergistic neovascularization by mixed transplantation of early endothelial progenitor cells and late outgrowth endothelial cells. Circulation. 112, 1618-1627

Zernecke, A., Bot, I., Djalali-Talab, Y., Shagdarsuren, E., Bidzhekov, K., Meiler, S., Krohn, R., Schober, A., Sperandio, M., Soehnlein, O., et al. (2008). Protective role of CXC Receptor 4/CXC ligand 12 unveils the importance of neutrophils in atherosclerosis. Circulation Res. 102, 209-217

Zohlnhofer, D., Ott, I., Mehilli, J., Schömig, K., Michalk, F., Ibrahim, T., Meisetschläger, G., von Wedel, J., Bollwein, H., Seyfarth, M., Dirschinger, J., et al. (2006). Stem cell mobilization by granulocyte-colony stimulating factor in patients with acute myocardial infarction: a randomized controlled trial. JAMA. 295, 1003-1010

Zuk, P. A., Zhu, M., Ashjian, P., De Ugarte, D. A., Huang, J. I., Mizuno, H., Alfonso, Z. C., Fraser, J. K., Benhaim, P. & Hedrick, M. H. (2002) Human adipose tissue is a source of multipotent stem cells. Mol Biol Cell, 13, 4279-4295.

EXAMPLE 4

Effect of Blocking VEGFR1 on the Mobilisation of SPCs

Methods

Pre-Treatment with VEGF and Administration of Anti-VEGFR1 Antibody

Female BALB/c mice were purchased from Harlan (Oxford, United Kingdom). Mice, at the age of 8-10 weeks were administered VEGF (2.5 µg/mouse i.p.), or vehicle on 4 consecutive days. Additionally, Mice were administered anti-VEGFR1 or control IgG (2.5 mg/kg i.p. Ohki et al., 2005) 30 minutes before VEGF administration on days 1 and 3 of the 4 day VEGF-treatment protocol. 24 hours after the last injection, mice were administered a CXCR4 antagonist (AMD3100, 5 mg/kg i.p), KC (30 µg/kg i.v.) or vehicle and blood was collected via cardiac puncture 60 minutes later for enumeration of circulating SPC levels.

CFU-SPC (CFU-F) Assay to Elucidate Mobilized SPCs $5 \times 10^5$ cells were added to Mesencult media including supplements (Stemcell Technologies). Dishes were incubated for 7 days before media was changed, and then incubated for a further 14 days before the enumeration of SPC colonies (CFU-F). Plastic adherent bone marrow derived SPCs were shown to express CD29 and CD105 and were negative for CD45 and CD34 (FIG. 30a) as demonstrated in previous studies on stromal progenitor cells (Phinney et al., 1999; Pittenger et al., 1999). Furthermore, expanded SPC colonies were assessed for their ability to differentiate into other cell types (see below), and were capable of mesenchymal tri-lineage differentiation into adipocytes (FIG. 21c), osteocytes (FIG. 21d) and chondrocytes (FIG. 21e) These progenitor cells exhibit all the characteristics of murine mesenchymal stem cells (Pittenger et al., 1999)

The total number of colony forming units mobilized was calculated according to the number of colonies per plate×by the total number of leukocytes mobilized/number of cells seeded.

Result of Administration of Anti-VEGFR1 Antibody to VEGF-Pre-Treated Mice

Figure 32:
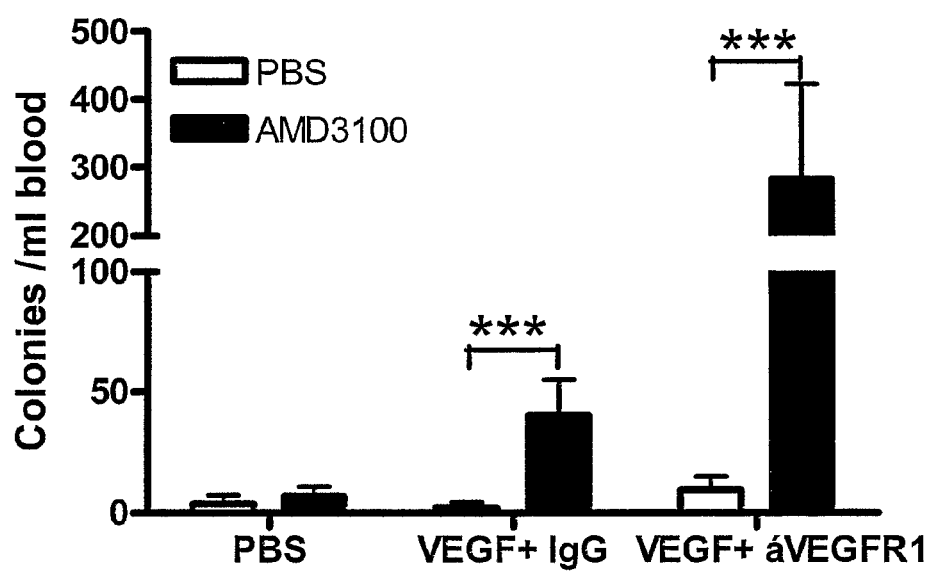

The continued antagonism or blocking of VEGFR-1 with an anti-VEGFR-1 antibody, in the presence of chronic VEGF administration, followed by acute CXCR4 antagonism, led to a significant increase in SPC mobilisation (FIG. 32) compared to VEGF-pre-treated mice co-administered control antibody (IgG) and administered CXCR4 antagonist. It is envisaged that provision of such a VEGFR-1 antagonist in a patient with elevated levels of VEGF and in combination with CXCR4 antagonism will increase MSC mobilisation.

REFERENCES

Ohki, Y., Heissig, B., Sato, Y., Akiyama, H., Zhu, Z., Hicklin, D. J., Shimada, K., Ogawa, H., Daida, H., Hattori, K., Ohsaka, A. (2005). Granulocyte colony-stimulating factor promotes neovascularisation by releasing vascular endothelial growth factor from neutrophils. FASEB J. 19, 2005-2017

Phinney, D. G., Kopen, G., Isaacson, R. L., Prockop, D. J. (1999). Plastic adherent stromal cells from the bone marrow of commonly used strains of inbred mice: variations in yield, growth, and differentiation. J. Cell. Biochem. 72, 570-585

Pittenger, M. F., Mackay, A. M., Beck, S. C., Jaiswal, R. K., Douglas, R., Mosca, J. D., Moorman, M. A., Simonetti, D. W., Craig, S., Marshak, D. R. (1999). Multilineage potential of adult human mesenchymal stem cells. Science. 284, 143-147

EXAMPLE 5

Effect of VEGFR on Serum TNFα Levels in LPS Peritonitis

Methods

For 4 days prior to LPS challenge mice received daily either 2.5 µg VEGF in 250 µL PBS intraperitoneally. or 250 µL PBS intraperitoneally. On day 5 mice were challenged with either 50 µg LPS in 100 µL PBS or 100 µL PBS intraperitoneally (control). 30 minutes prior to LPS challenge mice received either 150 µg AMD3100 in 100 µL saline intraperitoneally or 100 µL saline intraperitoneally.

One hour after LPS challenge mice were anaesthetised with urethane, blood was obtained by cardiac puncture, centrifuged and serum component stored at −70° C. for future analysis. The peritoneum was lavaged with 1 mL of PBS and centrifuged. Lavage fluid was collected and stored at −70° C. for future analysis whilst the cell pellet was resuspended in 150 µL volume of PBS for total cell and differential counts.

TNFα levels were measured in serum and lavage fluid by ELISA.

Results

Figure 33:
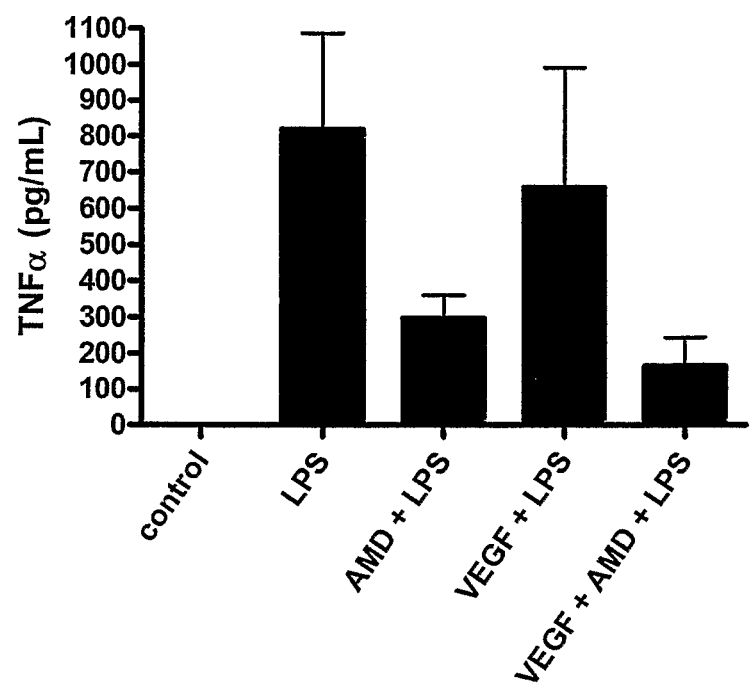

Evidence that this treatment protocol has an immunosuppressive effect is shown in FIG. 33. This figure indicates that when mice are pre-treated with VEGF over 4 days, followed by administration of the CXCR4 antagonist on day 5, exhibit an attenuated inflammatory response to an inflammatory stimulus (intraperitoneal administration of LPS. In this experiment a reduction in TNF a production was noted in mice treated with VEGF in combination with the CXCR4 antagonist.

The invention claimed is:

1. A method for mobilizing mesenchymal stem cells (MSC) in a patient, wherein the method comprises the steps of (i) administering a VEGFR agonist to the patient; and (ii) administering an antagonist of CXCR4 to the patient.

2. The method of claim 1 wherein the VEGFR agonist is a VEGFR-2 agonist.

3. A method for mobilizing mesenchymal stem cells (MSC) in a patient with elevated circulating levels of VEGF, wherein the method comprises administering an antagonist of CXCR4 to the patient.

4. The method of claim 3 wherein the method further comprises administering a VEGFR-1 antagonist.

5. The method of claim 4 wherein the VEGFR-1 antagonist is an antibody or fragment thereof.

6. The method of claim 1, wherein the antagonist of CXCR4 is AMD3100.

7. The method of claim 1, wherein the method further includes harvesting MSC.

8. The method of claim 7, wherein the harvested MSC are cultivated in vitro.

9. The method of claim 8, wherein the cultivated cells are administered back to the patient or to another patient.

10. The method of claim 8, wherein the cultivated cells are genetically modified.

11. The method of claim 10, wherein the genetically modified cells are more resistant to apoptosis than the wild-type cells.

12. The method of claim 9, wherein the cultivated cells are targeted to damaged tissue in the recipient of said cultivated cells.

13. The method of claim 12, wherein the damaged tissue is damaged by ischemia, radiotherapy, chemotherapy, auto-immune disease or physical injury.

14. The method of claim 1 or claim 3 further comprising mobilizing endothelial progenitor cells (EPC).

15. A method for mobilizing mesenchymal stem cells (MSC) from the bone marrow of a patient, wherein the method comprises the steps of (i) administering a VEGFR agonist to the patient; and (ii) administering an antagonist of CXCR4 to the patient.

16. A method for mobilizing mesenchymal stem cells (MSC) in a patient, wherein the method comprises the steps of (i) chronically administering a VEGFR agonist to the patient; and (ii) administering an antagonist of CXCR4 to the patient.

17. A method for mobilizing mesenchymal stem cells (MSC) in a patient, wherein the method comprises the steps of (i) administering a VEGFR agonist to the patient; and (ii) acutely administering an antagonist of CXCR4 to the patient.

18. The method of claim 17 wherein the antagonist of CXCR4 is administered directly/locally to a perfused bone.

19. A method for mobilizing mesenchymal stem cells (MSC) in a patient, wherein the method comprises the steps of (i) administering a VEGF-E to the patient; and (ii) administering an antagonist of CXCR4 to the patient.

\* \* \* \* \*

UNITED STATES PATENT AND TRADEMARK OFFICE
CERTIFICATE OF CORRECTION

PATENT NO. : 8,440,199 B2
APPLICATION NO. : 12/747302
DATED : May 14, 2013
INVENTOR(S) : Sara Margaret Rankin and Simon Charles Pitchford Page 1 of 1

It is certified that error appears in the above-identified patent and that said Letters Patent is hereby corrected as shown below:

In the Claims

Column 38, line 13, "claim 17" should be -- claim 15 --.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,440,199 B2
APPLICATION NO. : 12/747302
DATED : May 14, 2013
INVENTOR(S) : Rankin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 221 days.

Signed and Sealed this
Eighth Day of September, 2015

Michelle K. Lee
*Director of the United States Patent and Trademark Office*